(12) United States Patent
Gilbert et al.

(10) Patent No.: US 6,495,668 B1
(45) Date of Patent: Dec. 17, 2002

(54) GROWTH FACTOR HOMOLOG ZVEGF4

(75) Inventors: Teresa Gilbert, Seattle, WA (US); Charles E. Hart, Woodinville, WA (US); Paul O. Sheppard, Granite Falls, WA (US); Debra G. Gilbertson, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/564,595

(22) Filed: May 3, 2000

Related U.S. Application Data

(60) Provisional application No. 60/132,250, filed on May 3, 1999, provisional application No. 60/164,463, filed on Nov. 10, 1999, and provisional application No. 60/180,169, filed on Feb. 4, 2000.

(51) Int. Cl.[7] .................. A61K 38/24; A61K 38/27; C12N 15/09; C07H 21/04
(52) U.S. Cl. ............... 530/399; 435/69.4; 435/70.1; 530/350; 536/23.4
(58) Field of Search .................. 435/69.4, 375, 435/377; 514/2; 530/350, 402, 387.1, 399

(56) References Cited

FOREIGN PATENT DOCUMENTS

WO    A1 00/27879    5/2000

OTHER PUBLICATIONS

. B.Robson, J.Garnier. Introduction to Proteins and Protein Engineering. 1986, Elsevier, p. 41.*
National Cancer Institute, Cancer Genome Anatomy Project, Accession No. AA488780, 1997.
Fujiwara et al., Genbank Accession No. D80118, 1995.
Strausberg, Genbank Accession No. AA488780, 1997.
Incyte Clone Information Results, INC1966916, Oct. 17, 1996.
Incyte Clone Information Results, INC2521401, Feb. 4, 1997.
Incyte Clone Information Results, INC2762339, Mar. 10, 1997.
Incyte Clone Information Results, INC2997909, Oct. 6, 1997.
Incyte Clone Information Results, INC3096554, Nov. 17, 1997.
Incyte Clone Information Results, INC6250517, Mar. 1, 2000.
Incyte Clone Information Results, INC6904711, Mar. 1, 2000.
Incyte Clone Information Results, INC6254291, Mar. 1, 2000.
TIGR Tentative Human Consensus Sequence, THC D80118, Jul. 3, 1997.

* cited by examiner

Primary Examiner—Christine J. Saoud
Assistant Examiner—Olga N. Chernyshev
(74) Attorney, Agent, or Firm—Gary E. Parker

(57) ABSTRACT

Polypeptide growth factors, methods of making them, polynucleotides encoding them, antibodies to them, and methods of using them are disclosed. Multimers of the polypeptides are also disclosed. The polypeptides, multimeric proteins, and polynucleotides can be used in the study and regulation of cell and tissue development, as components of cell culture media, and as diagnostic agents.

14 Claims, 8 Drawing Sheets

Figure 1A:
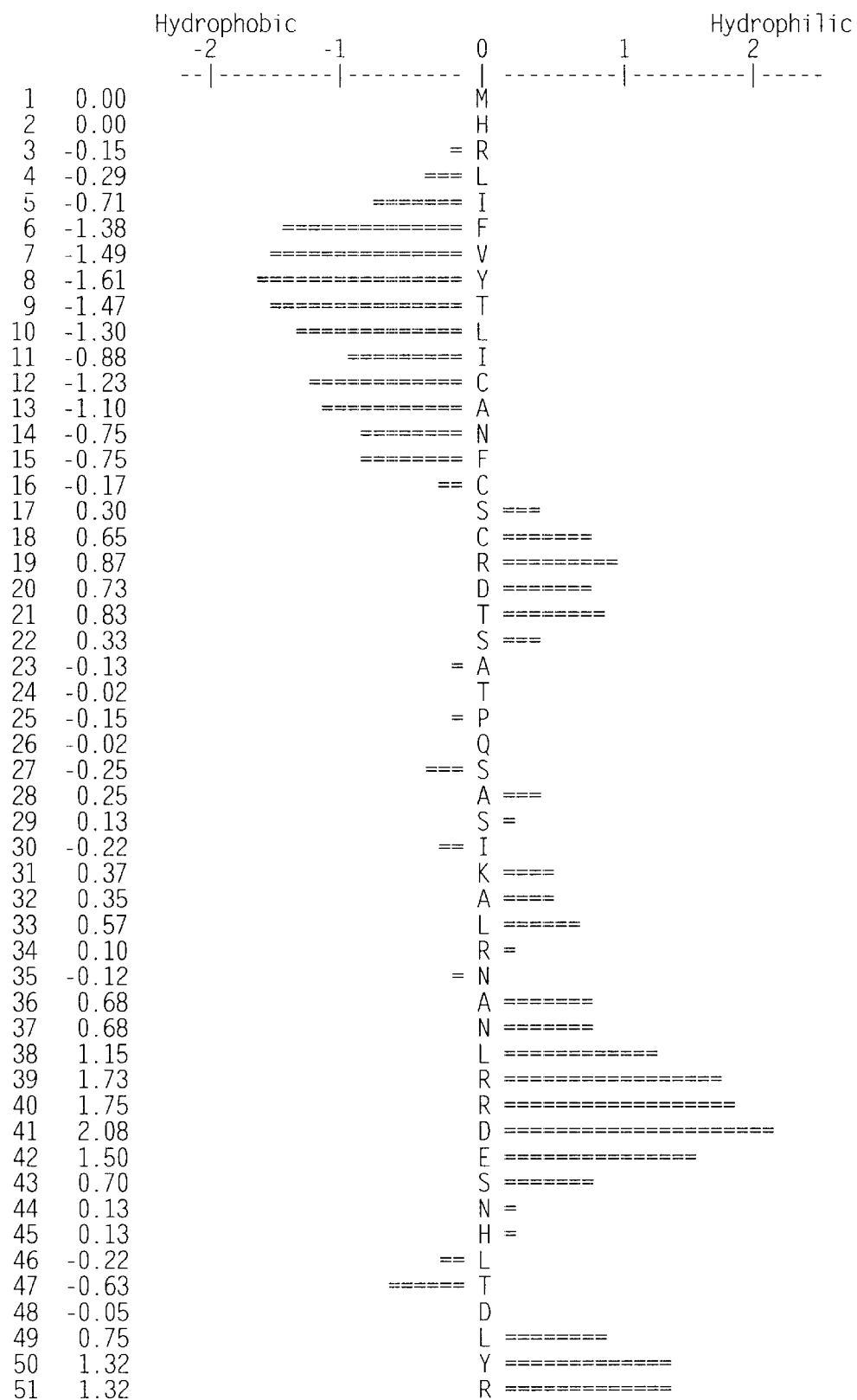
Figure 1G:
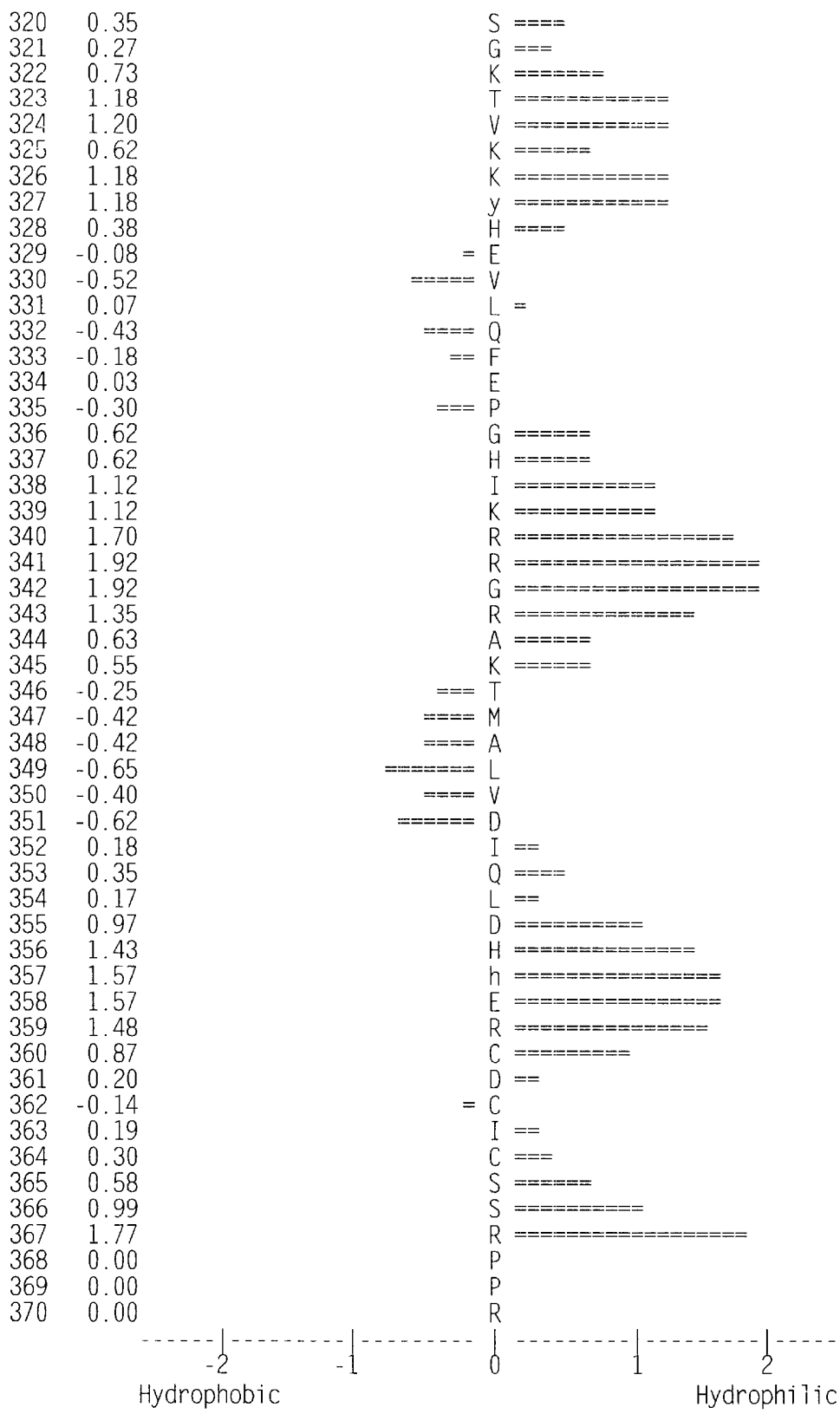

| | | | |
|---|---|---|---|
|212|0.82| |K ========|
|213|1.62| |K ================|
|214|0.70| |I =======|
|215|0.70| |A =======|
|216|0.13| |E =|
|217|0.18| |F ==|
|218|0.77| |D ========|
|219|0.77| |T ========|
|220|0.88| |V ========|
|221|0.08| |E =|
|222|0.65| |D =======|
|223|0.52| |L =====|
|224|-0.40|====|L|
|225|-0.87|=========|K|
|226|-0.57|======|Y|
|227|0.23| |F ==|
|228|-0.22|==|N|
|229|0.00| |P|
|230|0.45| |E =====|
|231|0.92| |S =========|
|232|1.42| |W ==============|
|233|0.62| |Q ======|
|234|1.07| |E ==========|
|235|1.27| |D ============|
|236|1.02| |L ==========|
|237|0.13| |E =|
|238|-0.67|=======|N|
|239|0.13| |M =|
|240|-0.43|====|Y|
|241|-0.47|=====|L|
|242|0.25| |D ===|
|243|0.65| |T =======|
|244|1.45| |P ==============|
|245|0.95| |R ==========|
|246|1.52| |y ===============|
|247|1.57| |R ===============|
|248|1.08| |G ==========|
|249|0.98| |R ==========|
|250|0.98| |S ==========|
|251|1.48| |y ==============|
|252|1.48| |H ==============|
|253|1.48| |D ==============|
|254|1.97| |R ===================|
|255|1.80| |K =================|
|256|1.80| |S =================|
|257|1.00| |K ==========|
|258|1.00| |V ==========|
|259|1.45| |D ==============|
|260|0.65| |L =======|
|261|0.93| |D =========|
|262|0.93| |R =========|
|263|1.73| |L =================|
|264|1.15| |N ============|
|265|1.15| |D ============|

GROWTH FACTOR HOMOLOG ZVEGF4

CROSS-REFERENCE TO RELATED APPLICATIONS

This application claims the benefit under 35 U.S.C. 119(e) of U.S. provisional applications Serial No. 60/132,250, filed May 3, 1999; Ser. No. 60/164,463, filed Nov. 10, 1999; and Ser. No. 60/180,169, filed Feb. 4, 2000.

BACKGROUND OF THE INVENTION

In multicellular animals, cell growth, differentiation, and migration are controlled by polypeptide growth factors. These growth factors play a role in both normal development and pathogenesis, including the development of solid tumors.

Polypeptide growth factors influence cellular events by binding to cell-surface receptors, many of which are tyrosine kinases. Binding initiates a chain of signalling events within the cell, which ultimately results in phenotypic changes, such as cell division, protease production, and cell migration.

Growth factors can be classified into families on the basis of structural similarities. One such family, the PDGF (platelet derived growth factor) family, is characterized by a dimeric structure stabilized by disulfide bonds. This family includes PDGF, the placental growth factors (PlGFs), and the vascular endothelial growth factors (VEGFs). The individual polypeptide chains of these proteins form characteristic higher-order structures having a bow tie-like configuration about a cystine knot, formed by disulfide bonding between pairs of cysteine residues. Hydrophobic interactions between loops contribute to the dimerization of the two monomers. See, Daopin et al., Science 257:369, 1992; Lapthorn et al., Nature 369:455, 1994. Members of this family are active as both homodimers and heterodimers. See, for example, Heldin et al., EMBO J. 7:1387–1393, 1988; Cao et al., J. Biol. Chem. 271:3154–3162, 1996. The cystine knot motif and "bow tie" fold are also characteristic of the growth factors transforming growth factor-beta (TGF-β) and nerve growth factor (NGF), and the glycoprotein hormones. Although their amino acid sequences are quite divergent, these proteins all contain the six conserved cysteine residues of the cystine knot.

Five vascular endothelial growth factors have been identified: VEGF, also known as vascular permeability factor (Dvorak et al., Am. J. Pathol. 146:1029–1039, 1995); VEGF-B (Olofsson et al., Proc. Natl. Acad. Sci. USA 93:2567–2581, 1996; Hayward et al., WIPO Publication WO 96/27007); VEGF-C (Joukov et al., EMBO J. 15:290–298, 1996); VEGF-D (Oliviero, WO 97/12972; Achen et al., WO 98/07832), and zvegf3 (SEQ ID NO:32 and NO:33; co-pending U.S. patent applications Ser. Nos. 60/111,173, 60/142,576, and 60/161,653). Five VEGF polypeptides (121, 145, 165, 189, and 206 amino acids) arise from alternative splicing of the VEGF mRNA.

VEGFs stimulate the development of vasculature through a process known as angiogenesis, wherein vascular endothelial cells re-enter the cell cycle, degrade underlying basement membrane, and migrate to form new capillary sprouts. These cells then differentiate, and mature vessels are formed. This process of growth and differentiation is regulated by a balance of pro-angiogenic and anti-angiogenic factors. Angiogenesis is central to normal formation and repair of tissue, occuring in embryo development and wound healing. Angiogenesis is also a factor in the development of certain diseases, including solid tumors, rheumatoid arthritis, diabetic retinopathy, macular degeneration, and atherosclerosis.

A number of proteins from vertebrates and invertebrates have been identified as influencing neural development. Among those molecules are members of the neuropilin family and the semaphorin/collapsin family.

Three receptors for VEGF have been identified: KDR/Flk-1 (Matthews et al., Proc. Natl. Acad. Sci. USA 88:9026–9030, 1991), Flt-1 (de Vries et al., Science 255:989–991, 1992), and neuropilin-1 (Soker et al., Cell 92:735–745, 1998). Neuropilin-1 is also a receptor for PlGF-2 (Migdal et al., J. Biol. Chem. 273: 22272–22278, 1998).

Neuropilin-1 is a cell-surface glycoprotein that was initially identified in Xenopus tadpole nervous tissues, then in chicken, mouse, and human. The primary structure of neuropilin-1 is highly conserved among these vertebrate species. Neuropilin-1 has been demonstrated to be a receptor for various members of the semaphorin family including semaphorin III (Kolodkin et al., Cell 90:753–762, 1997), Sema E and Sema IV (Chen et al., Neuron 19:547–559, 1997). A variety of activities have been associated with the binding of neuropilin-1 to its ligands. For example, binding of semaphorin III to neuropilin-1 can induce neuronal growth cone collapse and repulsion of neurites in vitro (Kitsukawa et al., Neuron 19: 995–1005, 1997). Experiments with transgenic mice indicate the involvement of neuropilin-1 in the development of the cardiovascular system, nervous system, and limbs. See, for example, Kitsukawa et al., Development 121:4309–4318, 1995; and Takashima et al., American Heart Association 1998 Meeting, Abstract #3178.

Semaphorins are a large family of molecules which share the defining semaphorin domain of approximately 500 amino acids. Dimerization is believed to be important for functional activity (Klostermann et al., J. Biol. Chem. 273:7326–7331, 1998). Collapsin-1, the first identified vertebrate member of the semaphorin family of axon guidance proteins, has also been shown to form covalent dimers, with dimerization necessary for collapse activity (Koppel et al., J. Biol. Chem. 273:15708–15713, 1998). Semaphorin III has been associated in vitro with regulating growth clone collapse and chemorepulsion of neurites. Semaphorins have been shown to be responsible for a variety of developmental effects, including effects on sensory afferent innervation, skeletal and cardiac development (Fehar et al., Nature 383:525–528, 1996), immunosuppression via inhibition of cytokines (Mangasser-Stephan et al., Biochem. Biophys. Res. Comm. 234:153–156, 1997), and promotion of B-cell aggregation and differentiation (Hall et al., Proc. Natl. Acad. Sci. USA 93:11780–11785, 1996). CD100 has also been shown to be expressed in many T-cell lymphomas and may be a marker of malignant T-cell neoplasms (Dorfman et al., Am. J. Pathol. 153:255–262, 1998). Transcription of the mouse semaphorin gene, M-semaH, correlates with metastatic ability of mouse tumor cell lines (Christensen et al., Cancer Res. 58:1238–1244, 1998).

The role of growth factors, other regulatory molecules, and their receptors in controlling cellular processes makes them likely candidates and targets for therapeutic intervention. Platelet-derived growth factor, for example, has been disclosed for the treatment of periodontal disease (U.S. Pat. No. 5,124,316), gastrointestinal ulcers (U.S. Pat. No. 5,234,908), and dermal ulcers (Robson et al., Lancet 339:23–25, 1992). Inhibition of PDGF receptor activity has been shown to reduce intimal hyperplasia in injured baboon arteries (Giese et al., Restenosis Summit VIII, Poster Session #23, 1996; U.S. Pat. No. 5,620,687). PDGF has also been shown to stimulate bone cell replication (reviewed by Canalis et al., *Endocrinology and Metabolism Clinics of North America* 18:903–918, 1989), to stimulate the production of collagen by bone cells (Centrella et al., *Endocrinology* 125:13–19, 1989) and to be useful in regenerating periodontal tissue (U.S. Pat. No. 5,124,316; Lynch et al., *J. Clin. Periodontol.* 16:545–548, 1989). Vascular endothelial growth factors (VEGFs) have been shown to promote the growth of blood vessels in ischemic limbs (Isner et al., *The Lancet* 348:370–374, 1996), and have been proposed for use as wound-healing agents, for treatment of periodontal disease, for promoting endothelialization in vascular graft surgery, and for promoting collateral circulation following myocardial infarction (WIPO Publication No. WO 95/24473; U.S. Pat. No. 5,219,739). VEGFs are also useful for promoting the growth of vascular endothelial cells in culture. A soluble VEGF receptor (soluble flt-1) has been found to block binding of VEGF to cell-surface receptors and to inhibit the growth of vascular tissue in vitro (*Biotechnology News* 16(17):5–6, 1996).

In view of the proven clinical utility of polypeptide growth factors, there is a need in the art for additional such molecules for use as therapeutic agents, diagnostic agents, and research tools and reagents.

The present invention provides such polypeptides for these and other uses that should be apparent to those skilled in the art from the teachings herein.

DESCRIPTION OF THE INVENTION

The present invention provides an isolated polypeptide of at least 15 amino acid residues comprising an epitope-bearing portion of a protein of SEQ ID NO:2. Within certain embodiments, the polypeptide comprises a segment that is at least 70% identical to residues 52–179 of SEQ ID NO:2 or residues 258–370 of SEQ ID NO:2. Within other embodiments, the polypeptide is selected from the group consisting of residues 19–179 of SEQ ID NO:2, residues 52–179 of SEQ ID NO:2, residues 19–257 of SEQ ID NO:2, residues 52–257 of SEQ ID NO:2, residues 19–253 of SEQ ID NO:2, residues 52–253 of SEQ ID NO:2, residues 19–370 of SEQ ID NO:2, residues 52–370 of SEQ ID NO:2, residues 258–370 of SEQ ID NO:2, and residues 180–370 of SEQ ID NO:2.

The invention also provides an isolated polypeptide comprising a sequence of amino acids of the formula $R1_x\text{-}R2_y\text{-}R3_z$, wherein R1 is a polypeptide of from 100 to 130 residues in length, is at least 70% identical to residues 52–179 of SEQ ID NO:2, and comprises a sequence motif C[KR]Y[DNE][WYF]X{11,15}G[KR][WYF]C (SEQ ID NO:4) corresponding to residues 109–131 of SEQ ID NO:2; R2 is a polypeptide at least 90% identical to residues 180–257 of SEQ ID NO:2; R3 is a polypeptide at least 70% identical in amino acid sequence to residues 258–370 of SEQ ID NO:2 and comprises cysteine residues at positions corresponding to residues 272, 302, 306, 318, 360, and 362 of SEQ ID NO:2, a glycine residue at a position corresponding to residue 304 of SEQ ID NO:2, and a sequence motif CX{18,33}CXGXCX{6,33}CX{20,50}CXC (SEQ ID NO:3) corresponding to residues 272–362 of SEQ ID NO:2; and each of x, y, and z is individually 0 or 1, subject to the limitations that at least one of x and z is 1, and, if x and z are each 1, then y is 1. There are thus provided isolated polypeptides of the above formula wherein (a) x=1, (b) z=1, and (c) x=1 and z=1. Within certain embodiments, x=1 and R1 is at least 90% identical to residues 52–179 of SEQ ID NO:2 or residues 19–179 of SEQ ID NO:2. Within related embodiments, x=1 and R1 comprises residues 52–179 of SEQ ID NO:2. Within other embodiments, z=1 and R3 is at least 90% identical to residues 258–370 of SEQ ID NO:2 or R3 comprises residues 258–370 of SEQ ID NO:2. Within other embodiments, x=1, z=1, and R3 is at least 90% identical to residues 258–370 of SEQ ID NO:2; and x=1, z=1, R1 is at least 90% identical to residues 52–179 of SEQ ID NO:2, and R2 is at least 90% identical to residues 180–257 of SEQ ID NO:2. Within additional embodiments, x=1, z=1, and the polypeptide comprises residues 19–370 of SEQ ID NO:2 or residues 52–370 of SEQ ID NO:2. The isolated polypeptide may further comprise cysteine residues at positions corresponding to residues 308 and 316 of SEQ ID NO:2. Within other embodiments, the isolated polypeptide further comprises an affinity tag. Within a related embodiment, the isolated polypeptide comprises an immunoglobulin constant domain.

The present invention also provides an isolated protein comprising a first polypeptide operably linked to a second polypeptide, wherein the first polypeptide comprises a sequence of amino acids of the formula $R1_x\text{-}R2_y\text{-}R3_z$ as disclosed above. The protein modulates cell proliferation, apoptosis, differentiation, metabolism, or migration. Within one embodiment, the protein is a heterodimer. Within related embodiments, the second polypeptide is selected from the group consisting of VEGF, VEGF-B, VEGF-C, VEGF-D, zvegf3 (SEQ ID NO:33), PlGF, PDGF-A, and PDGF-B. Within other related embodiments, x=1, z=1, and the second polypeptide comprises residues 46–345 of SEQ ID NO:33; x=1 and the second polypeptide comprises residues 46–170 of SEQ ID NO:33; or z=1 and the second polypeptide comprises residues 235–345 of SEQ ID NO:33.

Within another embodiment, the protein is a homodimer.

There is also provided an isolated protein produced by a method comprising the steps of (a) culturing a host cell containing an expression vector comprising the following operably linked elements: a transcription promoter; a DNA segment encoding a polypeptide selected from the group consisting of (i) residues 52–370 of SEQ ID NO:2, (ii) residues 52–253 of SEQ ID NO:2, (iii) residues 180–370 of SEQ ID NO:2, and (iv) residues 258–370 of SEQ ID NO:2; and a transcription terminator, under conditions whereby the DNA segment is expressed; and (b) recovering from the cell the protein product of expression of the DNA construct.

Within another aspect of the invention there is provided an isolated polynucleotide of up to approximately 4.4 kb in length, wherein said polynucleotide encodes a polypeptide as disclosed above. Within one embodiment of the invention, the polynucleotide is DNA.

Within a further aspect of the invention there is provided an expression vector comprising the following operably linked elements: (a) a transcription promoter; (b) a DNA polynucleotide as disclosed above; and (c) a transcription terminator. The vector may further comprise a secretory signal sequence operably linked to the DNA polynucleotide.

Also provided by the invention is a cultured cell into which has been introduced an expression vector as disclosed above, wherein the cell expresses the polypeptide encoded by the DNA polynucleotide. The cultured cell can be used within a method of producing a polypeptide, the method comprising culturing the cell and recovering the expressed polypeptide.

The proteins provided herein can be combined with a pharmaceutically acceptable vehicle to provide a pharmaceutical composition.

The invention also provides an antibody that specifically binds to an epitope of a polypeptide as disclosed above. Antibodies of the invention include, inter alia, monoclonal antibodies and single chain antibodies, and may be linked to a reporter molecule.

The invention further provides a method for detecting a genetic abnormality in a patient, comprising the steps of (a) obtaining a genetic sample from a patient, (b) incubating the genetic sample with a polynucleotide comprising at least 14 contiguous nucleotides of SEQ ID NO: 1 or the complement of SEQ ID NO: 1, under conditions wherein the polynucleotide will hybridize to a complementary polynucleotide sequence, to produce a first reaction product, and (c) comparing the first reaction product to a control reaction product, wherein a difference between the first reaction product and the control reaction product is indicative of a genetic abnormality in the patient.

The invention also provides a polypeptide comprising a sequence selected from the group consisting of: residues 1–302 of SEQ ID NO:54; residues 1–316 of SEQ ID NO:55; residues 1–317 of SEQ ID NO:56; and residues 1–303 of SEQ ID NO:57.

The invention also provides a method of activating a cell-surface PDGF receptor, comprising exposing a cell comprising a cell-surface PDGF receptor to a polypeptide or protein as disclosed above, whereby the polypeptide or protein binds to and activates the receptor.

The invention also provides a method of inhibiting a PDGF receptor-mediated cellular process, comprising exposing a cell comprising a cell-surface PDGF receptor to a compound that inhibits binding of a polypeptide or protein as disclosed above to the receptor.

The invention also provides a method of stimulating the growth of bone tissue, comprising applying to bone a growth-stimulating amount of a polypeptide or protein as disclosed above.

The invention also provides a method of modulating the proliferation, differentiation, migration, or metabolism of bone cells, comprising exposing bone cells to an effective amount of a polypeptide or protein as disclosed above.

These and other aspects of the invention will become evident upon reference to the following detailed description of the invention and the attached drawings.

In the accompanying drawings:

Figure 1B:
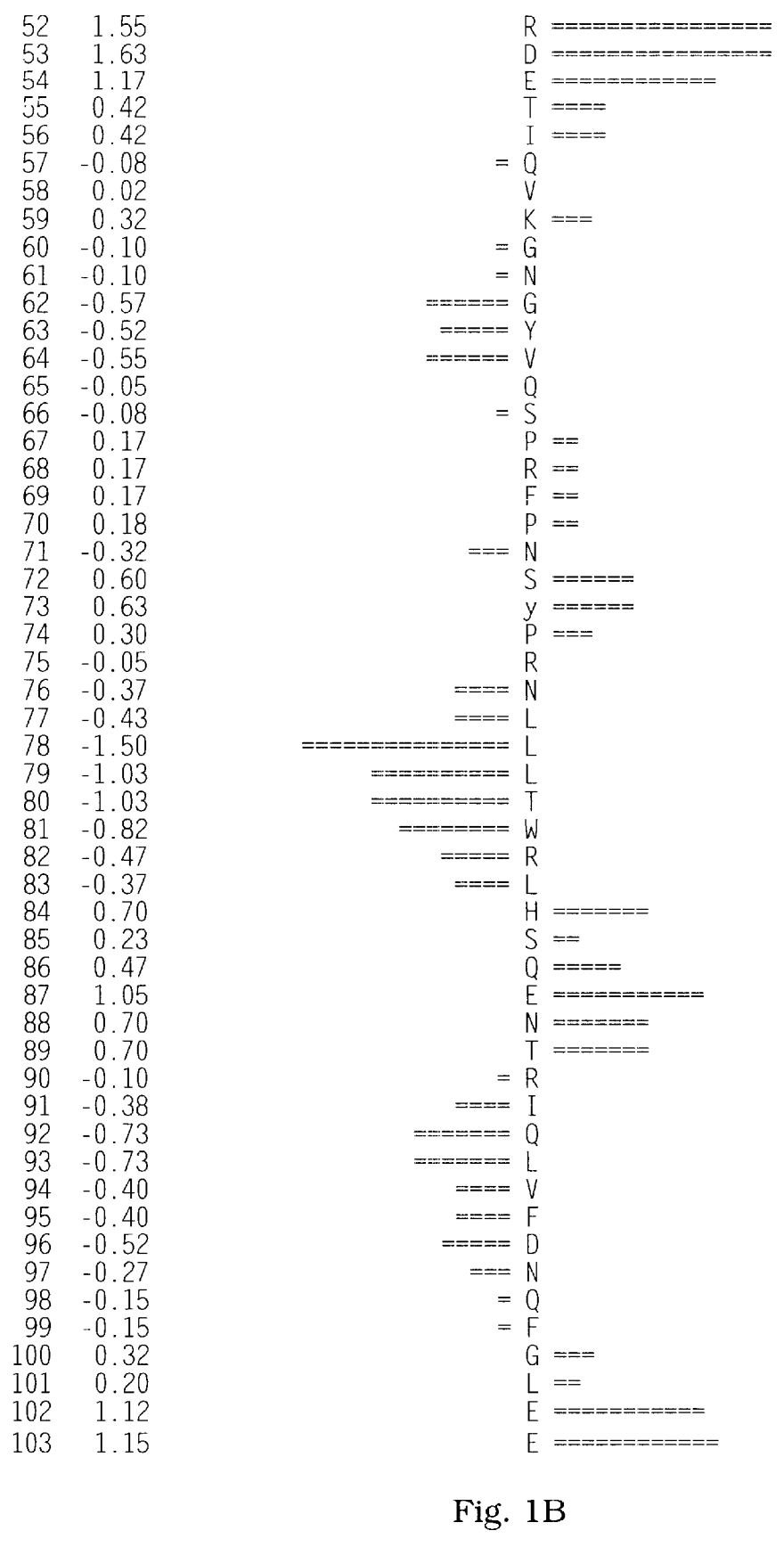
Figure 1C:
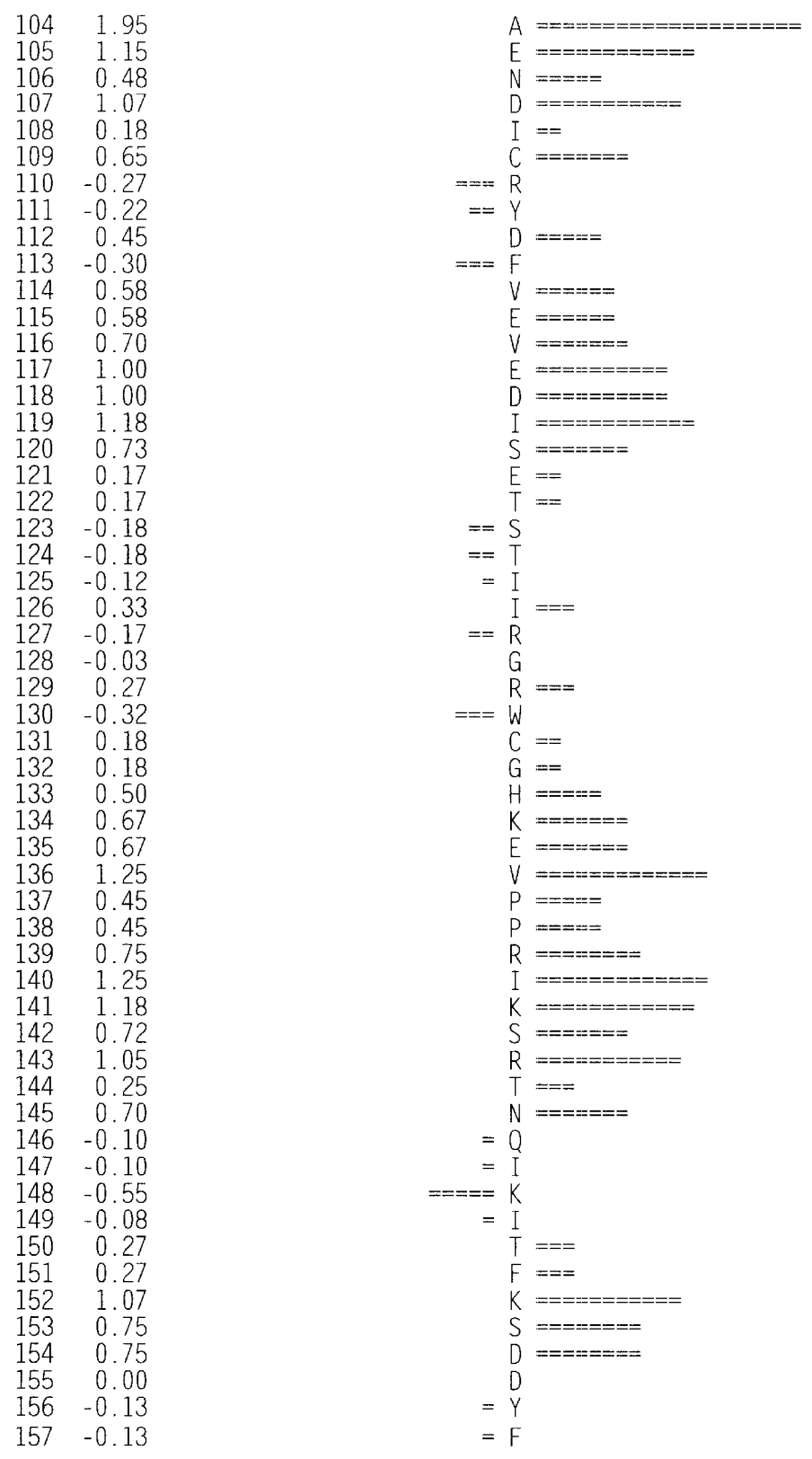
Figure 1D:
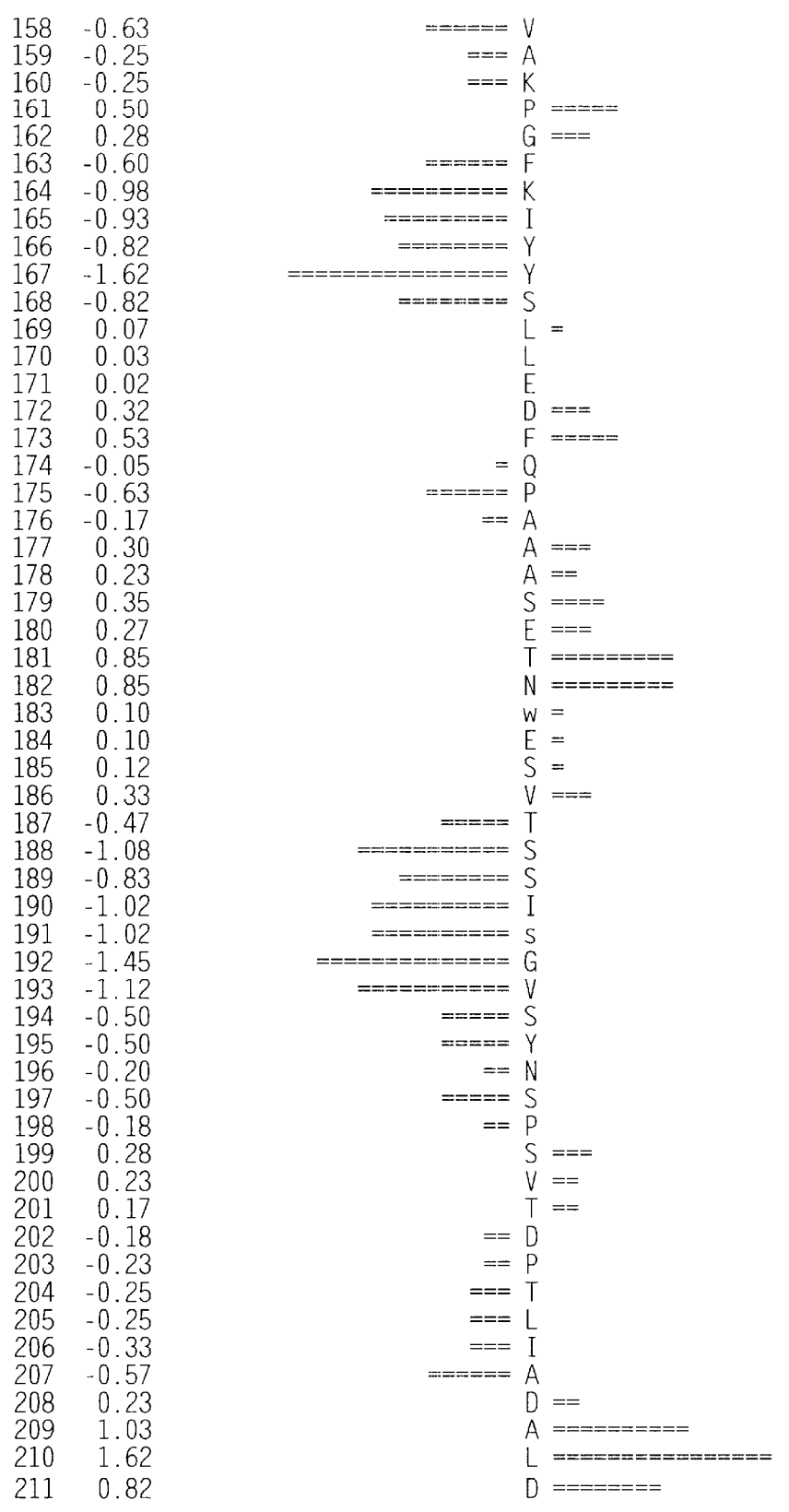
Figure 1F:
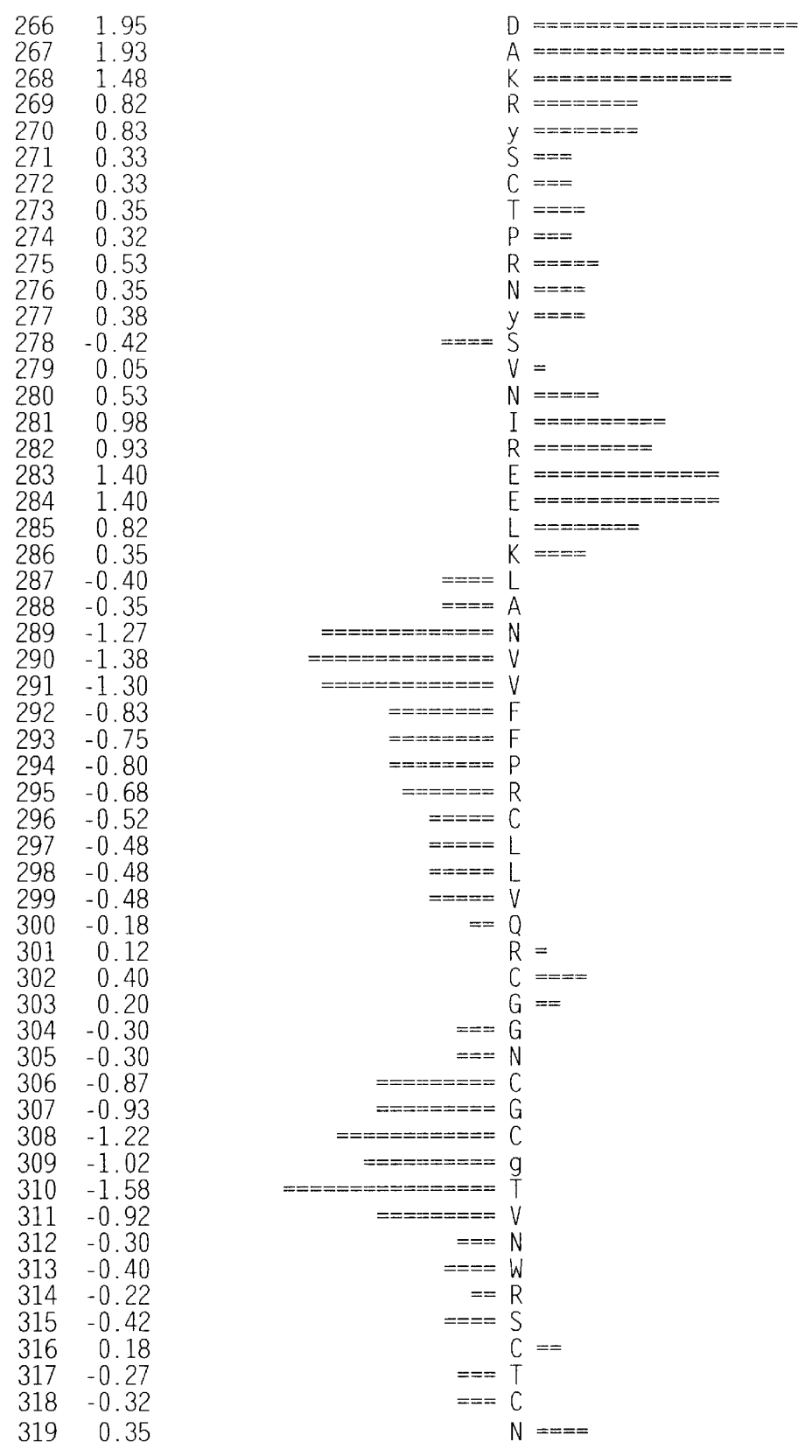

FIGS. 1A–1G are a Hopp/Woods hydrophilicity profile of the amino acid sequence shown in SEQ ID NO:2. The profile is based on a sliding six-residue window. Buried G, S, and T residues and exposed H, Y, and W residues were ignored. These residues are indicated in the figure by lower case letters.

Figure 2:
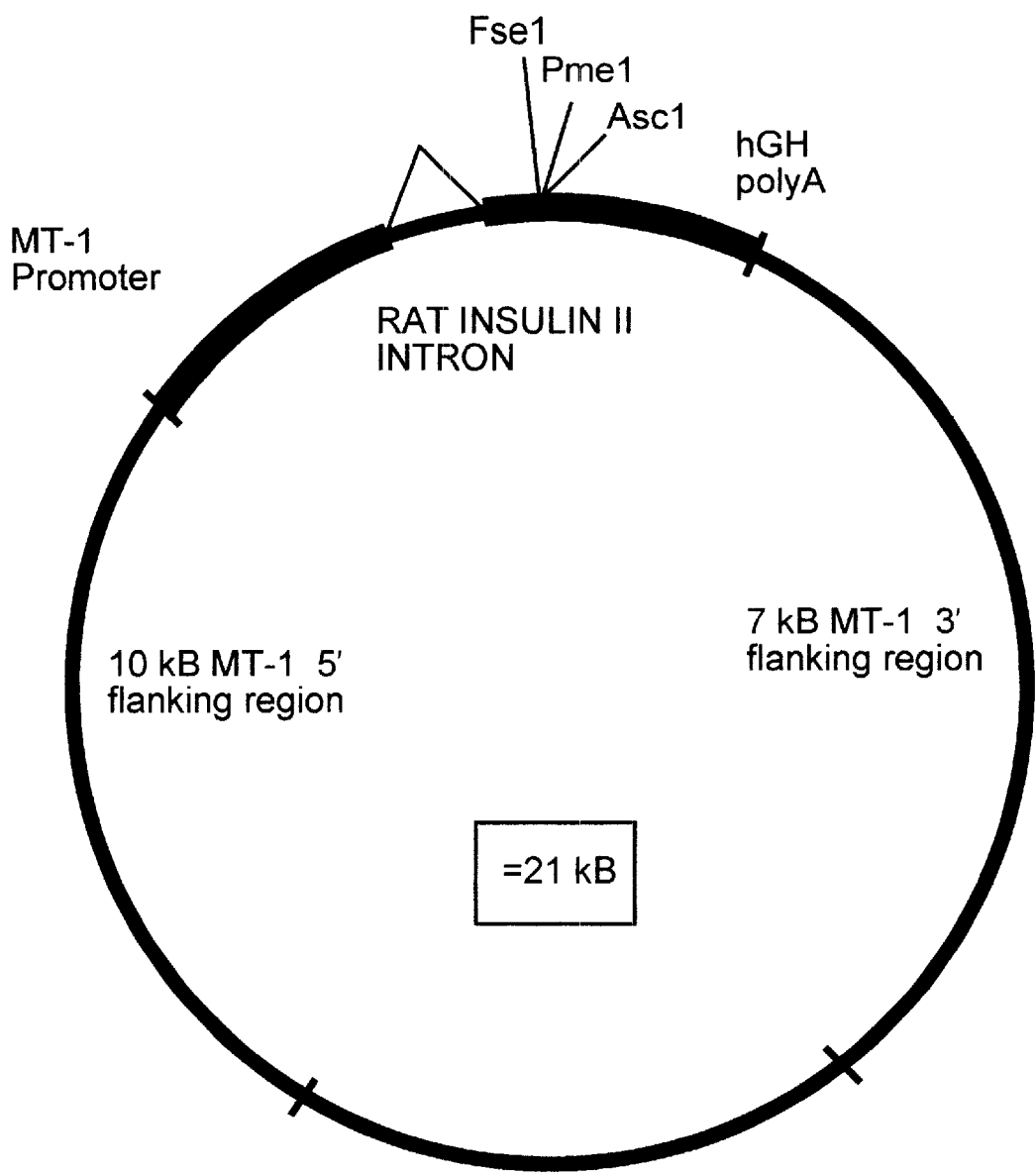

FIG. 2 is an illustration of the vector pHB 12–8 for use in expressing cDNAs in transgenic animals.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459–463, 1982; Guan et al., *Gene* 67:21–30, 1987), Glu-Glu affinity tag (Grussenmeyer et al., *Proc. Natl. Acad. Sci. USA* 82:7952–4, 1985; see SEQ ID NO:5), substance P, Flag™ peptide (Hopp et al., *Biotechnology* 6:1204–10, 1988), streptavidin binding peptide, thioredoxin, ubiquitin, cellulose binding protein, T7 polymerase, or other antigenic epitope or binding domain. See, in general, Ford et al., *Protein Expression and Purification* 2: 95–107, 1991. DNAs encoding affinity tags and other reagents are available from commercial suppliers (e.g., Pharmacia Biotech, Piscataway, N.J.; New England Biolabs, Beverly, Mass.; and Eastman Kodak, New Haven, Conn.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "beta-strand-like region" is a region of a protein characterized by certain combinations of the polypeptide backbone dihedral angles phi ($\phi$ and psi ($\psi$). Regions wherein $\phi$ is less than −60° and $\psi$ is greater than 90° are beta-strand-like. Those skilled in the art will recognize that the limits of a β-strand are somewhat imprecise and may vary with the criteria used to define them. See, for example, Richardson and Richardson in Fasman, ed., Prediction of Protein Structure and the Principles of Protein Conformation, Plenum Press, New York, 1989; and Lesk, *Protein Architecture: A Practical Approach*, Oxford University Press, New York, 1991.

A "complement" of a polynucleotide molecule is a polynucleotide molecule having a complementary base sequence and reverse orientation as compared to a reference sequence. For example, the sequence 5' ATGCACGGG 3' is complementary to 5° CCCGTGCAT 3'.

"Corresponding to", when used in reference to a nucleotide or amino acid sequence, indicates the position in a second sequence that aligns with the reference position when two sequences are optimally aligned.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated polynucleotide molecules of the present invention are free of other genes with which they are ordinarily associated, but may include naturally occurring 5' and 3' untranslated regions such as promoters and terminators. The identification of associated regions will be evident to one of ordinary skill in the art (see, for example, Dynan and Tijan, *Nature* 316:774–78, 1985).

An "isolated" polypeptide or protein is a polypeptide or protein that is found in a condition other than its native environment, such as apart from blood and animal tissue. Within one embodiment, the isolated polypeptide or protein is substantially free of other polypeptides or proteins, particularly other polypeptides or proteins of animal origin. The polypeptides or proteins may be provided in a highly purified form, i.e. greater than 95% pure or greater than 99% pure. When used in this context, the term "isolated" does not exclude the presence of the same polypeptide or protein in alternative physical forms, such as dimers or alternatively glycosylated or derivatized forms.

A "motif" is a series of amino acid positions in a protein sequence for which certain amino acid residues are required. A motif defines the set of possible residues at each such position.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function (s) of the sequences are retained.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±20%.

All references cited herein are incorporated by reference in their entirety.

The present invention is based in part upon the discovery of a novel DNA molecule that encodes a polypeptide comprising a growth factor domain and a CUB domain. The growth factor domain is characterized by an arrangement of cysteine residues and beta strands that is characteristic of the "cystine knot" structure of the PDGF family. The CUB domain shows sequence homology to CUB domains in the neuropilins (Takagi et al., *Neuron* 7:295–307, 1991; Soker et al., ibid.), human bone morphogenetic protein-1 (Wozney et al., *Science* 242:1528–1534, 1988), porcine seminal plasma protein and bovine acidic seminal fluid protein (Romero et al., *Nat. Struct. Biol.* 4:783–788, 1997), and *X. laevis* tolloid-like protein (Lin et al., *Dev. Growth Differ.* 39:43–51, 1997). Analysis of the tissue distribution of the mRNA corresponding to this novel DNA showed that expression was widespread in adult human tissues. The polypeptide has been designated "zvegf4" in view of its homology to the VEGFs in the growth factor domain.

Structural predictions based on the zvegf4 sequence and its homology to other growth factors suggests that the polypeptide can form homomultimers or heteromultimers that act on tissues to control organ development by modulating cell proliferation, migration, differentiation, or metabolism. Experimental evidence supports these predictions. Zvegf4 heteromultimers may comprise a polypeptide from another member of the PDGF/VEGF family of proteins, including VEGF, VEGF-B, VEGF-C, VEGF-D, zvegf3, PIGF (Maglione et al., *Proc. Natl. Acad. Sci. USA* 88:9267–9271, 1991), PDGF-A (Murray et al., U.S. Pat. No. 4,899,919; Heldin et al., U.S. Pat. No. 5,219,759), or PDGF-B (Chiu et al., *Cell* 37:123–129, 1984; Johnsson et al., *EMBO J*. 3:921–928, 1984). Members of this family of polypeptides regulate organ development and regeneration, post-developmental organ growth, and organ maintenance, as well as tissue maintenance and repair processes. These factors are also involved in pathological processes where therapeutic treatments are required, including cancer, rheumatoid arthritis, diabetic retinopathy, ischemic limb disease, peripheral vascular disease, myocardial ischemia, vascular intimal hyperplasia, atherosclerosis, and hemangioma formation. To treat these pathological conditions it will often be required to develop compounds to antagonize the members of the PDGF/VEGF family of proteins, or their respective receptors. This may include the development of neutralizing antibodies, small molecule antagonists, modified forms of the growth factors that maintain receptor binding activity but lack receptor activating activity, soluble receptors (including receptor-immunoglobulin fusion proteins) or antisense or ribozyme molecules to block polypeptide production.

A representative human zvegf4 polypeptide sequence is shown in SEQ ID NO:2, and a representative mouse zvegf4 polypeptide sequence is shown in SEQ ID NO:53. DNAs encoding these polypeptides are shown in SEQ ID NOS: 1 and 52, respectively. Analysis of the amino acid sequence shown in SEQ ID NO:2 indicates that residues 1 to 18 form a secretory peptide. The CUB domain extends from residue 52 to residue 179. A propeptide-like sequence extends from residue 180 to either residue 245, residue 249 or residue 257, and includes four potential cleavage sites at its carboxyl terminus, monobasic sites at residue 245 and residue 249, a dibasic site at residues 254–255, and a target site for furin or a furin-like protease at residues 254–257. Protein produced in a baculovirus expression system showed cleavage between residues 250 and 249, as well as longer species with amino termini at residues 19 and 35. The growth factor domain extends from residue 258 to residue 370, and may include additional residues at the N-terminus (for instance, this domain may include residues 250 to 370 or residues 246 to 370). Those skilled in the art will recognize that domain boundaries are somewhat imprecise and can be expected to vary by up to ±5 residues from the specified positions. Cleavage of full-length zvegf4 with plasmin resulted in activation of the zvegf4 polypeptide. By Western analysis, a band migrating at approximately the same size as the growth factor domain was observed. A matched, uncleaved full-length zvegf4 sample demonstrated no activation.

Signal peptide cleavage is predicted to occur in human zvegf4 after residue 18 (±3 residues). Upon comparison of human and mouse zvegf4 sequences, alternative signal peptide cleavage sites are predicted after residue 23 and/or residue 24. This analysis suggests that the zvegf4 polypeptide chain may be cleaved to produce a plurality of monomeric species, some of which are shown in Table 1. In certain host cells, cleavage after Lys-255 is expected to result in subsequent removal of residues 254–255, although polypeptides with a carboxyl terminus at residue 255 may also be prepared. Cleavage after Lys-257 is expected to result in subsequent removal of residue 257. These cleavage sites can be modified to prevent proteolysis and thus provide for the production of uncleaved zvegf4 polypeptides and multimers comprising them. Actual cleavage patterns are expected to vary among host cells.

TABLE 1

| Monomer | Residues (SEQ ID NO:2) |
|---|---|
| Cub domain | 19–179 |
|  | 35–179 |
|  | 52–179 |
| CUB domain + interdomain region | 19–257 |
|  | 35–257 |
|  | 52–257 |
|  | 19–255 |
|  | 35–255 |
|  | 52–255 |
|  | 19–253 |
|  | 35–253 |
|  | 52–253 |
|  | 19–249 |
|  | 35–249 |
|  | 52–249 |
|  | 19–245 |
|  | 35–245 |
|  | 52–245 |
| Cub domain + interdomain region + growth factor domain | 19–370 |
|  | 35–370 |
|  | 52–370 |
| Growth factor domain | 246–370 |
|  | 250–370 |
|  | 258–370 |
| Growth factor domain + interdomain region | 180–370 |

Also included within the present invention are polypeptides that are at least 70%, 80%, 90%, and 95% identical to the polypeptides disclosed in Table 1, wherein these additional polypeptides retain certain characteristic sequence motifs as disclosed below.

Zvegf4 polypeptides are designated herein with a subscript indicating the amino acid residues. For example, the CUB domain polypeptides disclosed in Table 1 are designated "zvegf4$_{19-179}$", "zvegf4$_{35-179}$", and "zvegf4$_{52-179}$".

Higher order structure of zvegf4 polypeptides can be predicted by sequence alignment with known homologs and computer analysis using available software (e.g., the INSIGHT II® viewer and homology modeling tools; MSI, San Diego, Calif.). Analysis of SEQ ID NO:2 predicts that the secondary structure of the growth factor domain is dominated by the cystine knot, which ties together variable beta strand-like regions and loops into a bow tie-like structure. Sequence alignment indicates that Cys residues within the growth factor domain at positions 272, 302, 306, 318, 360, and 362, and Gly 304 are highly conserved within the family. Further analysis suggests pairing (disulfide bond formation) of Cys residues 272 and 318, 302 and 360, and 306 and 362 to form the cystine knot. This arrangement of conserved residues can be represented by the formula CX{18,33}CXGXCX{6,33}CX{20,50}CXC (SEQ ID NO:3), wherein amino acid residues are represented by the conventional single-letter code, X is any amino acid residue, and {y,z} indicates a region of variable residues (X) from y to z residues in length. A consensus bow tie structure is formed as: amino terminus to cystine knot→beta strand-like region 1-variable loop 1→beta strand-like region 2→cystine knot→beta strand-like region 3→variable loop 2→beta strand-like region 4→cystine knot 4→beta strand-like region 5→variable loop 3→beta strand-like region 6→cystine knot. Variable loops 1 and 2 form one side of the bow tie, with variable loop 3 forming the other side. The structure of the zvegf4 growth factor domain appears to diverge from the consensus structure of other family members in loop 2 and beta strand-like regions 3 and 4, wherein all are abbreviated and essentially replaced by a cysteine cluster comprising residues 307 (Gly) through 317 (Thr), which includes Cys residues at positions 308 and 316 of SEQ ID NO:2. The approximate boundaries of the beta strand-like regions in SEQ ID NO:2 are: region 1, residues 273–281; region 2, residues 297–301; region 5, residues 319–324; region 6, residues 355–358. Loops separate regions 1 and 2, and regions 5 and 6.

The CUB domain of zvegf4 is believed to form a beta barrel structure with nine distinct beta strand-like regions. These regions comprise residues 54–57, 61–65, 79–84, 90–95, 97–99, 112–115, 126–130, 146–150, and 163–170 of SEQ ID NO:2. A multiple alignment of CUB domains of *Xenopus laevis* neuropilin precursor (Takagi et al., ibid.), human BMP-1 (Wozney et al., ibid.), and *X. laevis* tolloid-like protein (Lin et al., ibid.) indicates the presence of a conserved motif corresponding to residues 109–131 of SEQ ID NO:2. This motif is represented by the formula C[KR]Y[DNE][WYF]X{11,15}G[KR][WYF]C (SEQ ID NO:4), wherein square brackets indicate the allowable residues at a given position and X{y,z} is as defined above.

The proteins of the present invention include proteins comprising CUB domains homologous to the CUB domain of zvegf4. These homologous domains are from 100 to 120 residues in length and comprise a motif of the sequence C[KR]Y[DNE][WYF]X{11,15}G[KR][WYF]C (SEQ ID NO:4) corresponding to residues 109–131 of SEQ ID NO:2. These homologous CUB domains are at least 70% identical to residues 52–179 of SEQ ID NO:2, at least 80% identical, at least 90% identical, or at least 95% identical to residues 52–179 of SEQ ID NO:2.

CUB domain-containing proteins of the present invention may further include a zvegf4 interdomain region or homolog thereof. The interdomain region is at least 70% identical to residues 180 to 253 of SEQ ID NO:2.

As noted above, residues 254–257 of SEQ ID NO:2 are believed to provide cleavage sites for furin or other proteases. However, polypeptides comprising a C-terminal interdomain region (e.g., zvegf4$_{52-257}$) can be prepared with or without one or more of residues 254–257 at the carboxyl terminus. In addition, polypeptides comprising another C-terminal interdomain region (e.g., zvegf4$_{52-245}$) can be prepared.

Additional proteins of the present invention comprise the zvegf4 growth factor domain or a homolog thereof. These proteins thus comprise a polypeptide segment that is at least 70%, 80%, 90% or 95% identical to residues 258–370 of SEQ ID NO:2, wherein the polypeptide segment comprises Cys residues at positions corresponding to residues 272, 302, 306, 318, 360, and 362 of SEQ ID NO:2; a glycine at a position corresponding to residue 304 of SEQ ID NO:2; and the sequence motif CX{18,33}CXGXCX{6,33}CX{20,50}CXC (SEQ ID NO:3) corresponding to residues 272–362 of SEQ ID NO:2.

Additional proteins comprising combinations of the CUB domain, interdomain region, and growth factor domain are shown above in Table 1. In each case, the invention also includes homologous proteins comprising homologous domains as disclosed above. More particularly, domains or regions in the mouse zvegf4 protein corresponding to domains or regions in the human zvegf4 protein are included within the present invention.

Structural analysis and homology predict that zvegf4 polypeptides complex with a second polypeptide to form multimeric proteins. These proteins include homodimers and heterodimers. In the latter case, the second polypeptide can be a truncated or other variant zvegf4 polypeptide or another polypeptide, such as a PlGF, PDGF-A, PDGF-B, VEGF, VEGF-B, VEGF-C, VEGF-D, or zvegf3 polypeptide. Among the dimeric proteins within the present invention are dimers formed by non-covalent association (e.g., hydrophobic interactions) with a second subunit, either a second zvegf4 polypeptide or other second subunit, or by covalent association stabilized by intermolecular disulfide bonds between cysteine residues of the component monomers. Within SEQ ID NO:2, the Cys residues at positions 296, 308, 316, and 364 may form intramolecular or intermolecular disulfide bonds.

The present invention thus provides a variety of multimeric proteins comprising a zvegf4 polypeptide as disclosed above. These zvegf4 polypeptides include zvegf4$_{19-179}$, zvegf4$_{35-179}$, zvegf4$_{52-179}$, zvegf4$_{19-245}$, zvegf4$_{35-245}$, zvegf4$_{52-245}$, zvegf4$_{19-249}$, zvegf4$_{35-249}$, zvegf4$_{52-249}$, zvegf4$_{19-253}$, zvegf4$_{35-253}$, zvegf4$_{52-253}$, zvegf4$_{19-255}$, zvegf4$_{35-255}$, zvegf4$_{52-255}$, zvegf4$_{19-257}$, zvegf4$_{35-257}$, zvegf4$_{52-257}$, zvegf4$_{19-370}$, zvegf4$_{35-370}$, zvegf4$_{52-370}$, zvegf4$_{246-370}$, zvegf4$_{250-370}$, and zvegf4$_{258-370}$, as well as variants and derivatives of these polypeptides as disclosed herein. These zvegf4 polypeptides can be prepared as homodimers or as heterodimers with corresponding regions of related family members. For example, a zvegf4 CUB domain polypeptide can be dimerized with a polypeptide comprising residues 46–170 of SEQ ID NO:33; a zvegf4 growth factor domain polypeptide can be dimerized with a polypeptide comprising residues 235–345 of SEQ ID NO:33; and a zvegf4 CUB domain-interdomain-growth factor domain polypeptide can be dimerized with a polypeptide comprising residues 46–345 of SEQ ID NO:33.

Percent sequence identity is determined by conventional methods. See, for example, Altschul et al., *Bull. Math. Bio.* 48:603–616, 1986, and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 2 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 2

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |

TABLE 2-continued

|   | A  | R  | N  | D  | C  | Q  | E  | G  | H  | I  | L  | K  | M  | F  | P  | S  | T  | W  | Y | V |
|---|----|----|----|----|----|----|----|----|----|----|----|----|----|----|----|----|----|----|---|---|
| D | -2 | -2 | 1  | 6  |    |    |    |    |    |    |    |    |    |    |    |    |    |    |   |   |
| C | 0  | -3 | -3 | -3 | 9  |    |    |    |    |    |    |    |    |    |    |    |    |    |   |   |
| Q | -1 | 1  | 0  | 0  | -3 | 5  |    |    |    |    |    |    |    |    |    |    |    |    |   |   |
| E | -1 | 0  | 0  | 2  | -4 | 2  | 5  |    |    |    |    |    |    |    |    |    |    |    |   |   |
| G | 0  | -2 | 0  | -1 | -3 | -2 | -2 | 6  |    |    |    |    |    |    |    |    |    |    |   |   |
| H | -2 | 0  | 1  | -1 | -3 | 0  | 0  | -2 | 8  |    |    |    |    |    |    |    |    |    |   |   |
| I | -1 | -3 | -3 | -3 | -1 | -3 | -3 | -4 | -3 | 4  |    |    |    |    |    |    |    |    |   |   |
| L | -1 | -2 | -3 | -4 | -1 | -2 | -3 | -4 | -3 | 2  | 4  |    |    |    |    |    |    |    |   |   |
| K | -1 | 2  | 0  | -1 | -3 | 1  | 1  | -2 | -1 | -3 | -2 | 5  |    |    |    |    |    |    |   |   |
| M | -1 | -1 | -2 | -3 | -1 | 0  | -2 | -3 | -2 | 1  | 2  | -1 | 5  |    |    |    |    |    |   |   |
| F | -2 | -3 | -3 | -3 | -2 | -3 | -3 | -3 | -1 | 0  | 0  | -3 | 0  | 6  |    |    |    |    |   |   |
| P | -1 | -2 | -2 | -1 | -3 | -1 | -1 | -2 | -2 | -3 | -3 | -1 | -2 | -4 | 7  |    |    |    |   |   |
| S | 1  | -1 | 1  | 0  | -1 | 0  | 0  | 0  | -1 | -2 | -2 | 0  | -1 | -2 | -1 | 4  |    |    |   |   |
| T | 0  | -1 | 0  | -1 | -1 | -1 | -1 | -2 | -2 | -1 | -1 | -1 | -1 | -2 | -1 | 1  | 5  |    |   |   |
| W | -3 | -3 | -4 | -4 | -2 | -2 | -3 | -2 | -2 | -3 | -2 | -3 | -1 | 1  | -4 | -3 | -2 | 11 |   |   |
| Y | -2 | -2 | -2 | -3 | -2 | -1 | -2 | -3 | 2  | -1 | -1 | -2 | -1 | 3  | -3 | -2 | -2 | 2  | 7 |   |
| V | 0  | -3 | -3 | -3 | -1 | -2 | -2 | -3 | -3 | 3  | 1  | -2 | 1  | -1 | -2 | -2 | 0  | -3 | -1| 4 |

The level of identity between amino acid sequences can be determined using the "FASTA" similarity search algorithm of Pearson and Lipman (*Proc. Natl. Acad. Sci. USA* 85:2444, 1988) and Pearson (*Meth. Enzymol.* 183:63, 1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, 1990 (ibid.).

FASTA can also be used to determine the sequence identity of nucleic acid molecules using a ratio as disclosed above. For nucleotide sequence comparisons, the ktup value can range between one to six, preferably from four to six.

Within certain embodiments of the invention amino acid substitutions as compared with the amino acid sequence of SEQ ID NO:2 or SEQ ID NO:53 are conservative substitutions. The BLOSUM62 matrix (Table 2) is an amino acid substitution matrix derived from about 2,000 local multiple alignments of protein sequence segments, representing highly conserved regions of more than 500 groups of related proteins (Henikoff and Henikoff, ibid.). Thus, the BLOSUM62 substitution frequencies can be used to define conservative amino acid substitutions that may be introduced into the amino acid sequences of the present invention. As used herein, the term "conservative amino acid substitution" refers to a substitution represented by a BLOSUM62 value of greater than -1. For example, an amino acid substitution is conservative if the substitution is characterized by a BLOSUM62 value of 0, 1, 2, or 3. More conservative amino acid substitutions are characterized by a BLOSUM62 value of at least 1 (e.g., 1, 2 or 3), while still more conservative amino acid substitutions are characterized by a BLOSUM62 value of at least 2 (e.g., 2 or 3).

Polypeptides of the present invention can be prepared with one or more amino acid substitutions, deletions or additions as compared to SEQ ID NO:2 or SEQ ID NO:53. These changes can be of a minor nature, that is conservative amino acid substitutions and other changes that do not significantly affect the folding or activity of the protein or polypeptide, and include amino- or carboxyl-terminal extensions, such as an amino-terminal methionine residue, an amino or carboxyl-terminal cysteine residue to facilitate subsequent linking to maleimide-activated keyhole limpet hemocyanin, a small linker peptide of up to about 20–25 residues, or an affinity tag as disclosed above.

Two or more affinity tags may be used in combination. Polypeptides comprising affinity tags can further comprise a polypeptide linker and/or a proteolytic cleavage site between the zvegf4 polypeptide and the affinity tag. Exemplary cleavage sites include, without limitation, thrombin cleavage sites and factor Xa cleavage sites.

The present invention further provides a variety of other polypeptide fusions and related multimeric proteins comprising one or more polypeptide fusions. For example, a zvegf4 polypeptide can be prepared as a fusion to a dimerizing protein as disclosed in U.S. Pat. Nos. 5,155,027 and 5,567,584. Exemplary dimerizing proteins in this regard include immunoglobulin constant region domains. Dimerization can also be stabilized by fusing a zvegf4 polypeptide to a leucine zipper sequence (Riley et al., *Protein Eng.* 9:223–230, 1996; Mohamed et al., *J. Steroid Biochem. Mol. Biol.* 51:241–250, 1994). Immunoglobulin-zvegf4 polypeptide fusions and leucine zipper fusions can be expressed in genetically engineered cells to produce a variety of multimeric zvegf4 analogs. Auxiliary domains can be fused to zvegf4 polypeptides to target them to specific cells, tissues, or macromolecules (e.g., collagen). For example, a zvegf4 polypeptide or protein can be targeted to a predetermined cell type by fusing a zvegf4 polypeptide to a ligand that specifically binds to a receptor on the surface of the target cell. In this way, polypeptides and proteins can be targeted for therapeutic or diagnostic purposes. A zvegf4 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

Zvegf4 polypeptide fusions will generally contain not more than about 1,500 amino acid residues, often not more than about 1,200 residues, more often not more than about 1,000 residues, and will in many cases be considerably smaller. For example, a zvegf4 polypeptide of 352 residues (residues 19–370 of SEQ ID NO:2) can be fused to *E. coli* β-galactosidase (1,021 residues; see Casadaban et al., *J. Bacteriol.* 143:971–980, 1980), a 10-residue spacer, and a 4-residue factor Xa cleavage site to yield a polypeptide of 1,387 residues. In a second example, residues 250–370 of SEQ ID NO:2 can be fused to maltose binding protein (approximately 370 residues), a 4-residue cleavage site, and a 6-residue polyhistidine tag.

A polypeptide comprising the zvegf4 growth factor domain (e.g., $zvegf4_{258-370}$ or $zvegf4_{180-370}$) may be fused to a non-zvegf4 CUB domain. Within a related embodiment of the invention, a zvegf4 polypeptide comprising zvegf4 growth factor and CUB domains is fused to a non-zvegf4 CUB domain, such as a CUB-domain-comprising neuropilin polypeptide.

The present invention further provides polypeptide fusions comprising the zvegf4 CUB domain (e.g., $zvegf4_{52-179}$). The CUB domain, with its homology to neuropilin-1, may be used to target zvegf4 or other proteins containing it to cells having cell-surface semaphorins, including endothelial cells, neuronal cells, lymphocytes, and tumor cells. The zvegf4 CUB domain can thus be joined to other moieties, including polypeptides (e.g., other growth factors, antibodies, and enzymes) and non-peptidic moieties (e.g., radionuclides, contrast agents, and the like), to target them to cells expressing cell-surface semaphorins. The cleavage sites between the CUB and growth factor domains of zvegf4 may allow for proteolytic release of the growth factor domain or other moiety through existing local proteases within tissues, or by proteases added from exogenous sources. The release of the targeted moiety may provide more localized biological effects.

The polypeptide fusions of the present invention further include fusions between zvegf4 and zvegf3, wherein a domain of zvegf4 is replaced with the corresponding domain of zvegf3 or a variant thereof. A representative human zvegf3 polypeptide sequence is shown in SEQ ID NO:33, and a representative mouse sequence is shown in SEQ ID NO:35. Within SEQ ID NO:33, the CUB domain comprises residues 46–170, the interdomain region comprises residues 171–234, and the growth factor domain comprises residues 235–345 (all ±5 residues). A secretory peptide is predicted to be cleaved from the polypeptide after residue 14 (±3 residues). Cleavage sites are predicted at residue 249, residues 254–255, and residues 254–257. Domain boundaries in mouse zvegf3 and other orthologous sequences can be determined readily by those of ordinary skill in the art by alignment with the human sequence disclosed herein. Of particular interest are fusions in which the zvegf3 CUB domain is combined with the zvegf4 growth factor domain, and fusions in which the zvegf4 CUB domain is combined with the zvegf3 growth factor domain. Within these polypeptide fusions the interdomain region may be derived from either zvegf3 or zvegf4. Polypeptide fusions comprising zvegf3 and zvegf4 sequences include both full-length and truncated sequences, for example sequences analogous to those disclosed in Table 1, above.

Proteins comprising the wild-type zvegf4 CUB domain and variants thereof may be used to modulate activities mediated by cell-surface semaphorins. While not wishing to be bound by theory, zvegf4 may bind to semaphorins via its CUB domain. The observation that semaphorin III is involved in vascular development suggests that members of the vascular growth factor family of proteins may also be involved, especially due to the co-binding activity of VEGF and semaphorin III to neuropilin-1. Zvegf4 may thus be used to design agonists and antagonist of neuropilin-semaphorin interactions. For example, the zvegf4 sequence disclosed herein provides a starting point for the design of molecules that antagonize semaphorin-stimulated activities, including neurite growth, cardiovascular development, cartilage and limb development, and T and B-cell function. Additional applications include intervention in various pathologies, including rheumatoid arthritis, various forms of cancer, autoimmune disease, inflammation, retinopathies, hemangiomas, ischemic events within tissues including the heart, kidney and peripheral arteries, neuropathies, acute nerve damage, and diseases of the central and peripheral nervous systems, including stroke.

The isolated CUB domain of either mouse or human zvegf4 (and multimers thereof) may also be useful to block binding of other zvegf4 molecules (e.g., full-length polypeptide, isolated growth factor domain, or multimers thereof) to cell-surface molecules and/or extracellular binding sites by itself binding to such molecules or sites. In addition, the isolated CUB domain of either mouse or human zvegf4 may be useful to block zvegf4 binding, and/or more generally vascular endothelial growth factor binding, to neuropilin-1 (see M. L. Gagnon et al., *Proc. Natl. Acad. Sci. USA* 97:2573–78, 2000). Further, the second major loop of zvegf4 (residues 308–316) may represent the receptor-binding loop of zvegf4 (see, for instance, WO 99/13329; WO 98/10795; and W. J. LaRochelle et al., *J. Biol. Chem.* 267:17074–77, 1992), and thus may be useful as an antagonist of zvegf4 activity. Within this peptide (zvegf4 residues 308–316), Cys308 and Cys316 may or may not be disulfide bonded. Also, dimers of this peptide may be constructed such that residue Cys308 is disulfide bonded to either Cys308 or Cys316 of the homodimer partner peptide.

Amino acid sequence changes are made in zvegf4 polypeptides so as to minimize disruption of higher order structure essential to biological activity. As noted above, conservative amino acid changes are generally less likely to negate activity than are non-conservative changes. Changes in amino acid residues will be made so as not to disrupt the cystine knot and "bow tie" arrangement of loops in the growth factor domain that is characteristic of the protein family. Conserved motifs will also be maintained. The effects of amino acid sequence changes can be predicted by computer modeling as disclosed above or determined by analysis of crystal structure (see, e.g., Lapthom et al., ibid.). A hydrophilicity profile of SEQ ID NO:2 is shown in FIGS. 1A–1G. Those skilled in the art will recognize that this hydrophilicity will be taken into account when designing alterations in the amino acid sequence of a zvegf4 polypeptide, so as not to disrupt the overall profile. Additional guidance in selecting amino acid subsitutions is provided by a comparison of the mouse (SEQ ID NO:53) and human (SEQ ID NO:2) zvegf4 sequences. The amino acid sequence is highly conserved between mouse and human zvegf4s, with an overall amino acid sequence identity of 85.1%.

The polypeptides of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in *Xenopus oocytes* by microinjection of mutated mRNA and chemically aminoacylated suppressor tRNAs (Turcatti et al., *J. Biol. Chem.* 271:19991–19998, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

Essential amino acids in the polypeptides of the present invention can be identified according to procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88:4498–4502, 1991). In the latter technique, single alanine mutations are introduced at every residue in the molecule, and the resultant mutant molecules are tested for biological activity of other properties to identify amino acid residues that are critical to the activity of the molecule.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zvegf4 DNA and polypeptide sequences can be generated through DNA shuffling as disclosed by Stemmer, *Nature* 370:389–391, 1994 and Stemmer, *Proc. Natl. Acad. Sci. USA* 91:10747–10751, 1994. Briefly, variant genes are generated by in vitro homologous recombination by random fragmentation of a parent gene followed by reassembly using PCR, resulting in randomly introduced point mutations. This technique can be modified by using a family of parent genes, such as allelic variants or genes from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high volume or high-throughput screening methods to detect biological activity of zvegf4 variant polypeptides, in particular biological activity in modulating cell proliferation or cell differentiation. For example, mitogenesis assays that measure dye incorporation or $^3$H-thymidine incorporation can be carried out on large numbers of samples, as can cell-based assays that detect expression of a reporter gene (e.g., a luciferase gene).

Mutagenesis of the CUB domain can be used to modulate its binding to members of the semaphorin family, including enhancing or inhibiting binding to selected family members. A modified spectrum of binding activity may be desirable for optimizing therapeutic and/or diagnostic utility of proteins comprising a zvegf4 CUB domain. Direct binding utilizing labeled CUB protein can be used to monitor changes in CUB domain binding activity to selected semaphorin family members. Semaphorins of interest in this regard include isolated proteins, proteins present in cell membranes, and proteins present on cell-surfaces. The CUB domain can be labeled by a variety of methods including radiolabeling with isotopes, such as $^{125}$I, conjugation to enzymes such as alkaline phosphatase or horseradish peroxidase, conjugation with biotin, and conjugation with various fluorescent markers including FITC. These and other assays are disclosed in more detail below. Mutagenized DNA molecules that encode active zvegf4 polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of polypeptides that are homologous to the zvegf4 polypeptides disclosed above in Table 1 and retain the biological properties of the wild-type protein. Such polypeptides can also include additional polypeptide segments as generally disclosed above.

The present invention also provides polynucleotide molecules, including DNA and RNA molecules, that encode the zvegf4 polypeptides disclosed above. The polynucleotides of the present invention include the sense strand; the anti-sense strand; and the DNA as double-stranded, having both the sense and anti-sense strands annealed together by hydrogen bonds. A representative DNA sequence encoding human zvegf4 polypeptides is set forth in SEQ ID NO:1, and a representative DNA sequence encoding mouse zvegf4 polypeptides is set forth in SEQ ID NO:52. Additional DNA sequences encoding zvegf4 polypeptides can be readily generated by those of ordinary skill in the art based on the genetic code. Counterpart RNA sequences can be generated by substitution of U for T.

Those skilled in the art will readily recognize that, in view of the degeneracy of the genetic code, considerable sequence variation is possible among polynucleotide molecules encoding zvegf4 polypeptides. SEQ ID NO:6 is a degenerate DNA sequence that encompasses all DNAs that encode the zvegf4 polypeptide of SEQ ID NO: 2. Those skilled in the art will recognize that the degenerate sequence of SEQ ID NO:6 also provides all RNA sequences encoding SEQ ID NO:2 by substituting U for T. Thus, zvegf4 polypeptide-encoding polynucleotides comprising nucleotides 1–1110, 1–537, 55–537, 103–537, 154–537, 55–771, 103–771, 154–771, 55–765, 103–765, 154–765, 55–759, 103–759, 154–759, 55–747, 103–747, 154–747, 55–735, 103–735, 154–735, 55–1110, 103–1110, 154–1110, 772–1110, 748–1110, 736–1110, and 538–1110 of SEQ ID NO:6 and their RNA equivalents are contemplated by the present invention. Table 3 sets forth the one-letter codes used within SEQ ID NO:6 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 3

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:6, encompassing all possible codons for a given amino acid, are set forth in Table 4, below.

TABLE 4

| Amino Acid | One-Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | CAN |
| Pro | P | CCA CCC CCG CCT | CCN |
| Ala | A | GCA GCC GCG GCT | GCN |
| Gly | G | GGA GGC GCG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | — | TAA TAG TGA | TRR |
| Asn\|Asp | B | | RAY |

TABLE 4-continued

| Amino Acid | One-Letter Code | Codons | Degenerate Codon |
|---|---|---|---|
| Glu\|Gln | Z | | SAR |
| Any | X | | NNN |
| Gap | — | — | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequences may encode variant amino acid sequences, but one of ordinary skill in the art can easily identify such variant sequences by reference to the amino acid sequence of SEQ ID NO: 2 and of SEQ ID NO:53. Variant sequences can be readily tested for functionality as described herein.

Within certain embodiments of the invention the isolated polynucleotides will hybridize to similar sized regions of SEQ ID NO:1 or SEQ ID NO:52, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. Complementary DNA (cDNA) clones are prepared from RNA that is isolated from a tissue or cell that produces large amounts of zvegf4 RNA. Such tissues and cells are identified by Northern blotting (Thomas, *Proc. Natl. Acad. Sci. USA* 77:5201, 1980), and include heart, pancreas, stomach, and adrenal gland. Total RNA can be prepared using guanidine HCl extraction followed by isolation by centrifugation in a CsCl gradient (Chirgwin et al., *Biochemistry* 18:52–94, 1979). Poly (A)+ RNA is prepared from total RNA using the method of Aviv and Leder (*Proc. Natl. Acad. Sci. USA* 69:1408–1412, 1972). Complementary DNA (cDNA) is prepared from poly(A)+ RNA using known methods. In the alternative, genomic DNA can be isolated. For some applications (e.g., expression in transgenic animals) it may be advantageous to use a genomic clone, or to modify a cDNA clone to include at least one genomic intron. Methods for identifying and isolating cDNA and genomic clones are well known and within the level of ordinary skill in the art, and include the use of the sequence disclosed herein, or parts thereof, for probing or priming a library. Polynucleotides encoding zvegf4 polypeptides are identified and isolated by, for example, hybridization or polymerase chain reaction ("PCR", Mullis, U.S. Pat. No. 4,683,202). Expression libraries can be probed with antibodies to zvegf4, receptor fragments, or other specific binding partners.

Those skilled in the art will recognize that the sequences disclosed in SEQ ID NOS:1 and 2 represent a single allele of human zvegf4, and that the sequences disclosed in SEQ ID NOS:52 and 53 represent a single allele of mouse zvegf4. Allelic variants of these sequences can be cloned by probing cDNA or genomic libraries from different individuals according to standard procedures. Alternatively spliced forms of zvegf4 are also expected to exist.

The zvegf4 polynucleotide sequence disclosed herein can be used to isolate polynucleotides encoding other zvegf4 proteins. Such other polynucleotides include allelic variants, alternatively spliced cDNAs and counterpart polynucleotides from other species (orthologs). These orthologous polynucleotides can be used, inter alia, to prepare the respective orthologous proteins. Other species of interest include, but are not limited to, mammalian, avian, amphibian, reptile, fish, insect and other vertebrate and invertebrate species. Of particular interest are zvegf4 polynucleotides and proteins from other mammalian species, including non-human primate, murine, porcine, ovine, bovine, canine, feline, and equine polynucleotides and proteins. Orthologs of human zvegf4 can be cloned using information and compositions provided by the present invention in combination with conventional cloning techniques. For example, a cDNA can be cloned using mRNA obtained from a tissue or cell type that expresses zvegf4 as disclosed herein. Suitable sources of mRNA can be identified by probing Northern blots with probes designed from the sequences disclosed herein. A library is then prepared from mRNA of a positive tissue or cell line. A zvegf4-encoding cDNA can then be isolated by a variety of methods, such as by probing with a complete or partial human cDNA or with one or more sets of degenerate probes based on the disclosed sequences. Hybridization will generally be done under low stringency conditions, wherein washing is carried out in 1×SSC with an initial wash at 40° C. and with subsequent washes at 5° C. higher intervals until background is suitably reduced. A cDNA can also be cloned using the polymerase chain reaction, or PCR (Mullis, U.S. Pat. No. 4,683,202), using primers designed from the representative human zvegf4 sequence disclosed herein. Within an additional method, the cDNA library can be used to transform or transfect host cells, and expression of the cDNA of interest can be detected with an antibody to zvegf4 polypeptide. Similar techniques can also be applied to the isolation of genomic clones.

For any zvegf4 polypeptide, including variants and fusion proteins, one of ordinary skill in the art can readily generate a fully degenerate polynucleotide sequence encoding that variant using the information set forth in Tables 3 and 4, above.

Conserved regions of zvegf4, identified by alignment with sequences of other family members, can be used to identify related polynucleotides and proteins. For instance, reverse transcription-polymerase chain reaction (RT-PCR) and other techniques known in the art can be used to amplify sequences encoding the conserved motifs present in zvegf4 from RNA obtained from a variety of tissue sources. In particular, highly degenerate primers as shown below in Table 5 (designed from an alignment of zvegf4 with PDGF A and B chains, VEGF, VEGF-B, VEGF-C, VEGF-D, and zvegf3) are useful for cloning polynucleotides encoding homologous growth factor domains. Primers shown in Table 6, designed from an alignment of zvegf4 with X. laevis neuropilin precursor, human BMP-1, human zvegf3, and X. laevis tolloid-like protein, are useful for cloning polynucleotides encoding CUB domains. The primers of Tables 5 and 6 can thus be used to obtain additional polynucleotides encoding homologs of the zvegf4 sequence of SEQ ID NO:1 and NO:2.

TABLE 5

```
zvegf4 residues 301-305
degenerate: MGN TGY GGN GGN AAY TG   (SEQ ID NO:7)
consensus:  MGN TGY DSN GGN WRY TG   (SEQ ID NO:8)
complement: CAR YWN CCN SHR CAN CK   (SEQ ID NO:9)
zvegf4 residues 292-297
degenerate: TTY TTY CCN MGN TGY YT   (SEQ ID NO:10)
consensus:  NTN DDN CCN NSN TGY BT   (SEQ ID NO:11)
complement: AVR CAN SNN GGN HHN AN   (SEQ ID NO:12)
zvegf4 residues 357-362
degenerate  CAY GAR MGN TGY GAY TG   (SEQ ID NO:13)
consensus:  CAY NNN NVN TGY VVN TG   (SEQ ID NO:14)
complement: CAN BBR CAN BNN NNR TG   (SEQ ID NO:15)
zvegf4 residues 250-255
degenerate: TGY ACN CCN MGN AAY TA   (SEQ ID NO:16)
consensus:  TGY HNN MCN MKN RMN DH   (SEQ ID NO:17)
complement: DHN KYN MKN GKN NDR CA   (SEQ ID NO:18)
```

TABLE 6

```
zvegf4 residues 110-115
consensus:  N TAY GAY TWY GTN GAR GT  (SEQ ID NO:19)
complement: N ATR CTR AWR CAN CTY CA  (SEQ ID NO:20)
zvegf4 residues 68-73
consensus:  GN TDB CCN MAN DVN TAY C  (SEQ ID NO:21)
complement: CN AHV GGN KTN HBN ATR G  (SEQ ID NO:22)
zvegf4 residues 126-131
consensus:  TN HDN GGN MRN TDB TGY G  (SEQ ID NO:23)
complement: AN DHN CCN KYN AHV ACR C  (SEQ ID NO:24)
```

Zvegf4 polynucleotide sequences disclosed herein can also be used as probes or primers to clone 5' non-coding regions of a zvegf4 gene, including promoter sequences. A human zvegf4 genomic fragment, comprising 5' non-coding and coding sequences, is shown in SEQ ID NO:36. These flanking sequences can be used to direct the expression of zvegf4 and other recombinant proteins. In addition, 5' flanking sequences can be used as targeting sites for regulatory constructs to activate or increase expression of endogenous zvegf4 genes as disclosed by Treco et al., U.S. Pat. No. 5,641,670. A human zvegf4 genomic sequence comprising 5' non-coding sequence and approximately 100 nucleotides of coding sequence is shown in SEQ ID NO:36.

The polynucleotides of the present invention can also be prepared by automated synthesis. The production of short, double-stranded segments (60 to 80 bp) is technically straightforward and can be accomplished by synthesizing the complementary strands and then annealing them. Longer segments (typically >300 bp) are assembled in modular form from single-stranded fragments that are from 20 to 100 nucleotides in length. Automated synthesis of polynucleotides is within the level of ordinary skill in the art, and suitable equipment and reagents are available from commercial suppliers. See, in general, Glick and Pasternak, *Molecular Biotechnology, Principles & Applications of Recombinant DNA*, ASM Press, Washington, D.C., 1994; Itakura et al., *Ann. Rev. Biochem.* 53: 323–56, 1984; and Climie et al., *Proc. Natl. Acad. Sci. USA* 87:633–7, 1990.

The polypeptides of the present invention, including full-length polypeptides, biologically active fragments, and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells, including cultured cells of multicellular organisms. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, Green and Wiley and Sons, NY, 1993.

In general, a DNA sequence encoding a zvegf4 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors, and other elements is a matter of routine design within the level of ordinary skill in the art. Many such elements are described in the literature and are available through commercial suppliers.

To direct a zvegf4 polypeptide into the secretory pathway of a host cell, a secretory signal sequence (also known as a leader sequence, prepro sequence or pre sequence) is provided in the expression vector. The secretory signal sequence may be that of zvegf4, or may be derived from another secreted protein (e.g., t-PA; see, U.S. Pat. No. 5,641,655) or synthesized de novo. The secretory signal sequence is operably linked to the zvegf4 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Expression of zvegf4 polypeptides via a host cell secretory pathway is expected to result in the production of multimeric proteins. As noted above, such multimers include both homomultimers and heteromultimers, the latter including proteins comprising only zvegf4 polypeptides and proteins including zvegf4 and heterologous polypeptides. For example, a heteromultimer comprising a zvegf4 polypeptide and a polypeptide from a related family member (e.g., VEGF, VEGF-B, VEGF-C, VEGF-D, zvegf3, PlGF, PDGF-A, or PDGF-B) can be produced by co-expression of the two polypeptides in a host cell. Sequences encoding these other family members are known. See, for example, Dvorak et al, ibid.; Olofsson et al, ibid.; Hayward et al., ibid.; Joukov et al., ibid.; Oliviero et al., ibid.; Achen et al., ibid.; Maglione et al., ibid.; Heldin et al., U.S. Pat. No. 5,219,759; and Johnsson et al., ibid. If a mixture of proteins results from expression, individual species are isolated by conventional methods. Monomers, dimers, and higher order multimers are separated by, for example, size exclusion chromatography. Heteromultimers can be separated from homomultimers by conventional chromatography or by immunoaffinity chromatography using antibodies specific for individual dimers or by sequential immunoaffinity steps using antibodies specific for individual component polypeptides. See, in general, U.S. Pat. No. 5,094,941.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter. Expression vectors for use in mammalian cells include pZP-1 and pZP-9, which have been deposited with the American Type Culture Collection, 10801 University Blvd., Manassas, Va. USA under accession numbers 98669 and 98668, respectively.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci.* (Bangalore) 11:47–58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See, King and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and Richardson, Ed., *Baculovirus Expression Protocols. Methods in Molecular Biology*, Humana Press, Totowa, N.J., 1995. Recombinant baculovirus can also be produced through the use of a transposon-based system described by Luckow et al. (*J.*

Virol. 67:4566–4579, 1993). This system, which utilizes transfer vectors, is commercially available in kit form (Bac-to-Bac™ kit; Life Technologies, Rockville, Md.). The transfer vector (e.g., pFastBac1™; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971–976, 1990; Bonning et al., *J. Gen. Virol.* 75:1551–1556, 1994; and Chazenbalk and Rapoport, *J. Biol. Chem.* 270:1543–1549, 1995. In addition, transfer vectors can include an in-frame fusion with DNA encoding a polypeptide extension or affinity tag as disclosed above. Using techniques known in the art, a transfer vector containing a zvegf4-encoding sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses zvegf4 protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., High Five™ cells; Invitrogen, Carlsbad, Calif.). See, in general, Glick and Pasternak, *Molecular Biotechnology: Principles and Applications of Recombinant DNA*, ASM Press, Washington, D.C., 1994. See also, U.S. Pat. No. 5,300,435. Serum-free media are used to grow and maintain the cells. Suitable media formulations are known in the art and can be obtained from commercial suppliers. The cells are grown up from an inoculation density of approximately $2-5\times10^5$ cells to a density of $1-2\times10^6$ cells, at which time a recombinant viral stock is added at a multiplicity of infection (MOI) of 0.1 to 10, more typically near 3. Procedures used are generally described in available laboratory manuals (e.g., King and Possee, ibid.; O'Reilly et al., ibid.; Richardson, ibid.).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986; Cregg, U.S. Pat. No. 4,882,279; and Raymond et al., *Yeast* 14 11–23, 1998. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533. Production of recombinant proteins in *Pichia methanolica* is disclosed in U.S. Pat. Nos. 5,716,808, 5,736,383, 5,854,039, and 5,888,768.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zvegf4 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells, for example, are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors.

Zvegf4 polypeptides or fragments thereof can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989.

Covalent, multimeric complexes can also be made by isolating the desired component polypeptides and combining them in vitro. Covalent complexes that can be prepared in this manner include homodimers of zvegf4 polypeptides, heterodimers of two different zvegf4 polypeptides, and heterodimers of a zvegf4 polypeptide and a polypeptide from another family member of the VEGF/PDGF family of proteins. The two polypeptides are mixed together under denaturing and reducing conditions, followed by renaturation of the proteins by removal of the denaturants. Removal can be done by, for example, dialysis or size exclusion chromatography to provide for buffer exchange. When combining two different polypeptides, the resulting renatured proteins may form homodimers of the individual components as well as heterodimers of the two polypeptide components. See, Cao et al., *J. Biol. Chem.* 271:3154–3162, 1996.

Non-covalent complexes comprising a zvegf4 polypeptide can be prepared by incubating a zvegf4 polypeptide and a second polypeptide (e.g., a zvegf4 polypeptide or another peptide of the PDGF/VEGF family) at near-physiological pH. In a typical reaction, polypeptides at a concentration of about 0.1–0.5 µg/µl are incubated at pH≈7.4 in a weak buffer (e.g., 0.01 M phosphate or acetate buffer); sodium chloride may be included at a concentration of about 0.1 M. At 37° C. the reaction is essentially complete with 4–24 hours. See, for example, Weintraub et al., *Endocrinology* 101:225–235, 1997.

Depending upon the intended use, the polypeptides and proteins of the present invention can be purified to ≧80% purity, ≧90% purity, ≧95% purity, or to a pharmaceutically pure state, that is greater than 99.9% pure with respect to contaminating macromolecules, particularly other proteins and nucleic acids, and free of infectious and pyrogenic agents.

Zvegf4 proteins (including chimeric polypeptides and polypeptide multimers) can be purified using fractionation and/or conventional purification methods and media, such as by a combination of chromatographic techniques. See, in general, *Affinity Chromatograhy: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel or cobalt chelate resin. See, for example, Houchuli et al., *Bio/Technol.* 6: 1321–1325, 1988. Proteins comprising a Glu-Glu tag can be purified by immunoaffinity chromatography according to conventional procedures. See, for example, Grussenmeyer et al., ibid. Maltose binding protein fusions are purified on an amylose column according to methods known in the art.

Using methods known in the art, zvegf4 proteins can be prepared as monomers or multimers, glycosylated or non-glycosylated, pegylated or non-pegylated, and may or may not include an initial methionine amino acid residue.

The invention further provides polypeptides that comprise an epitope-bearing portion of a protein as shown in SEQ ID NO:2. An "epitope" is a region of a protein to which an antibody can bind. See, for example, Geysen et al., *Proc. Natl. Acad. Sci. USA* 81:3998–4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660–666, 1983. Antibodies that recognize short, linear epitopes are particularly useful in analytic and diagnostic applications that employ denatured protein, such as Western blotting (Tobin, *Proc. Natl. Acad. Sci. USA* 76:4350–4356, 1979). Anti-peptide antibodies are not conformation-dependent and can be used to detect proteins in fragmented or otherwise altered forms (Niman et al., *Proc. Natl. Acad. Sci. USA* 82:7924–7928, 1985), such as might occur in body fluids or cell culture media. Antibodies to short peptides may also recognize proteins in native conformation and will thus be useful for monitoring protein expression and protein isolation, and in detecting zvegf4 proteins in solution, such as by ELISA or in immunoprecipitation studies.

Antigenic, epitope-bearing polypeptides of the present invention are useful for raising antibodies, including monoclonal antibodies, that specifically bind to a zvegf4 protein. Antigenic, epitope-bearing polypeptides contain a sequence of at least six, within other embodiments at least nine, within other embodiments from 15 to about 30 contiguous amino acid residues of a zvegf4 protein (e.g., SEQ ID NO:2). Polypeptides comprising a larger portion of a zvegf4 protein, i.e., from 30 to 50 or 100 residues or up to the entire sequence are included. It is preferred that the amino acid sequence of the epitope-bearing polypeptide is selected to provide substantial solubility in aqueous solvents, that is the sequence includes relatively hydrophilic residues, and hydrophobic residues are substantially avoided. Such regions of SEQ ID NO:2 include, for example, residues 39–44, 252–257, 102–107, 264–269, and 339–344. Exemplary longer peptide immunogens include peptides comprising residues (i) 131–148, (ii) 230–253, or (iii) 333–355 of SEQ ID NO:2. Peptide (ii) can be prepared with an additional C-terminal cys residue and peptide (iii) with an additional N-terminal cys residue to facilitate coupling.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Monoclonal antibodies can also be produced in mice that have been genetically altered to produce antibodies that have a human structure.

Methods for preparing and isolating polyclonal and monoclonal antibodies are well known in the art. See, for example, Cooligan, et al. (eds.), *Current Protocols in Immunology*, National Institutes of Health, John Wiley and Sons, Inc., 1995; Sambrook et al., *Molecular Cloning: A Laboratory Manual*, second edition, Cold Spring Harbor, N.Y., 1989; and Hurrell, J. G. R. (ed.), *Monoclonal Hybridoma Antibodies: Techniques and Applications*, CRC Press, Inc., Boca Raton, Fla., 1982. As would be evident to one of ordinary skill in the art, polyclonal antibodies can be generated from inoculating a variety of warm-blooded animals such as horses, cows, goats, sheep, dogs, chickens, rabbits, mice, and rats with a zvegf4 polypeptide or a fragment thereof. The immunogenicity of a zvegf4 polypeptide may be increased through the use of an adjuvant, such as alum (aluminum hydroxide) or Freund's complete or incomplete adjuvant. Polypeptides useful for immunization also include fusion polypeptides, such as fusions of zvegf4 or a portion thereof with an immunoglobulin polypeptide or with maltose binding protein. If the polypeptide portion is "hapten-like", such portion may be advantageously joined or linked to a macromolecular carrier (such as keyhole limpet hemocyanin (KLH), bovine serum albumin (BSA), or tetanus toxoid) for immunization.

Alternative techniques for generating or selecting antibodies useful herein include in vitro exposure of lymphocytes to zvegf4 protein or peptide, and selection of antibody display libraries in phage or similar vectors (for instance, through use of immobilized or labeled zvegf4 protein or peptide). Genes encoding polypeptides having potential zvegf4 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides that interact with a known target, which can be a protein or polypeptide, such as a ligand or receptor, a biological or synthetic macromolecule, or organic or inorganic substance. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484; and Ladner et al., U.S. Pat. No. 5,571,698), and random peptide display libraries and kits for screening such libraries are available commercially, for instance from Clontech Laboratories (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the zvegf4 sequences disclosed herein to identify proteins which bind to zvegf4. These "binding proteins", which interact with zvegf4 polypeptides, can be used for tagging cells or for isolating homologous polypeptides by affinity purification, or they can be directly or indirectly conjugated to drugs, toxins, radionuclides, and the like. Binding proteins can also be used in analytical methods, such as for screening expression libraries and for neutralizing zvegf4 activity; for diagnostic assays for determining circulating levels of polypeptides; for detecting or quantitating soluble polypeptides as marker of underlying pathology or disease; and as zvegf4 antagonists to block zvegf4 binding and signal transduction in vitro and in vivo.

Antibodies are determined to be specifically binding if they bind to a zvegf4 polypeptide, peptide or epitope with an affinity at least 10-fold greater than the binding affinity to control (non-zvegf4) polypeptide or protein. In this regard, a "non-zvegf4 polypeptide" includes the related molecules VEGF, VEGF-B, VEGF-C, VEGF-D, zvegf3, PlGF, PDGF-A, and PDGF-B, but excludes zvegf4 polypeptides from non-human species. Due to the high level of amino acid sequence identity expected between zvegf4 orthologs, antibodies specific for human zvegf4 may also bind to zvegf4 from other species. The binding affinity of an antibody can be readily determined by one of ordinary skill in the art, for example, by Scatchard analysis (Scatchard, G., *Ann. NY Acad. Sci.* 51: 660–672, 1949). Methods for screening and isolating specific antibodies are well known in the art. See, for example, Paul (ed.), *Fundamental Immunology*, Raven Press, 1993; Getzoff et al., *Adv. in Immunol.* 43:1–98, 1988; Goding, J. W. (ed.), *Monoclonal Antibodies: Principles and Practice*, Academic Press Ltd., 1996; Benjamin et al., *Ann. Rev. Immunol.* 2:67–101, 1984.

A variety of assays known to those skilled in the art can be utilized to detect antibodies which specifically bind to zvegf4 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant zvegf4 protein or polypeptide.

Of particular interest are neutralizing antibodies, that is antibodies that block zvegf4 biological activity. Within the present invention, an antibody is considered to be neutralizing if the antibody blocks at least 50% of the biological activity of a zvegf4 protein when the antibody is present in a 1000-fold molar excess. Within certain embodiments of the invention the antibody will neutralize 50% of biological activity when present in a 100-fold molar excess or in a 10-fold molar excess. Within other embodiments the antibody neutralizes at least 60% of zvegf4 activity, at least 70% of zvegf4 activity, at least 80% of zvegf4 activity, or at least 90% of zvegf4 activity.

Antibodies to zvegf4 may be used for tagging cells that express zvegf4; for isolating zvegf4 by affinity purification; for diagnostic assays for determining circulating levels of zvegf4 polypeptides; for detecting or quantitating soluble zvegf4 as a marker of underlying pathology or disease; in analytical methods employing FACS; for screening expression libraries; for generating anti-idiotypic antibodies; and as neutralizing antibodies or as antagonists to block zvegf4 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies may also be directly or indirectly conjugated to drugs, toxins, radionuclides and the like, and these conjugates used for in vivo diagnostic or therapeutic applications. Moreover, antibodies to zvegf4 or fragments thereof may be used in vitro to detect denatured zvegf4 or fragments thereof in assays, for example, Western Blots or other assays known in the art. Antibodies can also be used to target an attached therapeutic or diagnostic moiety to cells expressing zvegf4 or receptors for zvegf4. Experimental data suggest that zvegf4 may bind PDGF alpha and/or beta receptors.

Anti-zvegf4 antibodies may be administered to recipients that would benefit from a decrease in bone proliferation or differentiation, such as those recipients suffering from osteosarcoma or osteopetrosis. In animals overexpressing zvegf4, histological analysis showed proliferation of endosteal bone (particularly in trabecular bone) that in some instances replaced most of the bone marrow, as well a proliferation of stromal cells in bone. Anti-zvegf4 antibodies would interfere with these processes, and/or would diminish osteoblast proliferation and bone growth stimulation. Anti-zvegf4 antibodies may also be used to antagonize production of cartilage by interfering with the ability of zvegf4 to stimulate the development or proliferation of chondrocytes.

In addition, anti-zvegf4 antibodies may be used to diminish pro-fibrotic responses. Histological analysis of animals overexpressing zvegf4 detected pro-fibrotic responses in certain organs, particularly liver, kidney and lung. Several diseases or conditions involve fibrosis in liver, lung and kidney. More particularly, alcoholism and viral hepatitis generally involve liver fibrosis, which is often a precursor to cirrhosis, which in turn may lead to an irreversible state of liver failure. Lung fibrosis resulting from exposure to environmental agents (e.g., asbestosis, silicosis) will often manifest as alveolitis or interstitial inflammation. Also, lung fibrosis may occur as a side effect of some cancer therapies, such as ionizing radiation or chemotherpeutic agents. Further, collagen vascular diseases, such as scleroderma and lupus, may also lead to lung fibrosis. In the kidney, the human condition of membranoproliferative glomerulonephritis may correspond to the pro-fibrotic response observed in animals overexpressing zvegf4. Chronic immune complex deposition, as seen in lupus, hepatitis B and C, and chronic abscesses, may also lead to pro-fibrotic responses in the kidney. Administration of anti-zvegf4 antibodies may beneficially interfere with zvegf4-stimulated pro-fibrotic responses. Such responses include: sclerosing peritonitis, adhesions following surgery, particularly laparoscopic surgery, and restenosis.

Activity of zvegf4 proteins can be measured in vitro using cultured cells or in vivo by administering molecules of the claimed invention to an appropriate animal model. Target cells for use in zvegf4 activity assays include vascular cells (especially endothelial cells, pericytes and smooth muscle cells), hematopoietic (myeloid and lymphoid) cells, liver cells (including hepatocytes, fenestrated endothelial cells, Kupffer cells, and Ito cells), fibroblasts (including human dermal fibroblasts and lung fibroblasts), neurite cells (including astrocytes, glial cells, dendritic cells, and PC-12 cells), fetal lung cells, articular synoviocytes, pericytes, chondrocytes, osteoblasts, kidney mesangial cells, bone marrow stromal cells (see K. Satomura et al., *J. Cell. Physiol.* 177:426–38, 1998), and other cells having cell-surface PDGF receptors.

Zvegf4 proteins can be analyzed for receptor binding activity by a variety of methods well known in the art, including receptor competition assays (Bowen-Pope and Ross, *Methods Enzymol.* 109:69–100, 1985), use of soluble receptors, and use of receptors produced as IgG fusion proteins (U.S. Pat. No. 5,750,375). Receptor binding assays can be performed on cell lines that contain known cell-surface receptors for evaluation. The receptors can be naturally present in the cell, or can be recombinant receptors expressed by genetically engineered cells. Cell types that are able to bind zvegf4 can be identified through the use of a zvegf4 polypeptide conjugated to a cytotoxin or other detectable molecule. Suitable detectable molecules include radionuclides, enzymes, substrates, cofactors, inhibitors, fluorescent markers, chemiluminescent markers, magnetic particles, and the like. Suitable cytotoxic molecules include bacterial or plant toxins (for instance, diphtheria toxin, Pseudomonas exotoxin, ricin, abrin, saporin, and the like), as well as therapeutic radionuclides, such as iodine-131, rhenium-188 or yttrium-90. These can be either directly attached to the polypeptide or indirectly attached according to known methods, such as through a chelating moiety. Polypeptides can also be conjugated to cytotoxic drugs, such as adriamycin. For indirect attachment of a detectable or cytotoxic molecule, the detectable or cytotoxic molecule may be conjugated with a member of a complementary/anticomplementary pair, where the other member is bound to the polypeptide or antibody portion. For these purposes, biotin/streptavidin is an exemplary complementary/anticomplementary pair. Binding of a zvegf4-toxin conjugate by cells, either in tissue culture, in organ culture, or in vivo will allow for the incorporation of the conjugate into the cell, causing cell death. This activity can be used to identify cell types that are able to bind and internalize zvegf4. In addition to allowing for the identification of responsive cell types, toxin conjugates can be used in in vivo studies to identify organs and tissues where zvegf4 has a biological activity by looking for pathology within the animal following injection of the conjugate.

Activity of zvegf4 proteins can be measured in vitro using cultured cells. Mitogenic activity can be measured using known assays, including $^3$H-thymidine incorporation assays (as disclosed by, e.g., Raines and Ross, *Methods Enzymol.* 109:749–773, 1985 and Wahl et al., *Mol. Cell Biol.* 8:5016–5025, 1988), dye incorporation assays (as disclosed by, for example, Mosman, *J. Immunol. Meth.* 65:55–63, 1983 and Raz et al., *Acta Trop.* 68:139–147, 1997) or cell counts. Exemplary mitogenesis assays measure incorporation of $^3$H-thymidine into (1) 20% confluent cultures to look for the ability of zvegf4 proteins to further stimulate proliferating cells, and (2) quiescent cells held at confluence for 48 hours to look for the ability of zvegf4 proteins to overcome contact-induced growth inhibition. See also, Gospodarowicz et al., *J. Cell. Biol.* 70:395–405, 1976; Ewton and Florini, *Endocrinol.* 106:577–583, 1980; and Gospodarowicz et al., *Proc. Natl. Acad. Sci. USA* 86:7311–7315, 1989. Cell differentiation can be assayed using suitable precursor cells that can be induced to differentiate into a more mature phenotype. For example, endothelial cells and hematopoietic cells are derived from a common ancestral cell, the hemangioblast (Choi et al., *Development* 125:725–732, 1998). Mesenchymal stem cells can also be used to measure the ability of zvegf4 protein to stimulate differentiation into osteoblasts. Differentiation is indicated by the expression of osteocalcin, the ability of the cells to mineralize, and the expression of alkaline phosphatase, all of which can be measured by routine methods known in the art. Effects of zvegf4 proteins on tumor cell growth and metastasis can be analyzed using the Lewis lung carcinoma model, for example as described by Cao et al., *J. Exp. Med.* 182:2069–2077, 1995. Activity of zvegf4 proteins on cells of neural origin can be analyzed using assays that measure effects on neurite growth. Zvegf4 can also be assayed in an aortic ring outgrowth assay (Nicosia and Ottinetti, *Laboratory Investigation* 63:115, 1990; Villaschi and Nicosia, *Am. J. Pathology* 143:181–190, 1993).

Zvegf4 activity may also be detected using assays designed to measure zvegf4-induced production of one or more additional growth factors or other macromolecules. Such assays include those for determining the presence of hepatocyte growth factor (HGF), epidermal growth factor (EGF), transforming growth factor alpha (TGFα), interleukin-6 (IL-6), VEGF, acidic fibroblast growth factor (aFGF), and angiogenin. Suitable assays include mitogenesis assays using target cells responsive to the macromolecule of interest, receptor-binding assays, competition binding assays, immunological assays (e.g., ELISA), and other formats known in the art. Metalloprotease secretion is measured from treated primary human dermal fibroblasts, synoviocytes and chondrocytes. The relative levels of collagenase, gelatinase and stromalysin produced in response to culturing in the presence of a zvegf4 protein is measured using zymogram gels (Loita and Stetler-Stevenson, *Cancer Biology* 1:96–106, 1990). Procollagen/collagen synthesis by dermal fibroblasts and chondrocytes in response to a test protein is measured using $^3$H-proline incorporation into nascent secreted collagen. $^3$H-1labeled collagen is visualized by SDS-PAGE followed by autoradiography (Unemori and Amento, *J. Biol. Chem.* 265: 10681–10685, 1990). Glycosaminoglycan (GAG) secretion from dermal fibroblasts and chondrocytes is measured using a 1,9-dimethylmethylene blue dye binding assay (Farndale et al., *Biochim. Biophys. Acta* 883:173–177, 1986). Collagen and GAG assays are also carried out in the presence of IL-1β or TGF-β to examine the ability of zvegf4 protein to modify the established responses to these cytokines.

Monocyte activation assays are carried out (1) to look for the ability of zvegf4 proteins to further stimulate monocyte activation, and (2) to examine the ability of zvegf4 proteins to modulate attachment-induced or endotoxin-induced monocyte activation (Fuhlbrigge et al., *J. Immunol.* 138: 3799–3802, 1987). IL-1β, and TNFα levels produced in response to activation are measured by ELISA (Biosource, Inc. Camarillo, Calif.). Monocyte/macrophage cells, by virtue of CD14 (LPS receptor), are exquisitely sensitive to endotoxin, and proteins with moderate levels of endotoxin-like activity will activate these cells.

Hematopoietic activity of zvegf4 proteins can be assayed on various hematopoietic cells in culture. Suitable assays include primary bone marrow or peripheral blood leukocyte colony assays, and later stage lineage-restricted colony assays, which are known in the art (e.g., Holly et al., WIPO Publication WO 95/21920). Marrow cells plated on a suitable semi-solid medium (e.g., 50% methylcellulose containing 15% fetal bovine serum, 10% bovine serum albumin, and 0.6% PSN antibiotic mix) are incubated in the presence of test polypeptide, then examined microscopically for colony formation. Known hematopoietic factors are used as controls. Mitogenic activity of zvegf4 polypeptides on hematopoietic cell lines can be measured using $^3$H-thymidine incorporation assays, dye incorporation assays, or cell counts (Raines and Ross, *Methods Enzymol.* 109:749–773, 1985 and Foster et al., U.S. Pat. No. 5,641,655). For example, cells are cultured in multi-well microtiter plates. Test samples and $^3$H-thymidine are added, and the cells are incubated overnight at 37° C. Contents of the wells are transferred to filters, dried, and counted to determine incorporation of label. Cell proliferation can also be measured using a calorimetric assay based on the metabolic breakdown of 3-(4,5-dimethylthiazol-2-yl)-2,5-diphenyl tetrazolium bromide (MTT) (Mosman, ibid.). Briefly, a solution of MTT is added to 100 μl of assay cells, and the cells are incubated at 37° C. After 4 hours, 200 μl of 0.04 N HCl in isopropanol is added, the solution is mixed, and the absorbance of the sample is measured at 570 nm.

Cell migration is assayed essentially as disclosed by Kähler et al. (*Arteriosclerosis, Thrombosis, and Vascular Biology* 17:932–939, 1997). A protein is considered to be chemotactic if it induces migration of cells from an area of low protein concentration to an area of high protein concentration. The assay is performed using modified Boyden chambers with a polystryrene membrane separating the two chambers (Transwell; Corning Costar Corp.). The test sample, diluted in medium containing 1% BSA, is added to the lower chamber of a 24-well plate containing Transwells. Cells are then placed on the Transwell insert that has been pretreated with 0.2% gelatin. Cell migration is measured after 4 hours of incubation at 37° C. Non-migrating cells are wiped off the top of the Transwell membrane, and cells attached to the lower face of the membrane are fixed and stained with 0.1% crystal violet. Stained cells are then counted directly using a microscope, or extracted with 10% acetic acid and absorbance is measured at 600 nm. Migration is then calculated from a standard calibration curve.

Cell adhesion activity is assayed essentially as disclosed by LaFleur et al. (*J. Biol. Chem.* 272:32798–32803, 1997). Briefly, microtiter plates are coated with the test protein, non-specific sites are blocked with BSA, and cells (such as smooth muscle cells, leukocytes, or endothelial cells) are plated at a density of approximately $10^4$–$10^5$ cells/well. The wells are incubated at 37° C. (typically for about 60 minutes), then non-adherent cells are removed by gentle washing. Adhered cells are quantitated by conventional methods (e.g., by staining with crystal violet, lysing the cells, and determining the optical density of the lysate). Control wells are coated with a known adhesive protein, such as fibronectin or vitronectin.

Assays for angiogenic activity are also known in the art. For example, the effect of zvegf4 proteins on primordial endothelial cells in angiogenesis can be assayed in the chick chorioallantoic membrane angiogenesis assay (Leung, *Science* 246:1306–1309, 1989; Ferrara, *Ann. NY Acad. Sci.* 752:246–256, 1995). Briefly, a small window is cut into the shell of an eight-day old fertilized egg, and a test substance is applied to the chorioallantoic membrane. After 72 hours, the membrane is examined for neovascularization. Other suitable assays include microinjection of early stage quail (*Coturnix coturnix japonica*) embryos as disclosed by Drake et al. (*Proc. Natl. Acad. Sci. USA* 92:7657–7661, 1995); the rodent model of corneal neovascularization disclosed by Muthukkaruppan and Auerbach (*Science* 205:1416–1418, 1979), wherein a test substance is inserted into a pocket in the cornea of an inbred mouse; and the hampster cheek pouch assay (Höckel et al., *Arch. Surg.* 128:423–429, 1993). Induction of vascular permeability, which is indicative of angiogenic activity, is measured in assays designed to detect leakage of protein from the vasculature of a test animal (e.g., mouse or guinea pig) after administration of a test compound (Miles and Miles, *J. Physiol.* 118:228–257, 1952; Feng et al., *J. Exp. Med.* 183:1981–1986, 1996). In vitro assays for angiogenic activity include the tridimensional collagen gel matrix model (Pepper et al. *Biochem. Biophys. Res. Comm.* 189:824–831, 1992 and Ferrara et al., *Ann. NY Acad. Sci.* 732:246–256, 1995), which measures the formation of tube-like structures by microvascular endothelial cells; and basement membrane matrix models (Grant et al., "Angiogenesis as a component of epithelial-mesenchymal interactions" in Goldberg and Rosen, *Epithelial-Mesenchymal Interaction in Cancer*, Birkhäuser Verlag, 1995, 235–248; Baatout, *Anticancer Research* 17:451–456, 1997), which are used to determine effects on cell migration and tube formation by endothelial cells seeded in a basement membrane extract enriched in laminin (e.g., Matrigel®; Becton Dickinson, Franklin Lakes, N.J.). Angiogenesis assays can be carried out in the presence and absence of VEGF to assess possible combinatorial effects. VEGF can be used as a control within in vivo assays.

The activity of zvegf4 proteins, agonists, antagonists, and antibodies of the present invention can be measured, and compounds screened to identify agonists and antagonists, using assays that measure axon guidance and growth. Of particular interest are assays that indicate changes in neuron growth patterns, for example those disclosed in Hastings, WIPO Publication WO 97/29189 and Walter et al., *Development* 101:685–96, 1987. Assays to measure the effects on neuron growth are well known in the art. For example, the C assay (e.g., Raper and Kapfhammer, *Neuron* 4:21–9, 1990 and Luo et al., *Cell* 75:217–27, 1993) can be used to determine collapsing activity of zvegf4 on growing neurons. Other methods that can assess zvegf4-induced inhibition of neurite extension or divert such extension are also known. See, Goodman, *Annu. Rev. Neurosci.* 19:341–77, 1996. Conditioned media from cells expressing a zvegf4 protein, a zvegf4 agonist, or a zvegf4 antagonist, or aggregates of such cells, can by placed in a gel matrix near suitable neural cells, such as dorsal root ganglia (DRG) or sympathetic ganglia explants, which have been co-cultured with nerve growth factor. Compared to control cells, zvegf4-induced changes in neuron growth can be measured (as disclosed by, for example, Messersmith et al., *Neuron* 14:949–59, 1995 and Puschel et al., *Neuron* 14:941–8, 1995). Likewise neurite outgrowth can be measured using neuronal cell suspensions grown in the presence of molecules of the present invention. See, for example, O'Shea et al., *Neuron* 7:231–7, 1991 and DeFreitas et al., *Neuron* 15:333–43, 1995. PC12 Pheochromocytoma cells (see Banker and Goslin, in *Culturing Nerve Cells*, chapter 6, "Culture and experimental use of the PC12 rat Pheochromocytoma cell line"; also, see Rydel and Greene, *J. Neuroscience* 7(11): 3639–53, November 1987) can be grown in the presence of zvegf4 to examine effects on neurite outgrowth. PC12 cells pre-treated with NGF to induce differentiation into a neuronal population can also be exposed to zvegf4 to determine the ability of zvegf4 to promote survival of neuronal cells.

The biological activities of zvegf4 proteins can be studied in non-human animals by administration of exogenous protein, by expression of zvegf4-encoding polynucleotides, and by suppression of endogenous zvegf4 expression through antisense or knock-out techniques. Zvegf4 proteins can be administered or expressed individually, in combination with other zvegf4 proteins, or in combination with non-vegf3 proteins, including other growth factors (e.g., other VEGFs, PlGFs, or PDGFs). For example, a combination of zvegf4 polypeptides (e.g., a combination of zvegf4$_{19-179}$ and zvegf4$_{258-370}$) can be administered to a test animal or expressed in the animal. Test animals are monitored for changes in such parameters as clinical signs, body weight, blood cell counts, clinical chemistry, histopathology, and the like.

Stimulation of coronary collateral growth can be measured in known animal models, including a rabbit model of peripheral limb ischemia and hind limb ischemia and a pig model of chronic myocardial ischemia (Ferrara et al., *Endocrine Reviews* 18:4–25, 1997). Zvegf4 proteins are assayed in the presence and absence of VEGFs, angiopoietins, and basic FGF to test for combinatorial effects. These models can be modified by the use of adenovirus or naked DNA for gene delivery as disclosed in more detail below, resulting in local expression of the test protein(s).

Efficacy of zvegf4 polypeptides in promoting wound healing can be assayed in animal models. One such model is the linear skin incision model of Mustoe et al. (*Science* 237:1333, 1987). In a typical procedure, a 6-cm incision is made in the dorsal pelt of an adult rat, then closed with wound clips. Test substances and controls (in solution, gel, or powder form) are applied before primary closure. Although administration is commonly limited to a single application, additional applications can be made on succeeding days by careful injection at several sites under the incision. Wound breaking strength is evaluated between 3 and 21 days post-wounding. In a second model, multiple, small, full-thickness excisions are made on the ear of a rabbit. The cartilage in the ear splints the wound, removing the variable of wound contraction from the evaluation of closure. Experimental treatments and controls are applied. The geometry and anatomy of the wound site allow for reliable quantification of cell ingrowth and epithelial migration, as well as quantitative analysis of the biochemistry of the wounds (e.g., collagen content). See, Mustoe et al., *J. Clin. Invest.* 87:694, 1991. The rabbit ear model can be modified to create an ischemic wound environment, which more closely resembles the clinical situation (Ahn et al., *Ann. Plast. Surg.* 24:17, 1990). Within a third model, healing of partial-thickness skin wounds in pigs or guinea pigs is evaluated (LeGrand et al., *Growth Factors* 8:307, 1993). Experimental treatments are applied daily on or under dressings. Seven days after wounding, granulation tissue thickness is determined. This model is commonly used for dose-response studies, as it is more quantitative than other in vivo models of wound healing. A full thickness excision model can also be employed. Within this model, the epidermis and dermis are removed down to the panniculus carnosum in rodents or the subcutaneous fat in pigs. Experimental treatments are applied topically on or under a dressing, and can be applied daily if desired. The wound closes by a combination of contraction and cell ingrowth and proliferation. Measurable endpoints include time to wound closure, histologic score, and biochemical parameters of wound tissue. Impaired wound healing models are also known in the art (e.g., Cromack et al., *Surgery* 113:36, 1993; Pierce et al., *Proc. Natl. Acad. Sci. USA* 86:2229, 1989; Greenhalgh et al., *Amer. J. Pathol.* 136:1235, 1990). Delay or prolongation of the wound healing process can be induced pharmacologically by treatment with steroids, irradiation of the wound site, or by concomitant disease states (e.g., diabetes). Linear incisions or full-thickness excisions are most commonly used as the experimental wound. Endpoints are as disclosed above for each type of wound. Subcutaneous implants can be used to assess compounds acting in the early stages of wound healing (Broadley et al., *Lab. Invest.* 61:571, 1985; Sprugel et al., *Amer. J. Pathol.* 129: 601, 1987). Implants are prepared in a porous, relatively non-inflammatory container (e.g., polyethylene sponges or expanded polytetrafluoroethylene implants filled with bovine collagen) and placed subcutaneously in mice or rats. The interior of the implant is empty of cells, producing a "wound space" that is well-defined and separable from the preexisting tissue. This arrangement allows the assessment of cell influx and cell type as well as the measurement of vasculogenesis/angiogenesis and extracellular matrix production.

Expression of zvegf4 proteins in animals provides models for study of the biological effects of overproduction or inhibition of protein activity in vivo. Zvegf4-encoding polynucleotides can be introduced into test animals, such as mice, using viral vectors or naked DNA, or transgenic animals can be produced. A zvegf4 protein will commonly be expressed with a secretory peptide. Suitable secretory peptides include the zvegf4 secretory peptide (e.g., residues 1–18 of SEQ ID NO:2) and heterologous secretory peptides. An exemplary heterologous secretory peptide is that of human tissue plasminogen activator (t-PA). The t-PA secretory peptide may be modified to reduce undesired proteolytic cleavage as disclosed in U.S. Pat. No. 5,641,655.

One in vivo approach for assaying proteins of the present invention utilizes viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161–89, 1994; and Douglas and Curiel, *Science & Medicine* 4:44–53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined. Intranasal delivery of adenovirus expressing zvegf4 will target the zvegf4 protein to lung tissue. Further, adenovirus expressing zvegf4 can be administered directly into brain tissue. Adenoviral vectors containing various deletions of viral genes can be used in an attempt to reduce or eliminate immune responses to the vector. Such adenoviruses are E1 deleted, and in addition contain deletions of E2A or E4 (Lusky et al., *J. Virol.* 72:2022–2032, 1998; Raper et al., *Human Gene Therapy* 9:671–679, 1998). In addition, deletion of E2b is reported to reduce immune responses (Amalfitano, et al., *J. Virol.* 72:926–933, 1998). Generation of so-called "gutless" adenoviruses where all viral transcription units are deleted is particularly advantageous for insertion of large inserts of heterologous DNA. For review, see Yeh and Perricaudet, *FASEB J.* 11:615–623, 1997.

In another embodiment, a zvegf4 gene can be introduced in a retroviral vector as described, for example, by Anderson et al., U.S. Pat. No. 5,399,346; Mann et al., *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; Dougherty et al., WIPO publication WO 95/07358; and Kuo et al., *Blood* 82:845, 1993.

In an alternative method, the vector can be introduced by "lipofection" in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. For instance, directing transfection to particular cell types is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Within another embodiment target cells are removed from the animal, and the DNA is introduced as a naked DNA plasmid. The transformed cells are then re-implanted into the body of the animal. Naked DNA vectors can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Mice engineered to express the zvegf4 gene, referred to as "transgenic mice," and mice that exhibit a complete absence of zvegf4 gene function, referred to as "knockout mice," can also be generated (Snouwaert et al., *Science* 257:1083, 1992; Lowell et al., *Nature* 366:740–42, 1993; Capecchi, *Science* 244:1288–1292, 1989; Palmiter et al., *Ann. Rev. Genet.* 20:465–499, 1986). Transgenesis experiments can be performed using normal mice or mice with genetic disease or other altered phenotypes. Transgenic mice that over-express zvegf4, either ubiquitously or under a tissue-specific or tissue-restricted promoter, can be used to determine whether or not over-expression causes a phenotypic change. Exemplary promoters include metallothionein, albumin, ApoA1 and enolase gene promoters. The metallothionein-1 (MT-1) promoter provides expression in liver and other tissues, often leading to high levels of circulating protein. Over-expression of a wild-type zvegf4 polypeptide, polypeptide fragment or a mutant thereof may alter normal cellular processes, resulting in a phenotype that identifies a tissue in which zvegf4 expression is functionally relevant and may indicate a therapeutic target for the zvegf4, its agonists or antagonists. For example, a transgenic mouse can be engineered to over-expresses a full-length zvegf4 sequence, which may result in a phenotype that shows similarity with human diseases. Similarly, knockout zvegf4 mice can be used to determine where zvegf4 is absolutely required in vivo. The phenotype of knockout mice is predictive of the in vivo effects of zvegf4 antagonists. Knockout mice can also be used to study the effects of zvegf4 proteins in models of disease, including, for example, cancer, atherosclerosis, rheumatoid arthritis, ischemia, and cardiovascular disease. The human zvegf4 cDNA can be used to isolate murine zvegf4 mRNA, cDNA and genomic DNA as disclosed above, which are subsequently used to generate knockout mice. These mice may be employed to study the zvegf4 gene and the protein encoded thereby in an in vivo system, and can be used as in vivo models for corresponding human diseases. Moreover, transgenic mice expressing zvegf4 antisense polynucleotides or ribozymes directed against zvegf4, described herein, can be used analogously to knockout mice described above.

Antisense methodology can be used to inhibit zvegf4 gene transcription to examine the effects of such inhibition in vivo. Polynucleotides that are complementary to a segment of a zvegf4-encoding polynucleotide (e.g., a polynucleotide as set froth in SEQ ID NO:1) are designed to bind to zvegf4-encoding mRNA and to inhibit translation of such mRNA. Such antisense oligonucleotides can also be used to inhibit expression of zvegf4 polypeptide-encoding genes in cell culture.

Zvegf4 proteins may be used therapeutically in human and veterinary medicine to stimulate tissue development or repair, or cellular differentiation or proliferation. Specific applications include, without limitation: the treatment of full-thickness skin wounds, including venous stasis ulcers and other chronic, non-healing wounds, particularly in cases of compromised wound healing due to diabetes mellitus, connective tissue disease, smoking, burns, and other exacerbating conditions; fracture repair; skin grafting; within reconstructive surgery to promote neovascularization and increase skin flap survival; to establish vascular networks in transplanted cells and tissues, such as transplanted islets of Langerhans; to treat female reproductive tract disorders, including acute or chronic placental insufficiency (an important factor causing perinatal morbidity and mortality) and prolonged bleeding; to promote the growth of tissue damaged by periodontal disease; to promote endothelialization of vascular grafts and stents; in the treatment of acute and chronic lesions of the gastrointestinal tract, including duodenal ulcers, which are characterized by a deficiency of microvessels; to promote angiogenesis and prevent neuronal degeneration due to acute or chronic cerebral ischemia; to accelerate the formation of collateral blood vessels in ischemic limbs; to promote vessel re-endothelialization and to reduce intimal hyperplasia following invasive procedures such as balloon angioplasty and stent placement; to promote vessel repair and development of collateral circulation following myocardial infarction so as to limit ischemic injury; and to stimulate hematopoiesis. The polypeptides are also useful additives in tissue adhesives for promoting revascularization of the healing tissue.

Of particular interest is the use of zvegf4 for the treatment or repair of liver damage, including damage due to chronic liver disease, including chronic active hepatitis and many other types of cirrhosis. Widespread, massive necrosis, including destruction of virtually the entire liver, can be caused by, inter alia, fulminant viral hepatitis; overdoses of the analgesic acetaminophen; exposure to other drugs and chemicals such as halothane, monoamine oxidase inhibitors, agents employed in the treatment of tuberculosis, phosphorus, carbon tetrachloride, and other industrial chemicals. Conditions associated with ultrastructural lesions that do not necessarily produce obvious liver cell necrosis include Reye's syndrome in children, tetracycline toxicity, and acute fatty liver of pregnancy. Cirrhosis, a diffuse process characterized by fibrosis and a conversion of normal architecture into structurally abnormal nodules, can come about for a variety reasons including alcohol abuse, post necrotic cirrhosis (usually due to chronic active hepatitis), biliary cirrhosis, pigment cirrhosis, cryptogenic cirrhosis, Wilson's disease, and alpha-1-antitrypsin deficiency. Zvegf4 may also be useful for the treatment of hepatic chronic passive congestion (CPC) and central hemorrhagic necrosis (CHN), which are two circulatory changes representing a continuum encountered in right-sided heart failure. Other circulatory disorders that may be treated with zvegf4 include hepatic vein thrombosis, portal vein thrombosis, and cardiac sclerosis. In cases of liver fibrosis, it may be beneficial to administer a zvegf4 antagonist to suppress the activation of stellate cells, which have been implicated in the production of extracellular matrix in fibrotic liver (Li and Friedman, *J. Gastroenterol. Hepatol.* 14:618–633, 1999). More generally, zvegf4 may be beneficially used as an anti-fibrotic agent. Conditions that are characterized by a pro-fibrotic response include sclerosing peritonitis; adhesions following surgery (particularly laparoscopic surgery), which may lead to small bowel obstruction, difficulties on re-operation, pelvic adhesions and pelvic pain (see N. Panay and A. M. Lower, *Curr. Opin. Obstet. Gynecol.* 11:379–85, 1999); pulmonary fibrosis; kidney fibrosis; and restenosis.

Zvegf4 polypeptides can be administered alone or in combination with other vasculogenic or angiogenic agents, including VEGF and angiopoietins 1 and 2. For example, basic and acidic FGFs, Ang-1, Ang-2, and VEGF have been found to play a role in the development of collateral circulation, and the combined use of zvegf4 with one or more of these factors may be advantageous. VEGF has also been implicated in the survival of transplanted islet cells (Gorden et al. *Transplantation* 63:436443, 1997; Pepper, *Arteriosclerosis, Throm. and Vascular Biol.* 17:605–619, 1997). Basic FGF has been shown to induce angiogenesis and accelerate healing of ulcers in experimental animals (reviewed by Folkman, *Nature Medicine* 1:27–31, 1995). VEGF has been shown to promote vessel re-endothelialization and to reduce intimal hyperplasia in animal models of restenosis (Asahara et al., *Circulation* 91:2802–2809, 1995; Callow et al., *Growth Factors* 10:223–228, 1994); efficacy of zvegf4 polypeptides can be tested in these and other known models. When using zvegf4 in combination with an additional agent, the two compounds can be administered simultaneously or sequentially as appropriate for the specific condition being treated.

Zvegf4 proteins may be used either alone or in combination with other hematopoietic factors such as IL-3, G-CSF, GM-CSF, or stem cell factor to enhance expansion and mobilization of hematopoietic stem cells, including endothelial precursor stem cells. Cells that can be expanded in this manner include cells isolated from bone marrow, including bone marrow stromal cells (see K. Satomura et al., *J. Cell. Physiol.* 177:426–38, 1998), or cells isolated from blood. Zvegf4 proteins may also be given directly to an individual to enhance endothelial stem cell production and differentiation within the treated individual. The stem cells, either developed within the patient, or provided back to a patient, may then play a role in modulating areas of ischemia within the body, thereby providing a therapeutic effect. These cells may also be useful in enhancing re-endothelialization of areas devoid of endothelial coverage, such as vascular grafts, vascular stents, and areas where the endothelial coverage has been damaged or removed (e.g., areas of angioplasty). Zvegf4 proteins may also be used in combination with other growth and differentiation factors such as angiopoietin-1 (Davis et al., *Cell* 87:1161–1169, 1996) to help create and stabilize new vessel formation in areas requiring neovascularization, including areas of ischemia (cardiac or peripheral ischemia), organ transplants, wound healing, and tissue grafting.

Zvegf4 proteins, agonists and antagonists may be used to modulate neurite growth and development and demarcate nervous system structures. As such, Zvegf4 proteins, agonists, and antagonists would be useful as a treatment of peripheral neuropathies by increasing spinal cord and sensory neurite outgrowth. A zvegf4 antagonist could be part of a therapeutic treatment for the regeneration of neurite outgrowths following strokes, brain damage caused by head injuries and paralysis caused by spinal injuries. Application may also be made in treating neurodegenerative diseases such as multiple sclerosis, Alzheimer's disease and Parkinson's disease. Application may also be made in mediating development and innervation pattern of stomach tissue.

Zvegf4 has been found to have PDGF-like activity, including mitogenic activity on fibroblasts, vascular smooth muscle cells, and pericytes. Zvegf4 has also been found to stimulate bone growth in an animal model. These results suggest that zvegf4 proteins will be useful in promoting the growth of bone and ligament. Such uses include, for example, treatment of periodontal disease, fractures (including non-union fractures), implant recipient sites, bone grafts, and joint injuries involving cartilage and/or ligament damage. Zvegf4 may be used in combination with other bone stimulating factors, such as IGF-1, EGF, TGF-β, PDGF, and BMPs. Methods for using growth factors in the treatment of periodontal disease are known in the art. See, for example, U.S. Pat. No. 5,124,316 and Lynch et al., ibid.

For pharmaceutical use, zvegf4 proteins, antagonist, and antibodies are formulated for topical or parenteral, particularly intravenous or subcutaneous, delivery according to conventional methods. In general, pharmaceutical formulations will include a zvegf4 polypeptide in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, thickeners, gelling agents, etc. Methods of formulation are well known in the art and are disclosed, for example, in *Remington: The Science and Practice of Pharmacy*, Gennaro, ed., Mack Publishing Co., Easton, Pa., 19th ed., 1995. Zvegf4 will ordinarily be used in a concentration of about 10 to 100 μg/ml of total volume, although concentrations in the range of 1 ng/ml to 1000 μg/ml may be used. For topical application, such as for the promotion of wound healing, the protein will be applied in the range of 0.1–10 μg/cm$^2$ of wound area, with the exact dose determined by the clinician according to accepted standards, taking into account the nature and severity of the condition to be treated, patient traits, etc. Determination of dose is within the level of ordinary skill in the art. The therapeutic formulations will generally be administered over the period required for neovascularization, typically from one to several months and, in treatment of chronic conditions, for a year or more. Dosing is daily or intermittently over the period of treatment. Intravenous administration will be by bolus injection or infusion over a typical period of one to several hours. Sustained release formulations can also be employed. In general, a therapeutically effective amount of zvegf4 is an amount sufficient to produce a clinically significant change in the treated condition, such as a clinically significant reduction in time required by wound closure, a significant reduction in wound area, a significant improvement in vascularization, a significant reduction in morbidity, or a significantly increased histological score.

Proteins of the present invention are useful for modulating the proliferation, differentiation, migration, or metabolism of responsive cell types, which include both primary cells and cultured cell lines. Of particular interest in this regard are hematopoietic cells (including stem cells and mature myeloid and lymphoid cells), endothelial cells, neuronal cells, mesenchymal cells (including fibroblasts, pericytes, stellate cells, mesangial cells, chondrocytes and smooth muscle cells), and bone-derived cells (including osteoblast and osteoclast precursors). Zvegf4 polypeptides are added to tissue culture media for these cell types at a concentration of about 10 pg/ml to about 1000 ng/ml. Those skilled in the art will recognize that zvegf4 proteins can be advantageously combined with other growth factors in culture media.

Within the laboratory research field, zvegf4 proteins can also be used as molecular weight standards; as reagents in assays for determining circulating levels of the protein, such as in the diagnosis of disorders characterized by over- or under-production of zvegf4 protein; or as standards in the analysis of cell phenotype.

Zvegf4 proteins can also be used to identify inhibitors of their activity. Test compounds are added to the assays disclosed above to identify compounds that inhibit the activity of zvegf4 protein. In addition to those assays disclosed above, samples can be tested for inhibition of zvegf4 activity within a variety of assays designed to measure receptor binding or the stimulation/inhibition of zvegf4-dependent cellular responses. For example, zvegf4-responsive cell lines can be transfected with a reporter gene construct that is responsive to a zvegf4-stimulated cellular pathway. Reporter gene constructs of this type are known in the art, and will generally comprise a zvegf4-activated serum response element (SRE) operably linked to a gene encoding an assayable protein, such as luciferase. Candidate compounds, solutions, mixtures or extracts are tested for the ability to inhibit the activity of zvegf4 on the target cells as evidenced by a decrease in zvegf4 stimulation of reporter gene expression. Assays of this type will detect compounds that directly block zvegf4 binding to cell-surface receptors, as well as compounds that block processes in the cellular pathway subsequent to receptor-ligand binding. In the alternative, compounds or other samples can be tested for direct blocking of zvegf4 binding to receptor using zvegf4 tagged with a detectable label (e.g., $^{125}$I, biotin, horseradish peroxidase, FITC, and the like). Within assays of this type, the ability of a test sample to inhibit the binding of labeled zvegf4 to the receptor is indicative of inhibitory activity, which can be confirmed through secondary assays. Receptors used within binding assays may be cellular receptors or isolated, immobilized receptors.

The activity of zvegf4 proteins can be measured with a silicon-based biosensor microphysiometer that measures the extracellular acidification rate or proton excretion associated with receptor binding and subsequent physiologic cellular responses. An exemplary such device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell et al., *Science* 257:1906–1912, 1992; Pitchford et al., *Meth. Enzymol.* 228:84–108, 1997; Arimilli et al., *J. Immunol. Meth.* 212:49–59, 1998; and Van Liefde et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including zvegf4 proteins, their agonists, and antagonists. The microphysiometer can be used to measure responses of a zvegf4-responsive eukaryotic cell, compared to a control eukaryotic cell that does not respond to zvegf4 polypeptide. Zvegf4-responsive eukaryotic cells comprise cells into which a receptor for zvegf4 has been transfected creating a cell that is responsive to zvegf4, as well as cells naturally responsive to zvegf4 such as cells derived from vascular or neural tissue. Differences, measured by a change in extracellular acidification, in the response of cells exposed to zvegf4 polypeptide relative to a control not exposed to zvegf4, are a direct measurement of zvegf4-modulated cellular responses. Moreover, such zvegf4-modulated responses can be assayed under a variety of stimuli. The present invention thus provides methods of identifying agonists and antagonists of zvegf4 proteins, comprising providing cells responsive to a zvegf4 polypeptide, culturing a first portion of the cells in the absence of a test compound, culturing a second portion of the cells in the presence of a test compound, and detecting a change in a cellular response of the second portion of the cells as compared to the first portion of the cells. The change in cellular response is shown as a measurable change in extracellular acidification rate. Culturing a third portion of the cells in the presence of a zvegf4 protein and the absence of a test compound provides a positive control for the zvegf4-responsive cells and a control to compare the agonist activity of a test compound with that of the zvegf4 polypeptide. Antagonists of zvegf4 can be identified by exposing the cells to zvegf4 protein in the presence and absence of the test compound, whereby a reduction in zvegf4-stimulated activity is indicative of antagonist activity in the test compound.

Zvegf4 proteins can also be used to identify cells, tissues, or cell lines that respond to a zvegf4-stimulated pathway. The microphysiometer, described above, can be used to rapidly identify ligand-responsive cells, such as cells responsive to zvegf4 proteins. Cells are cultured in the presence or absence of zvegf4 polypeptide. Those cells that elicit a measurable change in extracellular acidification in the presence of zvegf4 are responsive to zvegf4. Responsive cells can than be used to identify antagonists and agonists of zvegf4 polypeptide as described above.

Inhibitors of zvegf4 activity (zvegf4 antagonists) include anti-zvegf4 antibodies and soluble zvegf4 receptors, as well as other peptidic and non-peptidic agents, including ribozymes, small molecule inhibitors, and angiogenically or mitogenically inactive receptor-binding fragments of zvegf4 polypeptides. Such antagonists can be use to block biological activities of zvegf4, including mitogenic, chemotactic, or angiogenic effects. These antagonists are therefore useful in reducing the growth of solid tumors by inhibiting neovascularization of the developing tumor or by directly blocking tumor cell growth; in the treatment of diabetic retinopathy, psoriasis, arthritis, and scleroderma; and in reducing fibrosis, including scar formation. Inhibitors of zvegf4 may also be useful in the treatment of proliferative vascular disorders wherein zvegf4 activity is pathogenic. Such disorders may include atherosclerosis and intimal hyperplastic restenosis following angioplasty, endarterectomy, vascular grafting, organ transplant, or vascular stent emplacement. These conditions involve complex growth factor-mediated responses wherein certain factors may be beneficial to the clinical outcome and others may be pathogenic.

Inhibitors of zvegf4 may also prove useful in the treatment of ocular neovascularization, including diabetic retinopathy and age-related macular degeneration. Experimental evidence suggests that these conditions result from the expression of angiogenic factors induced by hypoxia in the retina.

Zvegf4 antagonists are also of interest in the treatment of inflammatory disorders, such as rheumatoid arthritis and psoriasis. In rheumatoid arthritis, studies suggest that VEGF plays an important role in the formation of pannus, an extensively vascularized tissue that invades and destroys cartilage. Psoriatic lesions are hypervascular and overexpress the angiogenic polypeptide IL-8.

Zvegf4 antagonists may also prove useful in the treatment of infantile hemangiomas, which exhibit overexpression of VEGF and bFGF during the proliferative phase.

Inhibitors are formulated for pharmaceutical use as generally disclosed above, taking into account the precise chemical and physical nature of the inhibitor and the condition to be treated. The relevant determinations are within the level of ordinary skill in the formulation art. Other angiogenic and vasculogenic factors, including VEGF and bFGF, have been implicated in pathological neovascularization. In such instances it may be advantageous to combine a zvegf4 inhibitor with one or more inhibitors of these other factors.

The polypeptides, nucleic acids, and antibodies of the present invention may be used in diagnosis or treatment of disorders associated with cell loss or abnormal cell proliferation (including cancer), including impaired or excessive vasculogenesis or angiogenesis, and diseases of the nervous system. Labeled zvegf4 polypeptides may be used for imaging tumors or other sites of abnormal cell proliferation. Because angiogenesis in adult animals is generally limited to wound healing and the female reproductive cycle, it is a very specific indicator of pathological processes. Angiogenesis is indicative of, for example, developing solid tumors, retinopathies, and arthritis.

Zvegf4 polypeptides and anti-zvegf4 antibodies can be directly or indirectly conjugated to drugs, toxins, radionuclides and the like, and these conjugates used for in vivo diagnostic or therapeutic applications. For instance, polypeptides or antibodies of the present invention may be used to identify or treat tissues or organs that express a corresponding anti-complementary molecule (receptor or antigen, respectively, for instance). More specifically, zvegf4 polypeptides or anti-zvegf4 antibodies, or bioactive fragments or portions thereof, can be coupled to detectable or cytotoxic molecules and delivered to a mammal having cells, tissues, or organs that express the anti-complementary molecule. For example, the CUB domain of zvegf4 can be used to target peptidic and non-peptidic moieties to semaphorins as disclosed above. In another embodiment, polypeptide-toxin fusion proteins or antibody/fragment-toxin fusion proteins may be used for targeted cell or tissue inhibition or ablation, such as in cancer therapy. Of particular interest in this regard are conjugates of a zvegf4 polypeptide and a cytotoxin, which can be used to target the cytotoxin to a tumor or other tissue that is undergoing undesired angiogenesis or neovascularization.

In another embodiment, zvegf4-cytokine fusion proteins or antibody/fragment-cytokine fusion proteins may be used for enhancing in vitro cytotoxicity (for instance, that mediated by monoclonal antibodies against tumor targets) and for enhancing in vivo killing of target tissues (for example, blood and bone marrow cancers). See, generally, Hornick et al., *Blood* 89:4437–4447, 1997). In general, cytokines are toxic if administered systemically. The described fusion proteins enable targeting of a cytokine to a desired site of action, such as a cell having binding sites for zvegf4, thereby providing an elevated local concentration of cytokine. Suitable cytokines for this purpose include, for example, interleukin-2 and granulocyte-macrophage colony-stimulating factor (GM-CSF). Such fusion proteins may be used to cause cytokine-induced killing of tumors and other tissues undergoing angiogenesis or neovascularization.

In yet another embodiment, a zvegf4 polypeptide or anti-zvegf4 antibody can be conjugated with a radionuclide, particularly with a beta-emitting or gamma-emitting radionuclide, and used to reduce restenosis. For instance, iridium-192 impregnated ribbons placed into stented vessels of patients until the required radiation dose was delivered resulted in decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intra-arterially or intraductally, or may be introduced locally at the intended site of action.

Polynucleotides encoding zvegf4 polypeptides are useful within gene therapy applications where it is desired to increase or inhibit zvegf4 activity. For example, Isner et al., *The Lancet* (ibid.) reported that VEGF gene therapy promoted blood vessel growth in an ischemic limb. Additional applications of zvegf4 gene therapy include stimulation of wound healing, repopulation of vascular grafts, stimulation of neurite growth, and inhibition of cancer growth and metastasis. Gene delivery systems useful in this regard include adenovirus, adeno-associated virus, and naked DNA vectors.

The present invention also provides polynucleotide reagents for diagnostic use. For example, a zvegf4 gene, a probe comprising zvegf4 DNA or RNA, or a subsequence thereof can be used to determine if a mutation has occurred at the zvegf4 locus on human chromosome 11. Detectable chromosomal aberrations at the zvegf4 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; A. J. Marian, Chest 108:255–265, 1995).

The invention is further illustrated by the following non-limiting examples.

EXAMPLES

Example 1

Human Multiple Tissue Northern Blots I, II, III and Human RNA Master Blots (Clontech Laboratories, Inc., Palo Alto, Calif.) were probed to determine the tissue expression of zvegf4. Blots were prehybridized for 3 hours at 65 degrees in 10 ml of a hybridization solution (EXPRESSHYB™ Hybridization Solution; Clontech Laboratories, Inc.) containing 1 mg of salmon sperm DNA that had been boiled 5 minutes, then iced 1 minute. The probe used was a 251-bp PCR fragment generated with 20 pmole each of primers ZC21,119 (SEQ ID NO:25) and ZC21,120 (SEQ ID NO:26), and 5 μl of a heart cDNA library prepared from heart RNA using a commercially available kit (MARATHON™ cDNA Amplification Kit from Clontech Laboratories, Inc.). The reaction was run as follows: 94 degrees for 1 minute; then 30 cycles of 94 degrees, 20 seconds; 67 degrees, 1 minute; and ended with a 5-minute incubation at 72 degrees. The PCR product was gel-purified, and the DNA was eluted from the gel slab with a spin column containing a silica gel membrane (QIAQUICK™ Gel Extraction Kit; Qiagen, Inc., Valencia, Calif.).

51 ng of the resulting zvegf4 fragment was labeled with $^{32}$p using a commercially available kit (REDIPRIME™ II random-prime labeling system; Amersham Pharmacia Biotech, Piscataway, N.J.). Unincorporated radioactivity was removed with a push column (NUCTRAP®) column; Stratagene, La Jolla, Calif.; see U.S. Pat. No. 5,336,412). $10 \times 10^6$ cpm of the resulting labeled probe and 1 mg of salmon sperm DNA were boiled 5 minutes, iced 1 minute, then mixed with 10 ml hybridization solution (EXPRESSHYB™) and added to blots. Hybridization took place overnight at 65 degrees, followed by a wash in 2×SSC, 0.1% SDS at room temperature, followed by a wash in 0.1×SSC, 0.1% SDS at 50 degrees. Blots were exposed to film at −80 degrees overnight.

There was an approximately 4.4 kb transcript in every tissue except bone marrow. Heart, pancreas, stomach and adrenal gland showed the strongest zvegf4 expression on the Northern blots, and the dot blot additionally showed strong expression in the pituitary gland and the ovary.

Example 2

Zvegf4 was identified from the sequence of a clone from a human chronic myelogenous leukemia cell (K562) library by its homology to the VEGF family. Additional sequence was elucidated from a long sequence read of a clone from a pituitary library. An antisense expressed sequence tag (EST) for zvegf4 was found, for which its 5' partner was identified. This 5' EST (EST448186; GenBank) appeared to contain the 5' untranslated sequence for zvegf4. A primer was designed from EST448186 to close the gap in the sequence. 20 pm each of ZC21,987 (SEQ ID NO:27) and ZC21,120 (SEQ ID NO:26) and 1.93 μg of a thyroid library were used in the PCR reaction. It was a modified PCR reaction using 5% DMSO and 1/10 volume of a commercial reagent (GC-MELT™; Clontech Laboratories, Inc.). The reaction was run for 1 minute at 94 degrees; then 30 cycles of 94 degrees, 20 seconds; 67 degrees, 1 minute; then a final 5-minute incubation at 72 degrees. A resulting 833-bp product was sequenced and found to be a zvegf4 fragment containing the remainder of the coding sequence with an intiation MET codon, upstream stop codon, and 5' untranslated sequence. The composite sequence included an open reading frame of 1,110 bp (SEQ ID NO:1).

Example 3

To make transgenic animals expressing zvegf4 genes requires adult, fertile males (studs) (B6C3f1, 2–8 months of age (Taconic Farms, Germantown, N.Y.)), vasectomized males (duds) (B6D2f1, 2–8 months, (Taconic Farms)), prepubescent fertile females (donors) (B6C3f1, 4–5 weeks, (Taconic Farms)) and adult fertile females (recipients) (B6D2f1, 2–4 months, (Taconic Farms)).

The donors are acclimated for 1 week, then injected with approximately 8 IU/mouse of Pregnant Mare's Serum gonadotrophin (Sigma, St. Louis, Mo.) I.P., and 46–47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope (Leica MZ12 Stereo Microscope; Leica, Wetzlar, Germany). The oviducts are collected and eggs are released into urinanalysis slides containing hyaluronidase (Sigma Chemical Co.). Eggs are washed once in hyaluronidase, and twice in Whitten's W640 medium (Table 7; all reagents available from Sigma Chemical Co.) that has been incubated with 5% $CO_2$, 5% $O_2$, and 90% $N_2$ at 37° C. The eggs are stored in a 37° C./5% $CO_2$ incubator until microinjection.

TABLE 7

|  | mgs/200 ml | mgs/500 ml |
|---|---|---|
| NaCl | 1280 | 3200 |
| KCl | 72 | 180 |
| $KH_2PO_4$ | 32 | 80 |
| $MgSO_4.7H_2O$ | 60 | 150 |
| Glucose | 200 | 500 |
| $Ca^{2+}$ Lactate | 106 | 265 |
| Benzylpenicillin | 15 | 37.5 |
| Streptomycin $SO_4$ | 10 | 25 |
| $NaHCO_3$ | 380 | 950 |

TABLE 7-continued

|  | mgs/200 ml | mgs/500 ml |
| --- | --- | --- |
| Na Pyruvate | 5 | 12.5 |
| $H_2O$ | 200 ml | 500 ml |
| 500 mM EDTA | 100 µl | 250 µl |
| 5% Phenol Red | 200 µl | 500 µl |
| BSA | 600 | 1500 |

Zvegf4 cDNA is inserted into the expression vector pHB12–8 (see FIG. 2). Vector pHB12–8 was derived from p2999B4 (Palmiter et al., *Mol. Cell Biol.* 13:5266–5275, 1993) by insertion of a rat insulin II intron (ca. 200 bp) and polylinker (Fse I/Pme I/Asc I) into the Nru I site. The vector comprises a mouse metallothionein (MT-1) promoter (ca. 750 bp) and human growth hormone (hGH) untranslated region and polyadenylation signal (ca. 650 bp) flanked by 10 kb of MT-1 5' flanking sequence and 7 kb of MT-1 3' flanking sequence. The cDNA is inserted between the insulin II and hGH sequences.

10–20 micrograms of plasmid DNA is linearized, gel-purified, and resuspended in 10 mM Tris pH 7.4, 0.25 mM EDTA pH 8.0, at a final concentration of 5–10 nanograms per microliter for microinjection.

Plasmid DNA is microinjected into harvested eggs contained in a drop of W640 medium overlaid by warm, $CO_2$-equilibrated mineral oil. The DNA is drawn into an injection needle (pulled from a 0.75 mm ID, 1 mm OD borosilicate glass capillary) and injected into individual eggs. Each egg is penetrated with the injection needle into one or both of the haploid pronuclei.

Picoliters of DNA are injected into the pronuclei, and the injection needle is withdrawn without coming into contact with the nucleoli. The procedure is repeated until all the eggs are injected. Successfully microinjected eggs are transferred into an organ tissue-culture dish with pregassed W640 medium for storage overnight in a 37° C./5% $CO_2$ incubator.

The following day, 2-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12–17 healthy 2-cell embryos from the previous day's injection are transferred into the recipient. The swollen ampulla is located, and, holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs are allowed to slide in. The peritoneal wall is closed with one suture, and the skin is closed with a wound clip. The mice recuperate on a 37° C. slide warmer for a minimum of 4 hours.

The recipients are returned to cages in pairs, and allowed 19–21 days gestation. After birth, 19–21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using a commercially available kit (DNEASY™ 96 Tissue Kit; Qiagen, Valencia, Calif.) following the manufacturer's instructions. Genomic DNA is analyzed by PCR using primers designed to the human growth hormone (hGH) 3' UTR portion of the transgenic vector. The use of a region unique to the human sequence (identified from an alignment of the human and mouse growth hormone 3' UTR DNA sequences) ensures that the PCR reaction does not amplify the mouse sequence. Primers ZC17,251 (SEQ ID NO:28 and ZC17,252 (SEQ ID NO:29) amplify a 368-base-pair fragment of hGH. In addition, primers ZC17,156 (SEQ ID NO:30) and ZC17,157 (SEQ ID NO:31), which hybridize to vector sequences and amplify the cDNA insert, may be used along with the hGH primers. In these experiments, DNA from animals positive for the transgene will generate two bands, a 368-base-pair band corresponding to the hGH 3' UTR fragment and a band of variable size corresponding to the cDNA insert.

Once animals are confirmed to be transgenic (TG), they are back-crossed into an inbred strain by placing a TG female with a wild-type male, or a TG male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the xiphoid process. Using sterile technique, a small 1.5–2 cm incision is made below the sternum, and the left lateral lobe of the liver is exteriorized. Using 4-0 silk, a tie is made around the lower lobe securing it outside the body cavity. An atraumatic clamp is used to hold the tie while a second loop of absorbable Dexon (American Cyanamid, Wayne, N.J.) is placed proximal to the first tie. A distal cut is made from the Dexon tie, and approximately 100 mg of the excised liver tissue is placed in a sterile petri dish. The excised liver section is transferred to a 14-ml polypropylene round bottom tube, snap frozen in liquid nitrogen, and stored on dry ice. The surgical site is closed with suture and wound clips, and the animal's cage is placed on a 37° C. heating pad for 24 hours post-operatively. The animal is checked daily post-operatively, and the wound clips are removed 7–10 days after surgery.

Analysis of the mRNA expression level of each transgene is done using an RNA solution hybridization assay or real-time PCR on an ABI Prism 7700 (PE Applied Biosystems, Inc., Foster City, Calif.) following the manufacturer's instructions.

Example 4

An expression plasmid containing all or part of a polynucleotide encoding zvegf4 is constructed via homologous recombination. A fragment of zvegf4 cDNA is isolated by PCR using the polynucleotide sequence of SEQ ID NO: 1 with flanking regions at the 5' and 3' ends corresponding to the vector sequences flanking the zvegf4 insertion point. The primers for PCR each include from 5' to 3' end: 40 bp of flanking sequence from the vector and 17 bp corresponding to the amino and carboxyl termini from the open reading frame of zvegf4.

Ten µl of the 100 µl PCR reaction is run on a 0.8% LMP agarose gel (Seaplaque GTG) with 1×TBE buffer for analysis. The remaining 90 µl of PCR reaction is precipitated with the addition of 5 μl 1 M NaCl and 250 μl of absolute ethanol. The plasmid pZMP6, which has been cut with SmaI, is used for recombination with the PCR fragment. Plasmid pZMP6 was constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain. pZMP6 is a mammalian expression vector containing an expression cassette having the mouse metallothionein-1 promoter, multiple restriction sites for insertion of coding sequences, a stop codon, and a human growth hormone terminator. The plasmid also contains an $E.$ $coli$ origin of replication; a mammalian selectable marker expression unit comprising an SV40 promoter, enhancer and origin of replication, a DHFR gene, and the SV40 terminator; as well as the URA3 and CEN-ARS sequences required for selection and replication in $S.$ $cerevisiae$.

One hundred microliters of competent yeast cells ($S.$ $cerevisiae$) are independently combined with 10 μl of the various DNA mixtures from above and transferred to a 0.2-cm electroporation cuvette. The yeast/DNA mixtures are electropulsed at 0.75 kV (5 kV/cm), ∞ ohms, 25 μF. To each cuvette is added 600 μl of 1.2 M sorbitol, and the yeast is plated in two 300-μl aliquots onto two URA-D plates and incubated at 30° C. After about 48 hours, the Ura$^+$ yeast transformants from a single plate are resuspended in 1 ml $H_2O$ and spun briefly to pellet the yeast cells. The cell pellet is resuspended in 1 mil of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 μl acid-washed glass beads and 200 μl phenol-chloroform, vortexed for 1 minute intervals two or three times, and spun for 5 minutes in an Eppendorf centrifuge at maximum speed. Three hundred microliters of the aqueous phase is transferred to a fresh tube, and the DNA is precipitated with 600 μl ethanol (EtOH), followed by centrifugation for 10 minutes at 4° C. The DNA pellet is resuspended in 10 μl $H_2O$.

Transformation of electrocompetent $E.$ $coli$ host cells (ELECTROMAX DH10B™ cells; obtained from Life Technologies, Inc., Gaithersburg, Md.) is done with 0.5–2 ml yeast DNA prep and 40 μl of cells. The cells are electropulsed at 1.7 kV, 25 μF, and 400 ohms. Following electroporation, 1 ml SOC (2% BACTO™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) is plated in 250-μl aliquots on four LB AMP plates (LB broth (Lennox), 1.8% BACTO™ Agar (Difco), 100 mg/L Ampicillin).

Individual clones harboring the correct expression construct for zvegf4 are identified by restriction digest to verify the presence of the zvegf4 insert and to confirm that the various DNA sequences have been joined correctly to one another. The inserts of positive clones are subjected to sequence analysis. Larger scale plasmid DNA is isolated using a commercially available kit (QIAGEN Plasmid Maxi Kit, Qiagen, Valencia, Calif.) according to manufacturer's instructions. The correct construct is designated zvegf4/pZMP6.

Example 5

CHO DG44 cells (Chasin et al., *Som. Cell. Molec. Genet.* 12:555–566, 1986) are plated in 10-cm tissue culture dishes and allowed to grow to approximately 50% to 70% confluency overnight at 37° C., 5% $CO_2$, in Ham's F12/FBS media (Ham's F12 medium, Life Technologies), 5% fetal bovine serum (Hyclone, Logan, Utah), 1% L-glutamine (JRH Biosciences, Lenexa, Kans.), 1% sodium pyruvate (Life Technologies). The cells are then transfected with the plasmid zvegf4/pZMP6 by liposome-mediated transfection using a 3:1 (w/w) liposome formulation of the polycationic lipid 2,3-dioleyloxy-N-[2(sperminecarboxamido)ethyl]-N, N-dimethyl-1-propaniminium-trifluoroacetate and the neutral lipid dioleoyl phosphatidylethanolamine in membrane-filtered water (LIPOFECTAMINE™ Reagent, Life Technologies), in serum free (SF) media formulation (Ham's F12, 10 mg/ml transferrin, 5 mg/ml insulin, 2 mg/ml fetuin, 1% L-glutamine and 1% sodium pyruvate). Zvegf4/pZMP6 is diluted into 15-mil tubes to a total final volume of 640 μl with SF media. 35 μl of LIPOFECTAMINE™ is mixed with 605 μl of SF medium. The LIPOFECTAMINE™ mixture is added to the DNA mixture and allowed to incubate approximately 30 minutes at room temperature. Five ml of SF media is added to the DNA:LIPOFECTAMINE™ mixture. The cells are rinsed once with 5 ml of SF media, aspirated, and the DNA:LIPOFECTAMINE™ mixture is added. The cells are incubated at 37° C. for five hours, then 6.4 ml of Ham's F12/10% FBS, 1% PSN media is added to each plate. The plates are incubated at 37° C. overnight, and the DNA:LIPOFECTAMINE™ mixture is replaced with fresh 5% FBS/Ham's media the next day. On day 3 post-transfection, the cells are split into T-175 flasks in growth medium. On day 7 post-transfection, the cells are stained with FITC-anti-CD8 monoclonal antibody (Pharmingen, San Diego, Calif.) followed by anti-FITC-conjugated magnetic beads (Miltenyi Biotec, Auburn, Calif.). The CD8-positive cells are separated using commercially available columns (MiniMACS Separation Unit; Miltenyi Biotec) according to the manufacturer's directions and put into DMEM/Ham's F12/5% FBS without nucleosides but with 50 nM methotrexate (selection medium).

Cells are plated for subcloning at a density of 0.5, 1 and 5 cells per well in 96-well dishes in selection medium and allowed to grow out for approximately two weeks. The wells are checked for evaporation of medium and brought back to 200 μl per well as necessary during this process. When a large percentage of the colonies in the plate are near confluency, 100 μl of medium is collected from each well for analysis by dot blot, and the cells are fed with fresh selection medium. The supernatant is applied to a nitrocellulose filter in a dot blot apparatus, and the filter is treated at 100° C. in a vacuum oven to denature the protein. The filter is incubated in 625 mM Tris-glycine, pH 9.1, 5 mM β-mercaptoethanol, at 65° C., 10 minutes, then in 2.5% non-fat dry milk Western A Buffer (0.25% gelatin, 50 mM Tris-HCl pH 7.4, 150 mM NaCl, 5 mM EDTA, 0.05% Igepal CA-630) overnight at 4° C. on a rotating shaker. The filter is incubated with the anti-CD8 antibody-HRP conjugate in 2.5% non-fat dry milk Western A buffer for 1 hour at room temperature on a rotating shaker. The filter is then washed three times at room temperature in PBS plus 0.01% Tween 20, 15 minutes per wash. The filter is developed with chemiluminescence reagents (ECL™ direct labeling kit; Amersham Corp., Arlington Heights, Ill.) according to the manufacturer's directions and exposed to film (Hyperfilm ECL, Amersham) for approximately 5 minutes. Positive clones are trypsinized from the 96-well dish and transferred to 6-well dishes in selection medium for scaleup and analysis by Western blot.

Example 6

The protein coding region of zvegf4 is amplified by PCR using primers that add FseI and AscI restriction sites at the 5' and 3' termini, respectively. PCR primers are used with a template containing the full-length zvegf4 cDNA in a PCR reaction as follows: one cycle at 95° C. for 5 minutes; followed by 15 cycles at 95° C. for 1 min., 58° C. for 1 min., and 72° C. for 1.5 min.; followed by 72° C. for 7 min.; followed by a 4° C. soak. The PCR reaction product is loaded onto a 1.2% (low melt) (SEAPLAQUE GTG™; FMC, Rockland, Me.) gel in TAE buffer. The zvegf4 PCR product is excised from the gel and purified using a spin column containing a silica gel membrane (QLAQUICK™ Gel Extraction Kit; Qiagen, Inc., Valencia, Calif.) as per kit instructions. The PCR product is then digested, phenol/chloroform extracted, EtOH precipitated, and rehydrated in 20ml TE (Tris/EDTA pH 8). The zvegf4 fragment is then ligated into the cloning sites of the transgenic vector pHB12-8 and transformed into *E. coli* host cells (ELECTROMAX DH10B™ cells; obtained from Life Technologies, Inc., Gaithersburg, Md.) by electroporation. Clones containing zvegf4 DNA are identified by restriction analysis. A positive clone is confirmed by direct sequencing.

The zvegf4 cDNA is released from the pTG12-8 vector using FseI and AscI enzymes. The cDNA is isolated on a 1% low melt agarose gel, and is then excised from the gel. The gel slice is melted at 70° C., extracted twice with an equal volume of Tris buffered phenol, and EtOH precipitated. The DNA is resuspended in 10 µl $H_2O$.

The zvegf4 cDNA is cloned into the FseI-AscI sites of a modified pAdTrack CMV (He et al., *Proc. Natl. Acad. Sci. USA* 95:2509–2514, 1998). This construct contains a GFP marker gene. The CMV promoter driving GFP expression has been replaced with the SV40 promoter, and the SV40 polyadenylation signal has been replaced with the human growth hormone polyadenylation signal. In addition, the native polylinker has been replaced with FseI, EcoRV, and AscI sites. This modified form of pAdTrack CMV was named pZyTrack. Ligation is performed using a DNA ligation and screening kit (FAST-LINK™; Epicentre Technologies, Madison, Wis.). In order to linearize the plasmid, approximately 5 µg of the pZyTrack zvegf4 plasmid is digested with PmeI. Approximately 1 µg of the linearized plasmid is cotransformed with 200 ng of supercoiled pAdEasy (He et al., ibid.) into BJ5183 cells. The co-transformation is done using a Bio-Rad Gene Pulser at 2.5 kV, 200 ohms and 25 µF. The entire co-transformation is plated on 4 LB plates containing 25 µg/ml kanamycin. The smallest colonies are picked and expanded in LB/kanamycin, and recombinant adenovirus DNA identified by standard DNA miniprep procedures. Digestion of the recombinant adenovirus DNA with FseI-AscI confirms the presence of zvegf4 DNA. The recombinant adenovirus miniprep DNA is transformed into *E. coli* DH10B competent cells, and DNA is prepared therefrom.

Approximately 5 µg of recombinant adenoviral DNA is digested with PacI enzyme (New England Biolabs) for 3 hours at 37° C. in a reaction volume of 100 µl containing 20–30U of PacI. The digested DNA is extracted twice with an equal volume of phenol/chloroform and precipitated with ethanol. The DNA pellet is resuspended in 10 µl distilled water. A T25 flask of QBI-293A cells (Quantum Biotechnologies, Inc., Montreal, Canada), inoculated the day before and grown to 60–70% confluence, are transfected with the PacI digested DNA. The PacI-digested DNA is diluted up to a total volume of 50 µl with sterile HBS (150 mM NaCl, 20 mM HEPES). In a separate tube, 20 µl of 1 mg/ml N-[1-(2,3-Dioleoyloxy)propyl]-N,N,N-trimethyl-ammonium methylsulfate (DOTAP; Boehringer Mannheim) is diluted to a total volume of 100 µl with HBS. The DNA is added to the DOTAP, mixed gently by pipeting up and down, and left at room temperature for 15 minutes. The media is removed from the 293A cells and washed with 5 ml serum-free MEM-alpha (Life Technologies, Gaithersburg, Md.) containing 1 mM sodium pyruvate (Life Technologies), 0.1 mM MEM non-essential amino acids (Life Technologies) and 25 mM HEPES buffer (Life Technologies). 5 ml of serum-free MEM is added to the 293A cells and held at 37° C. The DNA/lipid mixture is added drop-wise to the T25 flask of 293A cells, mixed gently, and incubated at 37° C. for 4 hours. After 4 hours the media containing the DNA/lipid mixture is aspirated off and replaced with 5 ml complete MEM containing 5% fetal bovine serum. The transfected cells are monitored for Green Fluorescent Protein (GFP) expression and formation of foci (viral plaques).

Seven days after transfection of 293A cells with the recombinant adenoviral DNA, the cells expressing the GFP protein start to form foci. These foci are viral "plaques" and the crude viral lysate is collected by using a cell scraper to collect all of the 293A cells. The lysate is transferred to a 50 ml conical tube. To release most of the virus particles from the cells, three freeze/thaw cycles are done in a dry ice/ethanol bath and a 37° C. waterbath.

Ten 10-cm plates of nearly confluent (80–90%) 293A cells are set up 20 hours prior to infection. The crude lysate is amplified (primary amplification) to obtain a working "stock" of zvegf4 rAdV lysate. 200 ml of crude rAdV lysate is added to each 10-cm plate, and the plates are monitored for 48 to 72 hours looking for cytopathic effect (CPE) under the white light microscope and expression of GFP under the fluorescent microscope. When all of the 293A cells show CPE, this 1° stock lysate is collected, and freeze/thaw cycles performed as described above.

Secondary (2°) amplification of zvegf4 rAdV is obtained from twenty 15-cm tissue culture dishes of 80–90% confluent 293A cells. All but 20 ml of 5% MEM media is removed, and each dish is inoculated with 300–500 ml of 1° amplified rAdv lysate. After 48 hours the 293A cells are lysed from virus production, the lysate is collected into 250 ml polypropylene centrifuge bottles, and the rAdV is purified.

NP-40 detergent is added to a final concentration of 0.5% to the bottles of crude lysate to lyse all cells. Bottles are placed on a rotating platform for 10 minutes and agitated as fast as possible. The debris is pelleted by centrifugation at 20,000×G for 15 minutes. The supernatant is transferred to 250-ml polycarbonate centrifuge bottles, and 0.5 volume of 20% PEG8000/2.5M NaCl solution is added. The bottles are shaken overnight on ice. The bottles are centrifuged at 20,000×G for 15 minutes, and the supernatants are discarded into a bleach solution. A white precipitate (precipitated virus/PEG) forms in two vertical lines along the walls of the bottles on either side of the spin mark. Using a sterile cell scraper, the precipitate from 2 bottles is resuspended in 2.5 ml PBS. The virus solution is placed in 2-mil microcentrifuge tubes and centrifuged at 14,000×G in a microcentrifuge for 10 minutes to remove any additional cell debris. The supernatants from the 2-ml microcentrifuge tubes are transferred into a 15-ml polypropylene snapcap tube and adjusted to a density of 1.34 g/ml with CsCl. The volume of the virus solution is estimated, and 0.55 g/ml of CsCl added. The CsCl is dissolved, and 1 ml of this solution weighed. The solution is transferred to polycarbonate, thick-walled, 3.2 ml centrifuge tubes (Beckman) and spun at 348,000×G for 3–4 hours at 25° C. The virus forms a white band. Using wide-bore pipette tips, the virus band is collected.

The virus from the gradient will have a large amount of CsCl, which must be removed before it can be used on cells. Pharmacia PD-10 columns prepacked with SEPHADEX® G-25M (Pharmacia) are used to desalt the virus preparation. The column is equilibrated with 20 ml of PBS. The virus is loaded and allowed to run into the column. 5 ml of PBS is added to the column, and fractions of 8–10 drops collected. The optical density of 1:50 dilutions of each fraction is determined at 260 nm on a spectrophotometer, and a clear absorbance peak is identified. These fractions are pooled, and the optical density (OD) of a 1:25 dilution is determined. OD is converted into virus concentration using the formula (OD at 260nm)(25)(1.1×10$^{12}$)=virions/ml.

To store the virus, glycerol is added to the purified virus to a final concentration of 15%, mixed gently and stored in aliquots at −80° C.

A protocol developed by Quantum Biotechnologies, Inc. (Montreal, Canada) is followed to measure recombinant virus infectivity. Briefly, two 96-well tissue culture plates are seeded with 1×10$^4$ 293A cells per well in MEM containing 2% fetal bovine serum for each recombinant virus to be assayed. After 24 hours, 10-fold dilutions of each virus from 1×10$^{-2}$ to 1×10$^{-14}$ are made in MEM containing 2% fetal bovine serum. 100 μl of each dilution is placed in each of 20 wells. After 5 days at 37° C., wells are read either positive or negative for CPE and PFU/ml is calculated.

TCID$_{50}$ formulation used is as per Quantum Biotechnologies, Inc., above. The titer (T) is determined from a plate where virus used is diluted from 10$^{-2}$ to 10$^{-4}$, and read 5 days after the infection. At each dilution a ratio (R) of positive wells for CPE per the total number of wells is determined. The titer of the undiluted sample is T=10$^{(1+F)}$=TCID$_{50}$/ml, where F=1+d(S−0.5), S is the sum of the ratios (R), and d is Log$_{10}$ of the dilution series (e.g., d=1 for a ten-fold dilution series). To convert TCID$_{50}$/ml to pfu/ml, 0.7 is subtracted from the exponent in the calculation for titer (T).

Example 7

Recombinant zvegf4 having a carboxyl-terminal Glu-Glu affinity tag was produced in a baculovirus expression system according to conventional methods. The culture was harvested, and the cells were lysed with a solution of 0.02 M Tris-HCl, pH 8.3, 1 mM EDTA, 1 mM DTT, 1 mM 4-(2-Aminoethyl)-benzenesulfonyl fluoride hydrochloride (PEFABLOC® SC; Boehringer-Mannheim), 0.5 μM aprotinin, 4 mM leupeptin, 4 mM E-64, 1% NP-40 at 4° C. for 15 minutes on a rotator. The solution was centrifuged, and the supernatant was recovered. Twenty ml of extract was combined with 50 μl of anti-Glu-Glu antibody conjugated to SEPHAROSE® beads in 50 μl buffer. The mixture was incubated on a rotator at 4° C. overnight. The beads were recovered by centrifugation and washed 3×15 minutes at 4° C. Pellets were combined with sample buffer containing reducing agent and heated at 98° C. for five minutes. The protein was analyzed by polyacrylamide gel electrophoresis under reducing conditions followed by western blotting on a PVDF membrane using an antibody to the affinity tag. Two bands were detected, one a M$_r$≈49 kD and the other at M$_r$≈21 kD. Sequence analysis showed the larger band to comprise two sequences, one beginning at Arg-19 of SEQ ID NO:2 and the other beginning at Asn-35 of SEQ ID NO:2. The asparagine residue appeared to have been deamidated to an aspartic acid. The smaller band began at Ser-250 of SEQ ID NO:2.

Example 8

The zvegf4 cDNA was cloned into the EcoRV-AscI sites of a modified pAdTrack-CMV (He et al., Proc. Natl. Acad. Sci. USA 95:2509–2514, 1998). This construct contains the green fluorescent protein (GFP) marker gene. The CMV promoter driving GFP expression was replaced with the SV40 promoter, and the SV40 polyadenylation signal was replaced with the human growth hormone polyadenylation signal. In addition, the native polylinker was replaced with FseI, EcoRV, and AscI sites. This modified form of pAdTrack-CMV was named pZyTrack. Ligation was performed using a commercially available DNA ligation and screening kit (FAST-LINK™ kit; Epicentre Technologies, Madison, Wis.).

Zvegf4 was assayed in an aortic ring outgrowth assay (Nicosia and Ottinetti, ibid.; Villaschi and Nicosia, ibid.). Thoracic aortas were isolated from 1–2 month old SD male rats and transferred to petri dishes containing HANK's buffered salt solution. The aortas were flushed with additional HANK's buffered salt solution to remove blood, and adventitial tissue surrounding the aorta was carefully removed. Cleaned aortas were transferred to petri dishes containing EBM basal media, serum free (Clonetics, San Diego, Calif.). Aortic rings were obtained by slicing approximately 1-mm sections using a scalpel blade. The ends of the aortas used to hold the aorta in place were not used. The rings were rinsed in fresh EBM basal media and placed individually in a wells of a 24-well plate coated with basement membrane matrix (MATRIGEL®; Becton Dickinson, Franklin Lakes, N.J.). The rings were overlayed with an additional 50 μl of the matrix solution and placed at 37° C. for 30 minutes to allow the matrix to gel. Test samples were diluted in EBM basal serum-free media supplemented with 100 units/ml penicillin, 100 μg/ml streptomycin and HEPES buffer and added at 1 ml/well. Background control was EBM basal serum-free media alone. Basic FGF (R&D Systems, Minneapolis, Minn.) at 20 ng/ml was used as a positive control. Zvegf4 adenovirus was added to wells, assuming a cell count of 500,000 cells and a multiplicity of infection of 5000 particles/cell. A null adenovirus (designated "zPar") was used as a control. Samples were added in a minimum of quadruplets. Rings were incubated for 5–7 days at 37° C. and analyzed for growth. Aortic outgrowth was scored by multiple, blinded observers using 0 as no growth and 4 as maximum growth. Zvegf4 adenovirus produced a significant increase in outgrowth, comparable to the most potent control (bFGF).

Example 9

Polyclonal anti-peptide antibodies were prepared by immunizing 2 female New Zealand white rabbits with the peptides huzvegf4-1 (CGHKEVPPRIKSRTNQIK; SEQ ID NO:39), huzvegf4-2 (ESWQEDLENMYLDTPRYRGRSY HDC; SEQ ID NO:40), or huzvegf4-3 (CFEPGHIKRRGRAKTMALVDIQLD; SEQ ID NO:41). The peptides were synthesized using an Applied Biosystems Model 431A peptide synthesizer (Applied Biosystems, Inc., Foster City, Calif.) according to the manufacturer's instructions. The peptides were conjugated to keyhole limpet hemocyanin (KLH) with maleimide activation. The rabbits were each given an initial intraperitoneal (ip) injection of 200 μg of peptide in Complete Freund's Adjuvant followed by booster ip injections of 100 µg peptide in Incomplete Freund's Adjuvant every three weeks. Seven to ten days after the administration of the second booster injection (3 total injections), the animals were bled, and the sera were collected. The animals were then boosted and bled every three weeks.

The zvegf4 peptide-specific rabbit sera were characterized by an ELISA titer check using 1 µg/ml of the peptide used to make the antibody as an antibody target. The 2 rabbit sera to the huzvegf4–1 peptide had titer to their specific peptide at a dilution of 1:5,000,000. The 2 rabbit sera to the huzvegf4-2 peptide had titer to their specific peptide at a dilution of 1:5,000,000. The 2 rabbit seras to the huzvegf4-3 peptide had titer to their specific peptide at a dilution of 1:500,000.

The zvegf4 peptide-specific polyclonal antibodies were affinity purified from the sera using CNBr-SEPHAROSE 4B protein columns (Pharmacia LKB) that were prepared using 10 mg of the specific peptide per gram CNBr-SEPHAROSE, followed by 20×dialysis in PBS overnight. Zvegf4-specific antibodies were characterized by an ELISA titer check using 1 µg/ml of the appropriate peptide antigens as antibody targets. The lower limit of detection (LLD) of the anti-huzvegf4-1 affinity purified antibody on its specific antigen (huzvegf4-1 peptide) was a dilution of 0.1 pg/ml. The LLD of the anti-huzvegf4-2 affinity purified antibody on its specific antigen (huzveg4-2 peptide) was a dilution of 5 ng/ml. The LLD of the rabbit anti-huzvegf4-3 affinity purified antibody on its specific antigen (huzvegf4-3 peptide) was a dilution of 5 ng/ml.

Example 10

Recombinant carboxyl-terminal Glu-Glu tagged zvegf4 (zvegf4-cee) was produced from recombinant baculovirus-infected insect cells. Two-liter cultures were harvested, and the media were sterile-filtered using a 0.2 µm filter.

Protein was purified from the conditioned media by a combination of anti-Glu-Glu (anti-EE) peptide antibody affinity chromatography and S-200 gel exclusion chromatography. Culture media (pH 6.0, conductivity 7 mS) was directly loaded onto a 20×80 mm (25-ml bed volume) anti-EE antibody affinity column at a flow of 6 ml/minute. The column was washed with ten column volumes of PBS, then bound protein was eluted with two column volumes of 0.4 mg/ml EYMPTD peptide (SEQ ID NO:42) (Princeton BioMolecules Corp., Langhorne, Pa.). Five-ml fractions were collected. Samples from the anti-EE antibody affinity column were analyzed by SDS-PAGE with silver staining and western blotting (as disclosed below) for the presence of zvegf4-cee. Zvefg4-cee-containing fractions were pooled and concentrated to 3.8 ml by filtration using a Biomax™-5 concentrator (Millipore Corp., Bedford, Mass.), and loaded onto a 16×1000 mm gel filtration column (SEPHACRYL™ S-200 HR; Amersham Pharmacia Biotech, Piscataway, N.J.). The fractions containing purified zvegf4-cee were pooled, filtered through a 0.2 µm filter, aliquoted into 100 µl each, and frozen at −80° C. The concentration of the final purified protein was determined by colorimetric assay (BCA assay reagents; Pierce, Rockford, Ill.) and HPLC-amino acid analysis.

Recombinant zvegf4-cee was analyzed by SDS-PAGE (NuPAGE™ 4–12% gel; Novex, San Diego, Calif.) with silver staining (FASTSILVER™, Geno Technology, Inc., Maplewood, Mo.) and Western blotting using antibodies to the huzvegf4-1, huzvegf4-2, and huzvefg4-3 peptides, and anti-EE antibody. Either the conditioned media or purified protein was electrophoresed using an electrophoresis mini-cell (XCELL II™ mini-cell; Novex, San Diego, Calif.) and transferred to nitrocellulose (0.2 µm; Bio-Rad Laboratories, Hercules, Calif.) at room temperature using an XCELL II™ blot module (Novex) with stirring according to directions provided in the instrument manual. The transfer was run at 500 mA for one hour in a buffer containing 25 mM Tris base, 200 mM glycine, and 20% methanol. The filters were then blocked with 10% non-fat dry milk in PBS for 10 minutes at room temperature. The nitrocellulose was quickly rinsed, then primary antibody was added in PBS containing 2.5% non-fat dry milk. The blots were incubated for two hours at room temperature or overnight at 4° C. with gentle shaking. Following the incubation, blots were washed three times for 10 minutes each in PBS. Secondary antibody (goat anti-rabbit IgG conjugated to horseradish peroxidase; obtained from Rockland Inc., Gilbertsville, Pa.) diluted 1:2000 in PBS containing 2.5% non-fat dry milk was added, and the blots were incubated for two hours at room temperature with gentle shaking. The blots were then washed three times, 10 minutes each, in PBS, then quickly rinsed in $H_2O$. The blots were developed using commercially available chemiluminescent substrate reagents (SUPERSIGNAL® ULTRA reagents 1 and 2 mixed 1:1; reagents obtained from Pierce), and the signal was captured using image analysis software (LUMI-IMAGER™ Lumi Analyst 3.0; Roche Molecular Biochemicals, Indianapolis, Ind.) for times ranging from 10 seconds to 5 minutes or as necessary.

The purified zvefg4-cee appeared as a single band at about 85 kDa under non-reducing conditions with silver staining, but at about 50 kDa under reducing conditions, suggesting a dimeric form of zvefg4-cee under non-reducing conditions.

Using either 4-1, 4-3 or anti-EE antibody, the purified zvegf4-cee showed the same result as silver staining gel; the 4-3 antibody gave a much weaker signal. However, in addition to recognizing the 85-kDa band under non-reducing conditions and the 50-kDa band under reducing conditions, the 4-2 antibody recognized two bands at 35 kDa and 32 kDa under non-reducing conditions, and two bands at 38 kDa and 35 kDa under reducing conditions. While not wishing to be bound by theory, the smaller bands are likely to be cleaved forms of zvefg4-cee missing the N-terminal portion of the protein that is recognized by the 4-1 antibody.

Example 11

Recombinant zvegf4 was analyzed for mitogenic activity on rat liver stellate cells (obtained from N. Fausto, University of Washington), human aortic smooth muscle cells (Clonetics Corp., Walkersville, Md.), human retinal pericytes (Clonetics Corp.) and human hepatic fibroblasts (Clonetics Corp.). Test samples consisted of conditioned media (CM) from adenovirally infected HaCaT human keratinocyte cells (Boukamp et al., *J. Cell. Biol.* 106:761–771, 1988; Skobe and Fusenig, *Proc. Natl. Acad. Sci. USA* 95:1050–1055, 1998; obtained from Dr. Norbert E. Fusenig, Deutsches Krebsforschungszentrum, Heidelberg, Germany) expressing full length zvegf-4. Control CM was generated from HaCaT cells infected with a parental GFP-expressing adenovirus (zPar). The CM were concentrated 10-fold using a 15 ml centrifugal filter device with a 10K membrane filter (Ultrafree®; Millipore Corp., Bedford, Mass.), then diluted back to 1× with ITS media (serum-free DMEM/Ham's F-12 medium containing 5 µg/ml insulin, 20 µg/ml transferrin, and 16 pg/ml selenium). Cells were plated at a density of 2,000 cells/well in 96-well culture plates and grown for approximately 72 hours in DMEM containing 10% fetal calf serum at 37° C. Cells were quiesced by incubating them for approximately 20 hours in serum-free DMEM/Ham's F-12 medium containing insulin (5 µg/ml), transferrin (20 µg/ml), and selenium (16 pg/ml) (ITS). At the time of the assay, the medium was removed, and test samples were added to the wells in triplicate. For measurement of [$^3$H]thymidine incorporation, 20 µl of a 50 µCi/ml stock in DMEM was added directly to the cells, for a final activity of 1 µCi/well. After another 24-hour incubation, media were removed and cells were incubated with 0.1 ml of trypsin until cells detached. Cells were harvested onto 96-well filter plates using a sample harvester (FILTERMATE™ harvester; Packard Instrument Co., Meriden, Conn.). The plates were then dried at 65° C. for 15 minutes, sealed after adding 40 µl/well scintillation cocktail (MICROSCINT™ O; Packard Instrument Co.) and counted on a microplate scintillation counter (TOPCOUNT®; Packard Instrument Co.). Results, presented in Table 8, demonstrated that zvegf4 CM had approximately 7-fold higher mitogenic activity than control CM on pericytes cells and approximately a 1.5–2.4-fold higher mitogenic activity on the other cell types tested.

TABLE 8

|  | CPM incorporated | | | |
| --- | --- | --- | --- | --- |
|  | Zvegf4 (1 × CM) | | zPar (1 × CM) | |
| Sample | Mean | St. dev. | Mean | St. dev. |
| Human retinal pericytes | 3621 | 223 | 523 | 306 |
| Human hepatic fibroblasts | 7757 | 753 | 3232 | 264 |
| Human aortic SMC | 2009 | 37 | 1263 | 51 |
| Rat liver stellate cells | 34707 | 1411 | 14413 | 1939 |

Example 12

Recombinant, C terminal glu-glu tagged zvegf4 was analyzed for mitogenic activity on human aortic smooth muscle cells (HAoSMC) (Clonetics), human retinal pericytes (Clonetics) and human aortic adventitial fibroblasts (AoAF) (Clonetics). Cells were plated at a density of 2,000 cells/well in 96-well culture plates and grown for approximately 72 hours in DMEM containing 10% fetal calf serum at 37° C. Cells were quiesced by incubating them for 20 hours in ITS medium. At the time of the assay, the medium was removed, and test samples were added to the wells in triplicate. Test samples consisted of purified, full-length, tagged zvegf4 expressed in baculovirus-infected cells. Purified protein in a buffer containing 0.1% BSA was serially diluted into ITS medium at concentrations of 1 µg/ml to 1 ng/ml and added to the test plate. A control buffer of 0.1% BSA was diluted identically to the highest concentration of zvegf4 protein and added to the plate. For measurement of [$^3$H]thymidine incorporation, 20 µl of a 50 µCi/ml stock in DMEM was added directly to the cells, for a final activity of 1 µCi/well. After another 24-hour incubation, mitogenic activity was assessed by measuring the uptake of [$^3$H] thymidine. Media were removed, and cells were incubated with 0.1 ml of trypsin until cells detached. Cells were harvested onto 96-well filter plates using a sample harvester (FILTERMATE™ harvester; Packard Instrument Co., Meriden, Conn.). The plates were then dried at 65° C. for 15 minutes, sealed after adding 40 µl/well scintillation cocktail (MICROSCINT™ O; Packard Instrument Co.) and counted on a microplate scintillation counter (TOPCOUNT®; Packard Instrument Co.). Results, presented in Table 9, demonstrated that 80 ng/ml zvegf4 had approximately 1.7-fold higher mitogenic activity on pericytes, 3.2-fold higher activity on aortic SMCs, and 2.6-fold higher activity on aortic fibroblasts as compared to the buffer control.

TABLE 9

|  | CPM Incoporated | | | | | |
| --- | --- | --- | --- | --- | --- | --- |
|  | Pericytes | | HAoSMC | | AoAF | |
| Sample | Mean | St. dev. | Mean | St. dev. | Mean | St. dev. |
| Zvegf4, 80 ng/ml | 96.7 | 18.2 | 488.7 | 29.6 | 177.0 | 1.0 |
| Zvegf4, 20 ng/ml | 81.7 | 11.7 | 211.7 | 50.8 | 107.7 | 20.1 |
| Zvegf4, 5 ng/ml | 67.3 | 6.7 | 191.7 | 4.5 | 123.7 | 10.5 |
| Buffer control | 58.7 | 8.5 | 152.3 | 40.1 | 68.7 | 8.3 |

Example 13

Mice (C57BL6) were infected with a zvegf4-encoding adenovirus vector (AdZyvegf4) to determine the effects on serum chemistry, complete blood counts (CBC), body and organ weight changes, and histology. On day −1, the mice were tagged, individually weighed, and group normalized for separation into treatment groups (4 mice per cage). Group 1 mice (n=8 females, 7 males) received GFP (control) adenovirus, 1×10$^{11}$ particles. Group 2 mice (n=8 females, 6 males) received zvegf4 adenovirus, 1×10$^{11}$ particles. Group 3 mice (n=8 females, 8 males) were untreated controls. On day 0, the mice received injections of the appropriate adenovirus solution. On day 10, blood was collected (under ether anesthesia) for CBCs and clinical chemistry measurements. On day 20, mice were weighed and sacrificed by cervical dislocation after collecting blood (under ether anesthesia) for CBCs and clinical chemistry measurements. Tissues were collected for histopathology. Observations were as follows:

Serum chemistry changes: AdZyvegf4 treated mice were hypoglycemic. This effect increased in magnitude over time (day 10 vs. day 20). Serum cholesterol levels were significantly increased (2-fold) at both time points. Serum levels of albumin and the enzymes ALT, AST and alkaline phosphatase were all significantly increased in AdZyvegf4 treated mice. Serum calcium and total bilirubin were also significantly increased, and became more elevated over time.

CBC changes: AdZyvegf4-treated mice had significantly higher lymphocyte count at both time points (mean>10). Platelet counts were significantly lower at day 20. Red blood cell count was significantly higher in females at day 10, significantly higher in males at day 20.

Body/organ weights: AdZyvegf4-treated males lost weight over the course of the experiment. This result was significantly different than control animals, which gained weight. There was no difference among the female mice; all groups gained similar weight. Spleen weight was significantly greater (approximately 4-fold) in all AdZyvegf4-treated mice. Liver weight was also significantly greater in all AdZyvegf4-treated mice. There was no significant difference in kidney weight between groups.

Histology: In the liver, proliferation of sinusoidal endothelial cells was observed. In the spleen, proliferation of reticuloendothelial cells was observed. In the kidney, proliferative glomerulopathy was observed. While not wishing to be bound by theory, this glomerulopathy may have been due to proliferation of capillary endothelial cells. In the femurs, there was proliferation of endosteal bone (mostly in trabecular bone), which in some cases replaced most of the bone marrow. Proliferation of stromal cells was also observed in bone. In the lung, there was increased frequency of brochoaveolar lymphoid tissue.

Example 14

90 µg of recombinant zvegf4 protein was dissolved in 500 µl PBS containing 2 mCi Na-$^{125}$I (Amersham Corp.). One derivatized, nonporous polystyrene bead (IODO-BEADS®; Pierce, Rockford, Ill.) was added, and the reaction mixture was incubated one minute on ice. The iodinated protein was separated from unincorporated $^{125}$I by gel filtration using an elution buffer of 10% acetic acid, 150 mM NaCl, and 0.25% gelatin. The active fraction contained 29 µg/ml $^{125}$I-zvegf4 with a specific activity of $3.0 \times 10^4$ cpm/ng.

The following cell lines were plated into the wells of a 24-well tissue culture dish and cultured in growth medium for three days:

1. Human retinal pericytes, passage 6 (pericytes).
2. Rat stellate cells, passage 8.
3. Human umbilical vein endothelial cells, passage 4 (HUVEC).
4. Human aortic adventicial fibroblasts, passage 5 (AoAF).
5. Human aortic smooth muscle cells, passage 2 (AoSMC).

Cells were washed once with ice-cold binding buffer (HAM'S F-12 containing 2.5 mg/ml BSA, 20 mM HEPES, pH 7.2), then 250 µl of the following solutions was added to each of three wells of the culture dishes containing the test cells. Binding solutions were prepared in 5 mL of binding buffer with 250 pM $^{125}$I-zvegf4 and:

1. No addition.
2. 25 nM zvegf4.
3. 25 nM zvegf3.
4. 25 nM PDGF-AA.
5. 25 nM PDGF-BB The reaction mixtures were incubated on ice for 2 hours, then washed three times with one ml of ice-cold binding buffer. The bound $^{125}$I-zvegf4 was quantitated by gamma counting a Triton-X 100 extract of the cells.

Results, shown in Table 10, indicate binding of zvegf4 to pericytes, stellate cells, AoAF, and AoSMC, but not to HUVEC. The first column represents total CPM $^{125}$I-zvegf4 bound/well. The second column is $^{125}$I-zvegf4 bound/well when blocked with cold ligand. The difference between the two numbers represents specific binding.

TABLE 10

| Cell Type | $^{125}$I-zvegf4 Bound (CPM) | $^{125}$I-zvegf4 Bound w/cold zvegf4 (CPM) |
|---|---|---|
| 1. Pericytes | 3083 +/− 864 | 623 +/− 60 |
| 2. Stellate Cells | 2131 +/− 450 | 413 +/− 164 |
| 3. HUVEC | 485 +/− 91 | 227 +/− 13 |
| 4. AoAF | 1544 +/− 131 | 300 +/− 15 |
| 5. AoSMC | 1628 +/− 203 | 440 +/− 46 |

Example 15

The zvegf4 gene was mapped to human chromosome 11 using the commercially available version of the Stanford G3 Radiation Hybrid Mapping Panel (Research Genetics, Inc., Huntsville, Ala.). This panel contains PCRable DNAs from each of 83 radiation hybrid clones of the whole human genome, plus two control DNAs (the RM donor and the A3 recipient). A publicly available WWW server (http://shgc-www.stanford.edu) allows chromosomal localization of markers. 20-µl reaction mixtures were set up in a PCRable 96-well microtiter plate (Stratagene, La Jolla, Calif.) and used in a thermal cycler (ROBOCYCLER® Gradient 96; Stratagene). Each of the 85 PCR mixtures consisted of 2 µl buffer (10×KlenTaq PCR reaction buffer, Clontech Laboratories, Inc., Palo Alto, Calif.), 1.6 µl dNTPs mix (2.5 mM each, PERKIN-ELMER, Foster City, Calif.), 1 µl sense primer, ZC22,685 (SEQ ID NO:37), 1 µl antisense primer, ZC22,686 (SEQ ID NO:38), 2 µl of a density increasing agent and tracking dye (RediLoad, Research Genetics, Inc., Huntsville, Ala.), 0.4 µl of a commercially available DNA polymerase/antibody mix (50×ADVANTAGE™ KlenTaq Polymerase Mix, obtained from Clontech Laboratories, Inc., Palo Alto, Calif.), 25 ng of DNA from an individual hybrid clone or control, and x µl ddH2O for a total volume of 20 µl. The reaction mixtures were overlaid with an equal amount of mineral oil and sealed. The PCR cycler conditions were an initial 5-minute denaturation at 94° C.; 35 cycles of 45 seconds denaturation at 94° C., 45 seconds annealing at 64° C. and 75 seconds extension at 72° C.; followed by a final extension for 7 minutes at 72° C. The reaction products were separated by electrophoresis on a 2% agarose gel. The results showed linkage of zvegf4 to the human chromosome 11 framework marker SHGC-34226 with a LOD score of 14.90 and at a distance of 0 cR__10000 from the marker. The use of surrounding genes/markers positions Zvegf4 in the 11q22.3-q23.1 chromosomal region.

Example 16

The structure of recombinant zvegf4 was analyzed by Western blotting using conventional techniques. Protein produced in the HaCaT human keratinocyte cell line was electrophoresed under reducing and non-reducing conditions, transferred to filters, and probed with antibodies to the interdomain and CUB domain regions of the protein. Reduced protein appeared as a single band having an apparent $M_r$ of approximately 53 kD, consistent with a glycosylated, monomeric protein. Non-reduced protein appeared as a single band having an apparent $M_r$ of approximately 85 kD, consistent with a disulfide-1inked dimer.

Example 17

An expression plasmid containing full-length zvegf4 was constructed, using the expression vector pEZE2. pEZE2 is derived from pDC312 by the addition of additional restriction enzyme recognition sites to the multiple cloning site. pDC312 and pEZE2 contain an EASE segment, as described in WO 97/25420, which can improve expression of recombinant proteins two to eight fold in mammalian cells, preferably Chinese Hamster Ovary (CHO) cells. The pEZE2 expression unit contains the CMV enhancer/promoter, the adenovirus tripartite leader sequence, a multiple cloning site for insertion of the coding region for the recombinant protein, an encephalomyocarditis virus internal ribosome entry site, a coding segment for mouse dihydrofolate reductase, and the SV40 transcription terminator. In addition, pEZE2 contains an E. coli origin of replication and a bacterial beta-lactamase gene.

A zvegf4 DNA fragment was generated by PCR (Advantage2 PCR Kit, Clontech, Palo Alto, Calif.) with 5°

FseI and 3' AscI sites for direct cloning into the expression vector. The 5' primer contained an FseI site, Kozak sequence, and the first 21 basepairs of the native leader sequence for zvegf4 (ZC26,136; SEQ ID NO:43). The 3' primer contained the last 21 basepairs of zvegf4, a stop codon, and an AscI site (ZC26,137; SEQ ID NO:44). The PCR reaction included 1 mL of template (ESTEP plasmid zvegf4pcrfl#3) and was run as follows: 94° C., 1 minute, I cycle; then 25 cycles of 94° C., 30 seconds; 55° C., 30 seconds; 68° C., 1 minute; then a final extension cycle of 72° C. for 7 minutes.

The ESTEP plasmid zvegf4pcrfl#3 contains the full-length human zvegf4 fragment. This fragment was generated by PCR using 20 pm each of ZC22,341 (SEQ ID NO:45) and ZC22,342 (SEQ ID NO:46) primers and 3 mL of a thyroid library. The reaction was run as follows: 94° C., 1 minute, 1 cycle; then 30 cycles of 94° C., 20 seconds; 66° C., 1.5 minutes; then a final extension cycle of 72° C. for 5 minutes. The 1,272 bp product was gel purified on a 1% TBE gel, and the DNA was extracted from the gel slab using the QIAquick Gel Extraction Kit (Qiagen, Valencia, Calif.). This 1,272 bp fragment was subcloned into pCR2.1 vector (Invitrogen, Carlsbad, Calif.), and designated zvegf4pcrfl#3.

The PCR generated fragment was purified (Qiaquick PCR clean-up kit, Qiagen, Valencia, Calif.) and digested with restriction enzymes AscI and FseI (New England Biolabs, Beverly, Mass.) in a single 100 mL reaction. Five micrograms of the expression vector pEZE2 were also digested with FseI and AscI in a single 100 mL reaction. The digested DNA was fractionated by agarose gel electrophoresis and the DNA fragments were isolated and purified (Qiaquick Gel Extraction Kit, Qiagen).

Five microliters of the zvegf4 DNA fragment and 1 mL of the pEZE2 vector fragment were ligated overnight at room temperature (New England Biolabs High Concentrated Ligase and supplied buffer). One microliter of the ligation reaction was added to 25 mL of electrocompetant E. coli strain DH10B (Life Technologies) in a 0.2 cm cuvette. The mixture was electroporated (BioRad E. coli Pulser) at 2.3 kv. To the cuvette, 1 mL of LB broth was added, and 100 mL of the mix was plated onto LB/Ampicillin agar plates. The plates were incubated overnight at 37° C., and 8 isolated colonies were picked for DNA mini prep (Qiaquick Mini-Prep Kit, Qiagen). Individual clones were screened by PCR for the presence of zvegf4 DNA, using the above-mentioned primers. DNA sequencing was performed on clones #1–6, to verify the correct full-length sequence. One clone contained the correct expected sequence and a Maxi prep of DNA was made (Qiagen Plasmid Maxi Kit, Qiagen).

CHO DG44 (Chasin et al., Som. Cell. Molec. Genet. 12:555–666, 1986) were plated and allowed to grow to approximately 50% to 70% confluency over night at 37° C. in MEM alpha media (JRH Biosciences, Lenexa, Kans.), 7.5% fetal bovine serum (Hyclone, Logan, Utah), 1% L-glutamine (Life Technologies), 1% sodium pyruvate (Life Technologies), 1% HT solution (Life Technologies), and 1% Penicillin/Streptomycin (Life Technologies). The cells were then transfected with the plasmid pEZE2/zvegf4 by liposome-mediated transfection, using a 10:1 (w/w) liposome formulation of the polycationic lipid dioctaldecylamidoglycyl spermine, in serum-free (SF) medium formulation DMEMIF12 - Life Technologies, Non-Essential Amino Acids-Life Technologies, 1% L-glutamine, 1% sodium pyruvate. The plasmid pEZE2/zvegf4 was diluted in a final volume of 500 mL of SF medium in a 15 mL conical tube, and 20 mL of Transfectam (Promega, Madison, Wis.) reagent was added, mixed well and incubated at room temperature for 10 minutes. After incubation, 4.5 mL of SF medium was added to the DNA mixture and mixed well using a 5 mL pipette. The cells were rinsed 3 times with SF medium, and the 5 mL of DNA solution was overlayed upon the cell monolayer. The cells were incubated at 37° C., 5% $CO_2$ for 2 hours. Then 6 mL of complete medium (MEM alpha, 7.5% FBS, 1% L-glutamine, 1% sodium pyruvate, 1% HT, 1% Pen/Strep) and the cells were incubated for a further 48 hours. After 48 hours, the cells were trypsinized from the plate with 1 mL of 0.25% Trypsin/1 mM EDTA (Life Technologies) and quenched with 4 mL of complete medium without nucleosides (MEM alpha, 7.5% Dialysed FBS, 1% L-glutamine, 1% sodium pyruvate, 1% Pen/Strep). Five hundred microliters of the cell suspension were transferred to plates containing 10 mL of complete medium without nucleosides. The cultures were grown for 14 days, until single colonies that were approximately 0.25 cm in diameter were present. Cloning rings (Bellco Glass, Inc., Vineland, N.J.) were used to isolate 24 single colonies, which were removed with trypsin, transferred to 6 well cell cluster plates (Costar, Corning, N.Y.), and incubated 4 days.

The cell wells were rinsed with SF medium and 2 mL of SF medium was added, and the culture was incubated for 24 hours. The conditioned SF medium was concentrated approximately 20-fold using a 10K centrifuge device (Millipore Corporation, Bedford, Mass.). Twenty-five microliters of the concentrate was added to 15 mL of 4×Sample Buffer (Novex, San Diego, Calif.) with 50 mM beta-Mercaptoethanol, and the mixture was run on a 4–12% NuPAGE gel (Novex). The proteins from the gel were transferred to nitrocellulose membranes (Novex) and the blot was blocked with 10% non-fat dry milk in Western A (0.25% gelatin, 50 mM Tris-HCl pH 7.4, 150 mM NaCl, 5 mM EDTA, 0.05% Igepal CA-630) overnight at room temperature on a rotating shaker platform. The membrane was rinsed 3 times in Western A. An antibody to the N-terminus of the zvegf4 protein was diluted at 1:3000 in 50 mL 5% non-fat milk in Western A. The antibody solution was overlayed on the membrane and incubated at room temperature on a rocking platform for 1 hour. After the 1 hour incubation, the solution was discarded and the membrane rinsed 3 times with Western A and once with Western B (50 mM Tris pH 7.4, 5 mM EDTA, 0.05% Igepal CA-630, 1 M NaCl, 0.25% Gelatin). The secondary antibody, an F(ab')$_2$ fragment of Donkey-Anti-Rabbit-HRP (Amersham Corp., Arlington Heights, Ill.), was diluted in Western A at 1:3000, overlayed on the membrane, and incubated 1 hour at room temperature on a rocking platform. The secondary antibody solution was discarded, and the membrane was washed 3 times in Western A and 3 times in Western B. Chemiluminescence was used to detect the full-length or protease-digested N-terminus of zvegf4 according to the manufacturer's instructions (Pierce, Rockford, Ill.), and was analysed by LumiAnalyser (Roche/Boehringer Mannheim, Mannheim, Germany). Four of the 12 clones were positive for zvegf4, and numbers 7 and 12 were trypsinized and transferred to T175 flasks (Costar, Corning, N.Y.) in complete medium without nucleosides.

Example 18

An expression construct encoding the growth factor domain of zvegf4 is prepared. A PCR fragment was generated (Clontech Advantage 2 PCR Kit) that contained a 5' BamHI restriction site, an N-terminal EE tag, and zvegf4 amino acid residues 258–381 (stop codon included). The 5' oligo primer contains the BamHI site, an N-terminal EE tag sequence, and zvegf4 basepairs corresponding to the N-terminus of the growth factor domain (ZC27,116; SEQ ID NO:47). The 3' oligo primer contains the last 21 basepairs of zvegf4 (stop codon included) (ZC27,137; SEQ ID NO:48). The expression vector pZMP20 was used, which contains the CMV immediate early promotor, a consensus intron from the variable region of mouse immunoglobulin heavy chain locus, Kozak sequences, an optimized t-PA secretory signal sequence (U.S. Pat. No. 5,641,655), multiple restriction sites for insertion of coding sequences, a stop codon, and a human growth hormone terminator. The plasmid also contains an IRES element from poliovirus, the extracellular domain of CD8 truncated at the C-terminal end of the transmembrane domain, an E. coli origin of replication, a DHFR gene, the SV40 terminator, and the URA3 and CEN-ARS sequences required for replication in S. cerevisiae. The resulting plasmid is designated pZMP20/GFD.NEE. A 504 basepair fragment with a 5° FseI site and 3' AscI site is isolated from this plasmid for ligation into the pEZE2 expression vector (5° FseI, 3' AscI) for expression in CHO DG44 cells.

Example 19
A. Mouse Genomic Library Screen

A partial mouse zvegf4 sequence was obtained by probing a mouse genomic library with a human zvegf4 restriction digest fragment containing the entire coding sequence. The probe was generated by digesting 8 mg of a full-length human zvegf4 plasmid with EcoR1 (Gibco BRL, Gaithersburg, Md.). The 1,289 bp fragment was gel purified on a 2.3% TBE gel and the cDNA was extracted from the agarose slab using the QIAquick Gel Extraction Kit (Qiagen). The mouse genomic library was an embl3 SP6/T7 lambda BamH1 cloned library (Clontech, Palo Alto, Calif.) plated on a K802 host lawn on 24 NZY plates, and represented $7.2 \times 10^5$ pfus.

Twenty four filter lifts were prehybridized in EXPRESSHYB solution (Clontech) containing 0.1 mg/ml salmon sperm DNA which had been boiled 5 minutes, then iced. Hybridization took place overnight at 50° C. Sixty three ng of the human fragment mentioned above were labeled with $^{32}$P using the Rediprime II Random Prime Labeling System (Amersham Pharmacia, Buckinghamshire, England). Unincorporated radioactivity was removed using a NucTrap push column (Stratagene, La Jolla, Calif.). Filters were hybridized in EXPRESSHYB solution containing 1.0× $10^6$ cpm/ml zvegf4 probe, 0.1 mg/ml salmon sperm DNA, and 0.5 µg/ml murine cot-1 DNA which had been boiled 5 minutes, then iced. Hybridization took place overnight at 50° C. Filter lifts were washed in 2×SSC, 0.1% SDS at room temperature for 2 hours, then the temperature was raised to 60° C. for one hour. Overnight exposure at −80° C. showed 7 putative primary hits.

A K802 host culture was prepared to plate the primary hits for a secondary screen. The 7 primary hits were picked with a Pasteur pipet and eluted in 1 ml SM (0.1 M NaCl, 50 mM Tris pH 7.5, 10 mM MgSO$_4$, 0.02% gelatin) with a few drops of chloroform overnight at 4° C. After plating to determine titers, 10 times the number of plaques in the original pfu were plated on NZY maxi plates with 10 mM MgSO$_4$/NZY top agarose and a lawn of K802 cells for four of the primary hits and grown overnight at 37° C. Lifts were done using Hybond-N filters (Amersham Pharmacia). The filters were marked for orientation with a hot needle, denatured in 1.5 M NaCl and 0.5 M NaOH for 10 minutes, then neutralized in 1.5 M NaCl and 0.5 M Tris-HCl pH 7.2 for 10 minutes. The DNA was affixed to the filter using a STRATALINKER UV crosslinker (Stratagene, La Jolla, Calif.) at 1200 joules, and prewashed at 65° C. in prewash buffer consisting of 0.25×SSC, 0.25% SDS and 1 mM EDTA, changing solution three times for a total of 45 minutes to remove cell debris. Five lifts were put in each vial, three vials total. Each vial of lifts was prehybridized overnight at 50° C. in 13 ml of EXPRESSHYB Hybridization Solution (Clontech) mixed with 1.3 mg salmon sperm DNA which had been boiled 5 minutes, then iced.

Sixty three ng of the human zvegf4 fragment was labeled for a probe as described above. Each vial of filters was hybridized in 9 ml of EXPRESSHYB Hybridization Solution mixed with 0.99 to $1.1 \times 10^6$ human zvegf4 probe, 0.5 µg/ml murine cot-1 DNA, and 0.9 mg/ml salmon sperm DNA which had been boiled 5 minutes, then iced. Hybridization took place overnight at 50° C. Wash conditions described above for the primary screen were repeated for this secondary screen. Two of the 4 primary putative hits that were tested came up positive after an overnight exposure at −80° C.

Isolated plaques #7c1 and #18b2 were eluted in 200 µgM overnight at 4° C., and fresh host K802 cells were prepared. Serial dilutions ranging from $10^{-2}$ to $10^{-3}$ were plated to obtain a titer estimate. Only #18b2 gave any plaques (for a titer of 2.6 to $3.0 \times 10^3$ phage per µl), and this plaque was further pursued. Two plates with $10^5$ pfus per plate were prepared for a phage DNA prep from plate lysates. Plates were grown at 37° C. for 6 hours, until the phage were starting to get confluent, and then 12 ml of SM per plate was added to elute the phage overnight at 4° C. At this point, plates were shaken at room temperature one hour, the supernatant was removed, 1% chloroform was added, and supernatant was shaken for 15 minutes. The DNA was prepped using the Wizard Lambda Preps DNA Purification System (Promega), sections IV and VI.

Plaque #18b2 DNA was cut with several restriction enzymes to generate fragments to run on a Southern gel. Digests were run on a 1% TBE agarose gel. The gel was soaked in 0.25 M HCl for 30 minutes, rinsed in distilled H$_2$O, soaked in 0.5 M NaOH and 1.5 M NaCl for 40 minutes with one solution change, and neutralized in 1.5 M NaCl and 0.5 M Tris-HCl (pH 7.2) for 40 minutes with one solution change. A TURBOBLOTTER Rapid Downward Transfer System (Schleicher & Schuell, Keene, N.H.) was set up to transfer the DNA onto a Nytran/BA-S membrane (Schleicher & Schuell) overnight. The DNA was affixed to the Nytran using a STRATALINKER UV crosslinker (Stratagene) at 1200 joules. The blot was prehybridized overnight at 50° C. in 12 ml EXPRESSHYB Hybridization Solution (Clontech) mixed with 1.2 mg salmon sperm DNA which had been boiled 5 minutes, then iced. Fifty nine ng of the human zvegf4 fragment was labeled for a probe, as described above. Unincorporated radioactivity was removed by chromatography using a commercially available push column (NUCTRAP column, Stratagene). Ten ml of EXPRESSHYB Hybridization Solution was mixed with $1.0 \times 10^6$ cpm/ml of human zvegf4 probe, 0.5 µg/ml murine cot-1 DNA, and 0.1 mg/ml salmon sperm DNA which had been boiled 5 minutes, then iced, and then added to the blot. Hybridization took place overnight at 50° C. The blot was washed as described above, and exposed to film overnight at −80° C.

The Southern gel had a fragment from the BamH1/Pst1 digest which hybridized to the probe in the size range of 2.0 to 2.9 kb, which was pursued. Plaque 18b2 lambda DNA (2.8 µg) was cut with 20 units of BamH1 (Boehringer Mannheim, Indianapolis, Ind.), and 20 µl Pst1 (Life Technologies) for 2 hours at 37° C. The digest was run on a 1% TBE gel, and a 2.0 kb doublet, as well as 2.7 kb/2.9 kb bands, were excised from the gel. The DNA was extracted from the agarose using the Qiaquick Gel Extraction Kit (Qiagen). The 18b2 fragments were ligated into a pbluescriptIIKS+ vector (Stratagene) cut with BamH1, Pst1 and BamH1/Pst1. Three clones with a Pst1 insert, and 4 clones with a BamH1/Pst1 insert, from these ligations were digested with their respective insert site restriction enzymes for another Southern blot to determine which was the original hybridizing fragment. The 1% TBE gel was treated and the DNA was transferred to the Nytran blot as described above. The blot was prehybridized as above in 13 ml of hybridization solution. Fifty nine ng of the human zvegf4 fragment was labeled and unincorporated radioactivity was removed as described above. Human zvegf4 probe ($8.4 \times 10^5$ /ml cpm), 0.1 mg/ml of salmon sperm DNA, and 0.5 µg/ml of mouse cot-1 DNA were boiled 5 minutes, iced 1 minute, and mixed with 7 ml of EXPRESSHYB hybridization solution, then added to the blot. Hybridization took place overnight at 50° C. The same washing procedure was used as mentioned above. The blot was exposed to film for 3 hours at −80° C., and both 2.0 kb band inserts strongly hybridized to the probe. These clones were sequenced and found to contain part of the murine zvegf4 cub domain. Primers were designed from this sequence for a PCR cDNA screen.

B. PCR Screen of Mouse cDNA Panel

A panel of available in house and commercial mouse cDNAs were screened with 20 pm each of ZG26,317 (SEQ ID NO:49) and ZG26,318 (SEQ ID NO:50) primers. The PCR reaction conditions were as follows: 94° C., 2 minutes; then 35 cycles of 94° C., 10 seconds; 65° C., 20 seconds; 72° C., 30 seconds; then ended with a 5 minute extension at 72° C. Embryo, salivary gland, neonatal skin and testis showed strong products of the predicted 200 bp size.

C. Full Length Mouse zvegf4 Sequence

The in house mouse testis arrayed library representing $9.6 \times 10^5$ clones was screened by PCR using primers ZG26, 317 (SEQ ID NO:49) and ZG26,318 (SEQ ID NO:50) according to conditions specified above. This library was deconvoluted down to a positive pool of 250 clones. *E. coli* DH10B cells (Gibco BRL) were transformed with this pool by electroporation following the manufacturer's protocol. The transformed culture was titered and arrayed out to 96 wells at ~20 cells/well. The cells were grown up in LB+amp overnight at 37° C. An aliquot of the cells was pelleted and PCR was used to identify a positive pool. Thermocycler conditions were as described above. The remaining cells from a positive pool were plated, and colonies were screened by PCR to identify a positive clone. Sequence analysis indicated that this clone, named "zvegf4mpzp7x-6", was incomplete at the 5' end and appeared to contain an intron at the 5' end.

The mouse salivary gland library representing $9.6 \times 10^5$ clones was then screened by PCR using primers ZG26,317 (SEQ ID NO:49) and ZG26,318 (SEQ ID NO:50) according to conditions specified above. The library was deconvoluted down to a positive pool of 250 clones. This 250 clonal pool was verified as having the 5' end by RACE. Twenty pm each of ZG26,318 (SEQ ID NO:50) and ZG14,063 (SEQ ID NO:51) primers and 3 :1 of that pool was used. The reaction was run as follows: 94° C., 2 minutes, then 5 cycles of 94° C., 15 seconds; 70° C., 30 seconds; 30 cycles of 94° C., 15 seconds, 62° C., 20 seconds; 7° C., 30 seconds, and a final extension at 72° C for 7 minutes. The RACE product obtained upon sequencing confirmed that this pool contained the initiation Met. The same protocol as described above was carried out to isolate a single clone from the pool. Sequence analysis revealed that this clone, named "zvegf4mpzp7x-7", had a 225 bp deletion in coding compared to clone #6 (bp 865 to bp 1079 in the final sequence).

The sequences derived from zvegf4mpzp7x-6 and from zvegf4mpzp7x-7 were combined to obtain a full-length mouse zvegf4 polynucleotide sequence (SEQ ID NO:52) and mouse zvegf4 polypeptide sequence (SEQ ID NO:53).

D. Full Length Mouse zvegf4 Clone

The full length cDNA clone was generated by a two step ligation of fragments from clone #6 and clone #7 from above. An EcoRl/Hind3 three prime fragment was generated from clone #6 first. Nine µg of clone #6 were digested with 15 units of EcoR1 (Gibco BRL, Gaithersburg, Md.) and 15 units of Hind3 (Gibco BRL) for 2 hours at 37° C. The 528 bp fragment was gel purified on a 1% TBE gel, and the cDNA was extracted from the gel slab using the QLAquick Gel Extraction Kit (Qiagen). It was ligated into pbluescriptIIKS+ (Stratagene) digested with $EcoR^1$ and Hind3. Three µg of a clone with this zvegf4 insert was digested with 15 units of EcoRl (Gibco BRL), gel purified on a 1% TBE gel, and the DNA was extracted using the kit mentioned above. The 5' EcoR1 zvegf4 fragment from clone #7 was ligated into the EcoR1-digested clone mentioned above. This EcoR1 fragment was generated by digesting 8 µg of clone #7 with 30 units of EcoR1 (Gibco BRL) for 2 hours at 37° C. The 754 bp fragment was gel purified on a 1% TBE gel, and the DNA was extracted from the gel slab as mentioned above.

Example 20

A. Treatment of Naïve PC12 Cells with zvegf4 Conditioned Medium

HaCat cells were infected with a null adenovirus (zPar) as a control, or with adenovirus expressing zvegf4. Conditioned medium (CM) from these transfected cells was assayed for its ability to induce neurite outgrowth in the PC12 Pheochromocytoma cell line (see Banker and Goslin, in *Culturing Nerve Cells*, chapter 6, "Culture and experimental use of the PC12 rat Pheochromocytoma cell line"; also, see Rydel and Greene, *J. Neuroscience* 7(11): 3639–53, November 1987).

Briefly, PC 12 cell cultures (ATCC# CRL 1721) were propagated with RPMI 1640 medium (Gibco/BRL, Gaithersburg, Md.), 10% horse serum (Sigma, St. Louis, Mo.), and 5% fetal bovine serum (FBS; Hyclone, Logan, Utah). Plastic culture dishes (Beckton Dickinson, Bedford, Mass.) were coated with rat tail collagen type I, and PC12 cells were plated into 24 well plates at $2 \times 10^4$ cells/ml in RPMI +1% FBS and incubated overnight at 37° C. in 5% $CO_2$. The PC12 culture medium was then removed, and replaced with either zvegf4-CM or control-CM added in 2-fold dilutions (starting at 5×dilution). Recombinant human NGF (R+D, Minneapolis, Minn.) was added as a positive control at concentrations of 100 or 30 ng/ml. As a negative control, CM of the null adenovirus (zpar) was used. To test for synergy of zvegf4 and NGF, additional wells of PC12 cells were treated with zvegf4-CM in combination with a suboptimal concentration of NGF (3 ng/ml). The culture medium was replaced every second day with RPMI+1% FBS, until the total length of incubation reached 7 days.

The NGF-treated PC12 cells exhibited stable neurite outgrowth and neuronal differentiation. PC12 cells exposed to zvegf4-CM exhibited morphological changes, such as cell flattening and the appearance of cells with short processes, suggesting differentiation into neuronal lineage. For PC12 cells incubated with a suboptimal dose of NGF plus zvegf4-CM, an increase in a population of cells bearing short processes was observed.

B. Treatment of Primed, Neurite-Bearing PC12 Cells with zvegf4 Conditioned Medium Zvegf4-CM and a control-CM (zpar) (as described in Example 20.A., above) were assayed for their ability to promote survival of differentiated PC12 neurons (see Banker and Goslin, supra, Rydel and Greene, supra).

Briefly, PC12 cells were maintained as described in Example 20.A., above, and were treated with appropriate doses of NGF to induce differentiation into cells that express the properties of post-mitotic sympathetic neurons. More specifically, PC12 cells were treated with recombinant human NGF (R+D, Minneapolis, Minn.) at a concentration of 50 ng/ml for 6 days, with a change of medium every other day. Cells were plated into 24 well plates overnight, and the culture medium was replaced with zvegf4-CM or control-CM (in 2-fold dilutions, starting at 5×), or with NGF as a positive control (starting with 100 ng/ml in 3-fold dilutions).

Cultures were set up either with 1% FBS or serum-free culture (SF) medium. Cells were propagated over 9 days, with medium changes on every second day. Continuous treatment with NGF alone promoted the survival of the entire neuronal population and produced increasing neurite outgrowth. Zvegf4-CM promoted the survival of a subpopulation of neurons, but did not induce additional neurite outgrowth. Cells cultured in control-CM degenerated.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated protein comprising a first polypeptide disulfide-bonded to a second polypeptide, wherein each of said first and second polypeptides is from 113 to 138 amino acid residues in length and comprises amino acid residues 258–370 of SEQ ID NO:2 and wherein said protein stimulates proliferation, differentiation, or migration of mesenchymal cells.

2. The isolated protein according to claim 1 wherein each of said first and second polypeptides comprises residues 250–370 of SEQ ID NO:2.

3. A pharmaceutical composition comprising a protein according to claim 1 in combination with a pharmaceutically acceptable vehicle.

4. The pharmaceutical composition according to claim 3 wherein each of said first and second polypeptides comprises residues 250–370 of SEQ ID NO:2.

5. The isolated protein according to claim 1 wherein each of said first and second polypeptides comprises residues 246–370 of SEQ ID NO:2.

6. The isolated protein according to claim 1 wherein each of said first and second polypeptides is from 113–118 amino acid residues in length.

7. An isolated protein produced by a method comprising:
   (a) culturing a host cell containing an expression vector comprising the following operably linked elements:
      a transcription promoter;
      a DNA segment encoding a polypeptide comprising a sequence of amino acid residues selected from the group consisting of:
         i) residues 52–370 of SEQ ID NO:2;
         ii) residues 52–253 of SEQ ID NO:2;
         iii) residues 180–370 of SEQ ID NO:2; and
         iv) residues 258–370 of SEQ ID NO:2; and
      a transcription terminator,
      under conditions whereby the DNA segment is expressed; and
   (b) recovering from the cell the protein product of expression of the DNA construct.

8. The isolated protein according to claim 7 wherein the host cell is a cultured mammalian cell.

9. The isolated protein according to claim 7 wherein the DNA segment further encodes a secretory peptide and wherein the protein is secreted from the host cell and recovered from a culture medium in which the host cell is cultured.

10. The isolated protein according to claim 7 wherein the host cell is a fungal cell.

11. The isolated protein according to claim 7 wherein the host cell is a cultured insect cell.

12. The isolated protein according to claim 7 wherein the polypeptide consists of residues 258–370 of SEQ ID NO:2, residues 250–370 of SEQ ID NO:2, or residues 246–370 of SEQ ID NO:2.

13. The isolated protein according to claim 7 wherein the polypeptide is from 113 to 138 amino acid residues in length and comprises amino acid residues 258–370 of SEQ ID NO:2.

14. A polypeptide comprising a sequence selected from the group consisting of:
   residues 1–302 of SEQ ID NO:54;
   residues 1–316 of SEQ ID NO:55;
   residues 1–317 of SEQ ID NO:56; and
   residues 1–303 of SEQ ID NO:57.

* * * * *

SEQUENCE LISTING

```
<160> NUMBER OF SEQ ID NOS: 57

<210> SEQ ID NO 1
<211> LENGTH: 1882
<212> TYPE: DNA
<213> ORGANISM: Homo sapiens
<220> FEATURE:
<221> NAME/KEY: CDS
<222> LOCATION: (226)...(1338)

<400> SEQUENCE: 1
ccgtcaccat ttatcagctc agcaccacaa ggaagtgcgg cacccacacg cgctcggaaa      60
gttcagcatg caggaagttt ggggagagct cggcgattag cacagcgacc cgggccagcg     120
cagggcgagc gcaggcggcg agagcgcagg gcggcgcggc gtcggtcccg ggagcagaac     180
ccggcttttt cttggagcga cgctgtctct agtcgctgat cccaa atg cac cgg ctc    237
                                                  Met His Arg Leu
                                                    1 atc ttt gtc tac act cta atc tgc gca aac ttt tgc agc tgt cgg gac       285
Ile Phe Val Tyr Thr Leu Ile Cys Ala Asn Phe Cys Ser Cys Arg Asp
  5                  10                  15                  20 act tct gca acc ccg cag agc gca tcc atc aaa gct ttg cgc aac gcc       333
Thr Ser Ala Thr Pro Gln Ser Ala Ser Ile Lys Ala Leu Arg Asn Ala
                 25                  30                  35 aac ctc agg cga gat gag agc aat cac ctc aca gac ttg tac cga aga       381
Asn Leu Arg Arg Asp Glu Ser Asn His Leu Thr Asp Leu Tyr Arg Arg
             40                  45                  50 gat gag acc atc cag gtg aaa gga aac ggc tac gtg cag agt cct aga       429
Asp Glu Thr Ile Gln Val Lys Gly Asn Gly Tyr Val Gln Ser Pro Arg
         55                  60                  65 ttc ccg aac agc tac ccc agg aac ctg ctc ctg aca tgg cgg ctt cac       477
Phe Pro Asn Ser Tyr Pro Arg Asn Leu Leu Leu Thr Trp Arg Leu His
     70                  75                  80 tct cag gag aat aca cgg ata cag cta gtg ttt gac aat cag ttt gga       525
Ser Gln Glu Asn Thr Arg Ile Gln Leu Val Phe Asp Asn Gln Phe Gly
 85                  90                  95                 100 tta gag gaa gca gaa aat gat atc tgt agg tat gat ttt gtg gaa gtt       573
Leu Glu Glu Ala Glu Asn Asp Ile Cys Arg Tyr Asp Phe Val Glu Val
                105                 110                 115 gaa gat ata tcc gaa acc agt acc att att aga gga cga tgg tgt gga       621
Glu Asp Ile Ser Glu Thr Ser Thr Ile Ile Arg Gly Arg Trp Cys Gly
            120                 125                 130 cac aag gaa gtt cct cca agg ata aaa tca aga acg aac caa att aaa       669
His Lys Glu Val Pro Pro Arg Ile Lys Ser Arg Thr Asn Gln Ile Lys
```

|     |     |     |     |     |     |     |     |     |     |     |     |     |     |     |     |      |
|---|---|---|---|---|---|---|---|---|---|---|---|---|---|---|---|---|
|     |     | 135 |     |     |     |     | 140 |     |     |     |     |     | 145 |     |     |      |
| atc | aca | ttc | aag | tcc | gat | gac | tac | ttt | gtg | gct | aaa | cct | gga | ttc | aag | 717  |
| Ile | Thr | Phe | Lys | Ser | Asp | Asp | Tyr | Phe | Val | Ala | Lys | Pro | Gly | Phe | Lys |      |
|     | 150 |     |     |     |     | 155 |     |     |     |     | 160 |     |     |     |     |      |
| att | tat | tat | tct | ttg | ctg | gaa | gat | ttc | caa | ccc | gca | gca | gct | tca | gag | 765  |
| Ile | Tyr | Tyr | Ser | Leu | Leu | Glu | Asp | Phe | Gln | Pro | Ala | Ala | Ala | Ser | Glu |      |
| 165 |     |     |     |     | 170 |     |     |     |     | 175 |     |     |     |     | 180 |      |
| acc | aac | tgg | gaa | tct | gtc | aca | agc | tct | att | tca | ggg | gta | tcc | tat | aac | 813  |
| Thr | Asn | Trp | Glu | Ser | Val | Thr | Ser | Ser | Ile | Ser | Gly | Val | Ser | Tyr | Asn |      |
|     |     |     |     | 185 |     |     |     |     | 190 |     |     |     |     | 195 |     |      |
| tct | cca | tca | gta | acg | gat | ccc | act | ctg | att | gcg | gat | gct | ctg | gac | aaa | 861  |
| Ser | Pro | Ser | Val | Thr | Asp | Pro | Thr | Leu | Ile | Ala | Asp | Ala | Leu | Asp | Lys |      |
|     |     |     | 200 |     |     |     |     | 205 |     |     |     |     | 210 |     |     |      |
| aaa | att | gca | gaa | ttt | gat | aca | gtg | gaa | gat | ctg | ctc | aag | tac | ttc | aat | 909  |
| Lys | Ile | Ala | Glu | Phe | Asp | Thr | Val | Glu | Asp | Leu | Leu | Lys | Tyr | Phe | Asn |      |
|     |     | 215 |     |     |     |     | 220 |     |     |     |     | 225 |     |     |     |      |
| cca | gag | tca | tgg | caa | gaa | gat | ctt | gag | aat | atg | tat | ctg | gac | acc | cct | 957  |
| Pro | Glu | Ser | Trp | Gln | Glu | Asp | Leu | Glu | Asn | Met | Tyr | Leu | Asp | Thr | Pro |      |
|     | 230 |     |     |     |     | 235 |     |     |     |     | 240 |     |     |     |     |      |
| cgg | tat | cga | ggc | agg | tca | tac | cat | gac | cgg | aag | tca | aaa | gtt | gac | ctg | 1005 |
| Arg | Tyr | Arg | Gly | Arg | Ser | Tyr | His | Asp | Arg | Lys | Ser | Lys | Val | Asp | Leu |      |
| 245 |     |     |     |     | 250 |     |     |     |     | 255 |     |     |     |     | 260 |      |
| gat | agg | ctc | aat | gat | gat | gcc | aag | cgt | tac | agt | tgc | act | ccc | agg | aat | 1053 |
| Asp | Arg | Leu | Asn | Asp | Asp | Ala | Lys | Arg | Tyr | Ser | Cys | Thr | Pro | Arg | Asn |      |
|     |     |     |     | 265 |     |     |     |     | 270 |     |     |     |     | 275 |     |      |
| tac | tcg | gtc | aat | ata | aga | gaa | gag | ctg | aag | ttg | gcc | aat | gtg | gtc | ttc | 1101 |
| Tyr | Ser | Val | Asn | Ile | Arg | Glu | Glu | Leu | Lys | Leu | Ala | Asn | Val | Val | Phe |      |
|     |     |     | 280 |     |     |     |     | 285 |     |     |     |     | 290 |     |     |      |
| ttt | cca | cgt | tgc | ctc | ctc | gtg | cag | cgc | tgt | gga | gga | aat | tgt | ggc | tgt | 1149 |
| Phe | Pro | Arg | Cys | Leu | Leu | Val | Gln | Arg | Cys | Gly | Gly | Asn | Cys | Gly | Cys |      |
|     |     | 295 |     |     |     |     | 300 |     |     |     |     | 305 |     |     |     |      |
| gga | act | gtc | aac | tgg | agg | tcc | tgc | aca | tgc | aat | tca | ggg | aaa | acc | gtg | 1197 |
| Gly | Thr | Val | Asn | Trp | Arg | Ser | Cys | Thr | Cys | Asn | Ser | Gly | Lys | Thr | Val |      |
|     | 310 |     |     |     |     | 315 |     |     |     |     | 320 |     |     |     |     |      |
| aaa | aag | tat | cat | gag | gta | tta | cag | ttt | gag | cct | ggc | cac | atc | aag | agg | 1245 |
| Lys | Lys | Tyr | His | Glu | Val | Leu | Gln | Phe | Glu | Pro | Gly | His | Ile | Lys | Arg |      |
| 325 |     |     |     |     | 330 |     |     |     |     | 335 |     |     |     |     | 340 |      |
| agg | ggt | aga | gct | aag | acc | atg | gct | cta | gtt | gac | atc | cag | ttg | gat | cac | 1293 |
| Arg | Gly | Arg | Ala | Lys | Thr | Met | Ala | Leu | Val | Asp | Ile | Gln | Leu | Asp | His |      |
|     |     |     |     | 345 |     |     |     |     | 350 |     |     |     |     | 355 |     |      |
| cat | gaa | cga | tgc | gat | tgt | atc | tgc | agc | tca | aga | cca | cct | cga | taa |     | 1338 |
| His | Glu | Arg | Cys | Asp | Cys | Ile | Cys | Ser | Ser | Arg | Pro | Pro | Arg | *   |     |      |
|     |     |     | 360 |     |     |     |     | 365 |     |     |     |     | 370 |     |     |      | gagaatgtgc acatccttac attaagcctg aaagaacctt tagtttaagg agggtgagat 1398 aagagaccct tttcctacca gcaaccaaac ttactactag cctgcaatgc aatgaacaca 1458 agtggttgct gagtctcagc cttgctttgt taatgccatg gcaagtagaa aggtatatca 1518 tcaacttcta tacctaagaa ataggattg catttaataa tagtgtttga ggttatatat 1578 gcacaaacac acacagaaat atattcatgt ctatgtgtat atagatcaaa tgttttttt 1638 ttttggtata tataaccagg tacaccagag gttacatatg tttgagttag actcttaaaa 1698 tcctttgcca aaataaggga tggtcaaata tatgaaacat gtctttagaa aatttaggag 1758 ataaatttat ttttaaattt tgaaacacga aacaattttg aatcttgctc tcttaaagaa 1818 agcatcttgt atattaaaaa tcaaaagatg aggctttctt acatatacat cttagttgat 1878 tatt 1882

```
<210> SEQ ID NO 2
<211> LENGTH: 370
<212> TYPE: PRT
<213> ORGANISM: Homo sapiens

<400> SEQUENCE: 2

Met His Arg Leu Ile Phe Val Tyr Thr Leu Ile Cys Ala Asn Phe Cys
 1               5                  10                  15

Ser Cys Arg Asp Thr Ser Ala Thr Pro Gln Ser Ala Ser Ile Lys Ala
             20                  25                  30

Leu Arg Asn Ala Asn Leu Arg Arg Asp Glu Ser Asn His Leu Thr Asp
         35                  40                  45

Leu Tyr Arg Arg Asp Glu Thr Ile Gln Val Lys Gly Asn Gly Tyr Val
     50                  55                  60

Gln Ser Pro Arg Phe Pro Asn Ser Tyr Pro Arg Asn Leu Leu Leu Thr
 65                  70                  75                  80

Trp Arg Leu His Ser Gln Glu Asn Thr Arg Ile Gln Leu Val Phe Asp
                 85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
        275                 280                 285

Asn Val Val Phe Phe Pro Arg Cys Leu Leu Val Gln Arg Cys Gly Gly
    290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
        355                 360                 365

Pro Arg
    370
```

```
<210> SEQ ID NO 3
<211> LENGTH: 126
<212> TYPE: PRT
<213> ORGANISM: Artificial Sequence
<220> FEATURE:
<223> OTHER INFORMATION: polypeptide motif
<221> NAME/KEY: VARIANT
<222> LOCATION: (2)...(19)
<223> OTHER INFORMATION: Xaa = Any Amino Acid
<221> NAME/KEY: VARIANT
<222> LOCATION: (20)...(34)
<223> OTHER INFORMATION: Xaa = Any Amino Acid or is not present
<221> NAME/KEY: VARIANT
<222> LOCATION: (36)...(45)
<223> OTHER INFORMATION: Xaa = Any Amino Acid
<221> NAME/KEY: VARIANT
<222> LOCATION: (46)...(72)
<223> OTHER INFORMATION: Xaa = Any Amino Acid or is not present
<221> NAME/KEY: VARIANT
<222> LOCATION: (74)...(93)
<223> OTHER INFORMATION: Xaa = Any Amino Acid
<221> NAME/KEY: VARIANT
<222> LOCATION: (94)...(123)
<223> OTHER INFORMATION: Xaa = Any Amino Acid or is not present
<221> NAME/KEY: VARIANT
<222> LOCATION: (125)...(125)
<223> OTHER INFORMATION: Xaa = Any Amino Acid

<400> SEQUENCE: 3

Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Cys Xaa Gly Xaa Cys Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Cys Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Cys Xaa Cys
            115                 120                 125

<210> SEQ ID NO 4
<211> LENGTH: 24
<212> TYPE: PRT
<213> ORGANISM: Artificial Sequence
<220> FEATURE:
<223> OTHER INFORMATION: polypeptide motif
<221> NAME/KEY: VARIANT
<222> LOCATION: (2)...(2)
<223> OTHER INFORMATION: Xaa = Lys or Arg
<221> NAME/KEY: VARIANT
<222> LOCATION: (4)...(4)
<223> OTHER INFORMATION: Xaa = Asp, Asn or Glu
<221> NAME/KEY: VARIANT
<222> LOCATION: (5)...(5)
<223> OTHER INFORMATION: Xaa = Trp, Tyr or Phe
<221> NAME/KEY: VARIANT
<222> LOCATION: (6)...(16)
<223> OTHER INFORMATION: Xaa = Any Amino Acid
<221> NAME/KEY: VARIANT
<222> LOCATION: (17)...(20)
<223> OTHER INFORMATION: Xaa = Any Amino Acid or is not present
<221> NAME/KEY: VARIANT
<222> LOCATION: (22)...(22)
```

```
<223> OTHER INFORMATION: Xaa = Lys or Arg
<221> NAME/KEY: VARIANT
<222> LOCATION: (23)...(23)
<223> OTHER INFORMATION: Xaa = Trp, Tyr or Phe

<400> SEQUENCE: 4

Cys Xaa Tyr Xaa Xaa Xaa Xaa Xaa Xaa Xaa Xaa Xaa Xaa Xaa Xaa
 1               5                  10                  15

Xaa Xaa Xaa Xaa Gly Xaa Xaa Cys
            20

<210> SEQ ID NO 5
<211> LENGTH: 6
<212> TYPE: PRT
<213> ORGANISM: Artificial Sequence
<220> FEATURE:
<223> OTHER INFORMATION: polypeptide tag

<400> SEQUENCE: 5

Glu Tyr Met Pro Met Glu
 1               5

<210> SEQ ID NO 6
<211> LENGTH: 1110
<212> TYPE: DNA
<213> ORGANISM: Artificial Sequence
<220> FEATURE:
<223> OTHER INFORMATION: degenerate sequence
<221> NAME/KEY: misc_feature
<222> LOCATION: (1)...(1110)
<223> OTHER INFORMATION: n = A,T,C or G

<400> SEQUENCE: 6
atgcaymgny tnathttygt ntayacnytn athtgygcna ayttytgyws ntgymgngay      60
acnwsngcna cnccncarws ngcnwsnath aargcnytnm gnaaygcnaa yytnmgnmgn     120
gaygarwsna aycayytnac ngayytntay mgnmgngayg aracnathca rgtnaarggn     180
aayggntayg tncarwsncc nmgnttyccn aaywsntayc cnmgnaayyt nytnytnacn     240
tggmgnytnc aywsncarga raayacnmgn athcarytng tnttygayaa ycarttyggn     300
ytngargarg cngaraayga yathtgymgn taygayttyg tngargtnga rgayathwsn     360
garacnwsna cnathathmg nggnmgntgg tgyggncaya argargtncc nccnmgnath     420
aarwsnmgna cnaaycarat haarathacn ttyaarwsng aygaytaytt ygtngcnaar     480
ccnggnttya arathtayta ywsnytnytn gargayttyc arccngcngc ngcnwsngar     540
acnaaytggg arwsngtnac nwsnwsnath wsnggngtnw sntayaayws nccnwsngtn     600
acngayccna cnytnathgc ngaygcnytn gayaaraara thgcngartt ygayacngtn     660
gargayytny tnaartaytt yaayccngar wsntggcarg argayytnga raayatgtay     720
ytngayacnc nmgntaymg nggnmgnwsn taycaygaym gnaarwsnaa rgtngayytn     780
gaymgnytna aygaygaygc naarmgntay wsntgyacnc nmgnaayta ywsngtnaay     840 athmgnarg arytnaaryt ngcnaaygtn gtnttyttyc nmgntgyyt nytngtncar     900 mgntgyggng gnaaytgygg ntgyggnacn gtnaaytggm gnwsntgyac ntgyaaywsn     960
ggnaaracng tnaaraarta ycaygargtn ytncarttyg arccnggnca yathaarmgn    1020
mgnggnmgng cnaaracnat ggcnytngtn gayathcary tngaycayca ygarmgntgy    1080
gaytgyatht gywsnwsnmg nccnccnmgn                                     1110

<210> SEQ ID NO 7
```

```
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 7
mgntgyggng gnaaytg                                                  17

<210> SEQ ID NO 8
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 8
mgntgydsng gnwrytg                                                  17

<210> SEQ ID NO 9
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 9
carywnccns hrcanck                                                  17

<210> SEQ ID NO 10
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 10
ttyttyccnm gntgyyt                                                  17

<210> SEQ ID NO 11
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 11
ntnddnccnn sntgybt                                                  17

<210> SEQ ID NO 12
<211> LENGTH: 17
<212> TYPE: DNA
<213> ORGANISM: Artificial Sequence
<220> FEATURE:
```

```
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 12
avrcansnng gnhhnan                                                17

<210> SEQ ID NO 13
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 13
caygarmgnt gygaytg                                                17

<210> SEQ ID NO 14
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 14
caynnnnvnt gyvvntg                                                17

<210> SEQ ID NO 15
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 15
canbbrcanb nnnnrtg                                                17

<210> SEQ ID NO 16
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 16
tgyacnccnm gnaayta                                                17

<210> SEQ ID NO 17
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G
```

```
<400> SEQUENCE: 17
tgyhnnmcnm knrmndh                                              17

<210> SEQ ID NO 18
<211> LENGTH: 17
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(17)
<223> OTHER INFORMATION: n = A,T,C or G

<400> SEQUENCE: 18
dhnkynmkng knndrca                                              17

<210> SEQ ID NO 19
<211> LENGTH: 18
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(18)
<223> OTHER INFORMATION: n = A,T,C or G

<400> SEQUENCE: 19
ntaygaytwy gtngargt                                             18

<210> SEQ ID NO 20
<211> LENGTH: 18
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(18)
<223> OTHER INFORMATION: n = A,T,C or G

<400> SEQUENCE: 20
natrctrawr canctyca                                             18

<210> SEQ ID NO 21
<211> LENGTH: 18
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(18)
<223> OTHER INFORMATION: n = A,T,C or G

<400> SEQUENCE: 21
gntdbccnma ndvntayc                                             18

<210> SEQ ID NO 22
<211> LENGTH: 18
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(18)
<223> OTHER INFORMATION: n = A,T,C or G

<400> SEQUENCE: 22
cnahvggnkt nhbnatrg                                             18
```

```
<210> SEQ ID NO 23
<211> LENGTH: 18
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(18)
<223> OTHER INFORMATION: n = A,T,C or G

<400> SEQUENCE: 23
tnhdnggnmr ntdbtgyg                                                 18

<210> SEQ ID NO 24
<211> LENGTH: 18
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(18)
<223> OTHER INFORMATION: n = A,T,C or G

<400> SEQUENCE: 24
andhnccnky nahvacrc                                                 18

<210> SEQ ID NO 25
<211> LENGTH: 24
<212> TYPE: DNA
<213> ORGANISM: Artificial Sequence
<220> FEATURE:
<223> OTHER INFORMATION: oligonucleotide primer ZC21,119

<400> SEQUENCE: 25
aggacgatgg tgtggacaca agga                                          24

<210> SEQ ID NO 26
<211> LENGTH: 24
<212> TYPE: DNA
<213> ORGANISM: Artificial Sequence
<220> FEATURE:
<223> OTHER INFORMATION: oligonucleotide primer ZC21,120

<400> SEQUENCE: 26
tccagagcat ccgcaatcag agtg                                          24

<210> SEQ ID NO 27
<211> LENGTH: 24
<212> TYPE: DNA
<213> ORGANISM: Artificial Sequence
<220> FEATURE:
<223> OTHER INFORMATION: oligonucleotide primer ZC21,987

<400> SEQUENCE: 27
caacctgttg tttgtcccgt cacc                                          24

<210> SEQ ID NO 28
<211> LENGTH: 25
<212> TYPE: DNA
<213> ORGANISM: Artificial Sequence
<220> FEATURE:
<223> OTHER INFORMATION: oligonucleotide primer ZC17,251

<400> SEQUENCE: 28
tctggacgtc ctcctgctgg tatag                                         25
```

<210> SEQ ID NO 29
<211> LENGTH: 25
<212> TYPE: DNA
<213> ORGANISM: Artificial Sequence
<220> FEATURE:
<223> OTHER INFORMATION: oligonucleotide primer ZC17,252

<400> SEQUENCE: 29
ggtatggagc aagggcaag ttggg                                          25

<210> SEQ ID NO 30
<211> LENGTH: 27
<212> TYPE: DNA
<213> ORGANISM: Artificial Sequence
<220> FEATURE:
<223> OTHER INFORMATION: oligonucleotide primer ZC17,156

<400> SEQUENCE: 30
gagtggcaac ttccagggcc aggagag                                       27

<210> SEQ ID NO 31
<211> LENGTH: 27
<212> TYPE: DNA
<213> ORGANISM: Artificial Sequence
<220> FEATURE:
<223> OTHER INFORMATION: oligonucleotide primer ZC17,157

<400> SEQUENCE: 31
cttttgctag cctcaaccct gactatc                                       27

<210> SEQ ID NO 32
<211> LENGTH: 1760
<212> TYPE: DNA
<213> ORGANISM: Homo sapiens
<220> FEATURE:
<221> NAME/KEY: CDS
<222> LOCATION: (154)...(1191)

<400> SEQUENCE: 32

```
attatgtgga aactaccctg cgattctctg ctgccagagc aggctcggcg cttccacccc      60
agtgcagcct tcccctggcg gtggtgaaag agactcggga gtcgctgctt ccaaagtgcc     120
cgccgtgagt gagctctcac cccagtcagc caa atg agc ctc ttc ggg ctt ctc     174
                                    Met Ser Leu Phe Gly Leu Leu
                                      1               5 ctg ctg aca tct gcc ctg gcc ggc cag aga cag ggg act cag gcg gaa       222
Leu Leu Thr Ser Ala Leu Ala Gly Gln Arg Gln Gly Thr Gln Ala Glu
         10                  15                  20 tcc aac ctg agt agt aaa ttc cag ttt tcc agc aac aag gaa cag aac       270
Ser Asn Leu Ser Ser Lys Phe Gln Phe Ser Ser Asn Lys Glu Gln Asn
     25                  30                  35 gga gta caa gat cct cag cat gag aga att att act gtg tct act aat       318
Gly Val Gln Asp Pro Gln His Glu Arg Ile Ile Thr Val Ser Thr Asn
 40                  45                  50                  55 gga agt att cac agc cca agg ttt cct cat act tat cca aga aat acg       366
Gly Ser Ile His Ser Pro Arg Phe Pro His Thr Tyr Pro Arg Asn Thr
                 60                  65                  70 gtc ttg gta tgg aga tta gta gca gta gag gaa aat gta tgg ata caa       414
Val Leu Val Trp Arg Leu Val Ala Val Glu Glu Asn Val Trp Ile Gln
             75                  80                  85 ctt acg ttt gat gaa aga ttt ggg ctt gaa gac cca gaa gat gac ata       462
Leu Thr Phe Asp Glu Arg Phe Gly Leu Glu Asp Pro Glu Asp Asp Ile
         90                  95                 100
```

-continued

| | | |
|---|---|---|
| tgc aag tat gat ttt gta gaa gtt gag gaa ccc agt gat gga act ata<br>Cys Lys Tyr Asp Phe Val Glu Val Glu Glu Pro Ser Asp Gly Thr Ile<br>105                        110                       115 | 510 |
| tta ggg cgc tgg tgt ggt tct ggt act gta cca gga aaa cag att tct<br>Leu Gly Arg Trp Cys Gly Ser Gly Thr Val Pro Gly Lys Gln Ile Ser<br>120                       125                   130                   135 | 558 |
| aaa gga aat caa att agg ata aga ttt gta tct gat gaa tat ttt cct<br>Lys Gly Asn Gln Ile Arg Ile Arg Phe Val Ser Asp Glu Tyr Phe Pro<br>                  140                     145                     150 | 606 |
| tct gaa cca ggg ttc tgc atc cac tac aac att gtc atg cca caa ttc<br>Ser Glu Pro Gly Phe Cys Ile His Tyr Asn Ile Val Met Pro Gln Phe<br>                155                     160                   165 | 654 |
| aca gaa gct gtg agt cct tca gtg cta ccc cct tca gct ttg cca ctg<br>Thr Glu Ala Val Ser Pro Ser Val Leu Pro Pro Ser Ala Leu Pro Leu<br>         170                     175                   180 | 702 |
| gac ctg ctt aat aat gct ata act gcc ttt agt acc ttg gaa gac ctt<br>Asp Leu Leu Asn Asn Ala Ile Thr Ala Phe Ser Thr Leu Glu Asp Leu<br>185                       190                   195 | 750 |
| att cga tat ctt gaa cca gag aga tgg cag ttg gac tta gaa gat cta<br>Ile Arg Tyr Leu Glu Pro Glu Arg Trp Gln Leu Asp Leu Glu Asp Leu<br>200                       205                   210                   215 | 798 |
| tat agg cca act tgg caa ctt ctt ggc aag gct ttt gtt ttt gga aga<br>Tyr Arg Pro Thr Trp Gln Leu Leu Gly Lys Ala Phe Val Phe Gly Arg<br>                  220                     225                   230 | 846 |
| aaa tcc aga gtg gtg gat ctg aac ctt cta aca gag gag gta aga tta<br>Lys Ser Arg Val Val Asp Leu Asn Leu Leu Thr Glu Glu Val Arg Leu<br>                  235                     240                   245 | 894 |
| tac agc tgc aca cct cgt aac ttc tca gtg tcc ata agg gaa gaa cta<br>Tyr Ser Cys Thr Pro Arg Asn Phe Ser Val Ser Ile Arg Glu Glu Leu<br>         250                     255                   260 | 942 |
| aag aga acc gat acc att ttc tgg cca ggt tgt ctc ctg gtt aaa cgc<br>Lys Arg Thr Asp Thr Ile Phe Trp Pro Gly Cys Leu Leu Val Lys Arg<br>265                       270                   275 | 990 |
| tgt ggt ggg aac tgt gcc tgt tgt ctc cac aat tgc aat gaa tgt caa<br>Cys Gly Gly Asn Cys Ala Cys Cys Leu His Asn Cys Asn Glu Cys Gln<br>280                       285                   290                   295 | 1038 |
| tgt gtc cca agc aaa gtt act aaa aaa tac cac gag gtc ctt cag ttg<br>Cys Val Pro Ser Lys Val Thr Lys Lys Tyr His Glu Val Leu Gln Leu<br>                  300                     305                   310 | 1086 |
| aga cca aag acc ggt gtc agg gga ttg cac aaa tca ctc acc gac gtg<br>Arg Pro Lys Thr Gly Val Arg Gly Leu His Lys Ser Leu Thr Asp Val<br>                  315                     320                   325 | 1134 |
| gcc ctg gag cac cat gag gag tgt gac tgt gtg tgc aga ggg agc aca<br>Ala Leu Glu His His Glu Glu Cys Asp Cys Val Cys Arg Gly Ser Thr<br>         330                     335                   340 | 1182 |
| gga gga tag ccgcatcacc accagcagct cttgcccaga gctgtgcagt<br>Gly Gly *<br>345 | 1231 |
| gcagtggctg attctattag agaacgtatg cgttatctcc atccttaatc tcagttgttt | 1291 |
| gcttcaagga cctttcatct tcaggattta cagtgcattc tgaaagagga gacatcaaac | 1351 |
| agaattagga gttgtgcaac agctcttttg agaggaggcc taaggacag gagaaaaggt | 1411 |
| cttcaatcgt ggaaagaaaa ttaaatgttg tattaaatag atcaccagct agtttcagag | 1471 |
| ttaccatgta cgtattccac tagctgggtt ctgtatttca gttctttcga tacggcttag | 1531 |
| ggtaatgtca gtacaggaaa aaaactgtgc aagtgagcac ctgattccgt tgccttgctt | 1591 |
| aactctaaag ctccatgtcc tgggcctaaa atcgtataaa atctggattt ttttttttt | 1651 |
| tttttgctca tattcacata tgtaaaccag aacattctat gtactacaaa cctggttttt | 1711 | aaaaaggaac tatgttgcta tgaattaaac ttgtgtcgtg ctgatagga          1760

<210> SEQ ID NO 33
<211> LENGTH: 345
<212> TYPE: PRT
<213> ORGANISM: Homo sapiens

<400> SEQUENCE: 33

Met Ser Leu Phe Gly Leu Leu Leu Thr Ser Ala Leu Ala Gly Gln
 1               5                  10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
            35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

<210> SEQ ID NO 34

-continued

```
<211> LENGTH: 3571
<212> TYPE: DNA
<213> ORGANISM: Mus musculus
<220> FEATURE:
<221> NAME/KEY: CDS
<222> LOCATION: (1049)...(2086)

<400> SEQUENCE: 34
```

| | |
|---|---|
| gaattcccgg gtcgacccac gcgtccgggc gcccagggga aaggaagctg ggggccgcct | 60 |
| ggcggcattc ctcgccgcag tgtgggctcc gtctgccgcg gggcccgcag tgcccctgt | 120 |
| ctgcgccagc acctgttggc ccgccagctg ccgcccgcg ccccccgcgc ccccccgcgcc | 180 |
| cgcccggccg ccagccccgc gccccgcgcg ccgcccgctg ggggaaagtg gagacgggga | 240 |
| ggggacaaga gcgatcctcc aggccagcca ggccttccct tagccgcccg tgcttagccg | 300 |
| ccacctctcc tcagccctgc gtcctgccct gccttagggc aggcatccga gcgctcgcga | 360 |
| ctccgagccg cccaagctct cccggcttcc cgcagcactt cgccggtacc cgagggaact | 420 |
| tcggtggcca ccgactgcag caaggaggag gctccgcggt ggatccgggc cagtcccgag | 480 |
| tcgtccccgc ggcctctctg cccgcccggg accgcgcgg cactcgcagg gcacggtccc | 540 |
| ctcccccag gtgggggtgg ggcgccgcct gccgccccga tcagcagctt tgtcattgat | 600 |
| cccaaggtgc tcgcctcgct gccgacctgg cttccagtct ggcttggcgg gaccccgagt | 660 |
| cctcgcctgt gtcctgtccc ccaaactgac aggtgctccc tgcgagtcgc cacgactcat | 720 |
| cgccgctccc ccgcgtcccc accccttctt tcctcccctcg cctaccccca ccccccgcac | 780 |
| ttcggcacag ctcaggatt gtttaaacct tgggaaactg gttcaggtcc aggttttgct | 840 |
| ttgatccttt tcaaaaactg gagacacaga agagggctct aggaaaaact tttggatggg | 900 |
| attatgtgga aactaccctg cgattctctg ctgccagagc cggccaggcg cttccaccgc | 960 |
| agcgcagcct ttccccggct gggctgagcc ttggagtcgt cgcttcccca gtgcccgccg | 1020 |

| | | |
|---|---|---|
| cgagtgagcc ctcgccccag tcagccaa atg ctc ctc ctc ggc ctc ctc ctg | | 1072 |
| Met Leu Leu Leu Gly Leu Leu Leu | | |
| 1 5 | | |
| ctg aca tct gcc ctg gcc ggc caa aga acg ggg act cgg gct gag tcc | | 1120 |
| Leu Thr Ser Ala Leu Ala Gly Gln Arg Thr Gly Thr Arg Ala Glu Ser | | |
| 10 15 20 | | |
| aac ctg agc agc aag ttg cag ctc tcc agc gac aag gaa cag aac gga | | 1168 |
| Asn Leu Ser Ser Lys Leu Gln Leu Ser Ser Asp Lys Glu Gln Asn Gly | | |
| 25 30 35 40 | | |
| gtg caa gat ccc cgg cat gag aga gtt gtc act ata tct ggt aat ggg | | 1216 |
| Val Gln Asp Pro Arg His Glu Arg Val Val Thr Ile Ser Gly Asn Gly | | |
| 45 50 55 | | |
| agc atc cac agc ccg aag ttt cct cat aca tac cca aga aat atg gtg | | 1264 |
| Ser Ile His Ser Pro Lys Phe Pro His Thr Tyr Pro Arg Asn Met Val | | |
| 60 65 70 | | |
| ctg gtg tgg aga tta gtt gca gta gat gaa aat gtg cgg atc cag ctg | | 1312 |
| Leu Val Trp Arg Leu Val Ala Val Asp Glu Asn Val Arg Ile Gln Leu | | |
| 75 80 85 | | |
| aca ttt gat gag aga ttt ggg ctg gaa gat cca gaa gac gat ata tgc | | 1360 |
| Thr Phe Asp Glu Arg Phe Gly Leu Glu Asp Pro Glu Asp Asp Ile Cys | | |
| 90 95 100 | | |
| aag tat gat ttt gta gaa gtt gag gag ccc agt gat gga agt gtt tta | | 1408 |
| Lys Tyr Asp Phe Val Glu Val Glu Glu Pro Ser Asp Gly Ser Val Leu | | |
| 105 110 115 120 | | |
| gga cgc tgg tgt ggt tct ggg act gtg cca gga aag cag act tct aaa | | 1456 |
| Gly Arg Trp Cys Gly Ser Gly Thr Val Pro Gly Lys Gln Thr Ser Lys | | |
| 125 130 135 | | |

-continued

| | |
|---|---|
| gga aat cat atc agg ata aga ttt gta tct gat gag tat ttt cca tct<br>Gly Asn His Ile Arg Ile Arg Phe Val Ser Asp Glu Tyr Phe Pro Ser<br>     140                           145                    150 | 1504 |
| gaa ccc gga ttc tgc atc cac tac agt att atc atg cca caa gtc aca<br>Glu Pro Gly Phe Cys Ile His Tyr Ser Ile Ile Met Pro Gln Val Thr<br>     155                           160                    165 | 1552 |
| gaa acc acg agt cct tcg gtg ttg ccc cct tca tct ttg tca ttg gac<br>Glu Thr Thr Ser Pro Ser Val Leu Pro Pro Ser Ser Leu Ser Leu Asp<br>170                          175                    180 | 1600 |
| ctg ctc aac aat gct gtg act gcc ttc agt acc ttg gaa gag ctg att<br>Leu Leu Asn Asn Ala Val Thr Ala Phe Ser Thr Leu Glu Glu Leu Ile<br>185                    190                    195                    200 | 1648 |
| cgg tac cta gag cca gat cga tgg cag gtg gac ttg gac agc ctc tac<br>Arg Tyr Leu Glu Pro Asp Arg Trp Gln Val Asp Leu Asp Ser Leu Tyr<br>                    205                    210                    215 | 1696 |
| aag cca aca tgg cag ctt ttg ggc aag gct ttc ctg tat ggg aaa aaa<br>Lys Pro Thr Trp Gln Leu Leu Gly Lys Ala Phe Leu Tyr Gly Lys Lys<br>     220                           225                    230 | 1744 |
| agc aaa gtg gtg aat ctg aat ctc ctc aag gaa gag gta aaa ctc tac<br>Ser Lys Val Val Asn Leu Asn Leu Leu Lys Glu Glu Val Lys Leu Tyr<br>                    235                    240                    245 | 1792 |
| agc tgc aca ccc cgg aac ttc tca gtg tcc ata cgg gaa gag cta aag<br>Ser Cys Thr Pro Arg Asn Phe Ser Val Ser Ile Arg Glu Glu Leu Lys<br>     250                           255                    260 | 1840 |
| agg aca gat acc ata ttc tgg cca ggt tgt ctc ctg gtc aag cgc tgt<br>Arg Thr Asp Thr Ile Phe Trp Pro Gly Cys Leu Leu Val Lys Arg Cys<br>265                          270                    275                    280 | 1888 |
| gga gga aat tgt gcc tgt tgt ctc cat aat tgc aat gaa tgt cag tgt<br>Gly Gly Asn Cys Ala Cys Cys Leu His Asn Cys Asn Glu Cys Gln Cys<br>                    285                    290                    295 | 1936 |
| gtc cca cgt aaa gtt aca aaa aag tac cat gag gtc ctt cag ttg aga<br>Val Pro Arg Lys Val Thr Lys Lys Tyr His Glu Val Leu Gln Leu Arg<br>     300                           305                    310 | 1984 |
| cca aaa act gga gtc aag gga ttg cat aag tca ctc act gat gtg gct<br>Pro Lys Thr Gly Val Lys Gly Leu His Lys Ser Leu Thr Asp Val Ala<br>                    315                    320                    325 | 2032 |
| ctg gaa cac cac gag gaa tgt gac tgt gtg tgt aga gga aac gca gga<br>Leu Glu His His Glu Glu Cys Asp Cys Val Cys Arg Gly Asn Ala Gly<br>330                          335                    340 | 2080 |
| ggg taa ctgcagcctt cgtagcagca cacgtgagca ctggcattct gtgtaccccc<br>Gly  *<br>345 | 2136 |
| acaagcaacc ttcatcccca ccagcgttgg ccgcagggct ctcagctgct gatgctggct | 2196 |
| atggtaaaga tcttactcgt ctccaaccaa attctcagtt gtttgcttca atagccttcc | 2256 |
| cctgcaggac ttcaagtgtc ttctaaaaga ccagaggcac caagaggagt caatcacaaa | 2316 |
| gcactgcctt ctagaggaag cccagacaat ggtcttctga ccacagaaac aaatgaaatg | 2376 |
| aatgtagatc gctagcaaac tctggagtga cagcatttct tttccactga cagaatggtg | 2436 |
| tagcttagtt gtcttgatat gggcaagtga tgtcagcaca agaaaatggt gaaaaacaca | 2496 |
| cacttgattg tgaacaatgc agaaatactt ggatttctcc aacctgtttg catagataga | 2556 |
| cagatgctct gttttctaca aactcaaagc ttttagagag cagctatgtt aataggaatt | 2616 |
| aaatgtgcca tgctgaaagg aaagactgaa gttttcaatg cttggcaact tctccgcaat | 2676 |
| ttggaggaaa ggtgcggtca tggtttggag aaagcacacc tgcacagagg agtggccttc | 2736 |
| ccttcccttc cctctgaggt ggcttctgtg tttcattgtg tatattttta tattctcctt | 2796 |
| ttgacattat aactgttggc ttttctaatc ttgttaaata tttctatttt taccaaaggt | 2856 |

-continued

```
atttaatatt cttttttatg acaacctaga gcaattattt ttagcttgat aattttttt      2916 tctaaacaaa attgttatag ccagaagaac aaagatgatt gatataaaaa tcttgttgct     2976
ctgacaaaaa catatgtatt tcttccttgt atggtgctag agcttagcgt catctgcatt     3036
tgaaaagatg gaatgggaa gttttagaa ttggtaggtc gcagggacag tttgataaca       3096
actgtactat catcaattcc caattctgtt cttagagcta cgaacagaac agagcttgag     3156
taaatatgga gccattgcta acctacccct ttctatggga aataggagta tagctcagag     3216
aagcacgtcc ccagaaacct cgaccatttc taggcacagt gttctgggct atgctgcgct    3276
gtatggacat atcctattta tttcaatact agggttttat tacctttaaa ctctgctcca    3336
tacacttgta ttaatacatg gatatttta tgtacagaag tatatcattt aaggagttca     3396
cttattatac tctttggcaa ttgcaaagaa atcaacata atacattgct tgtaaatgct     3456
taatctgtgc ccaagttttg tggtgactat ttgaattaaa atgtattgaa tcatcaaata    3516
aaataatctg gctattttgg ggaaaaaaa aaaaaaaaa aaaagggcg ccgc              3571
```

<210> SEQ ID NO 35
<211> LENGTH: 345
<212> TYPE: PRT
<213> ORGANISM: Mus musculus

<400> SEQUENCE: 35

```
Met Leu Leu Leu Gly Leu Leu Leu Thr Ser Ala Leu Ala Gly Gln
 1               5                  10                  15

Arg Thr Gly Thr Arg Ala Glu Ser Asn Leu Ser Ser Lys Leu Gln Leu
                20                  25                  30

Ser Ser Asp Lys Glu Gln Asn Gly Val Gln Asp Pro Arg His Glu Arg
            35                  40                  45

Val Val Thr Ile Ser Gly Asn Gly Ser Ile His Ser Pro Lys Phe Pro
        50                  55                  60

His Thr Tyr Pro Arg Asn Met Val Leu Val Trp Arg Leu Val Ala Val
65                  70                  75                  80

Asp Glu Asn Val Arg Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Ser Val Leu Gly Arg Trp Cys Gly Ser Gly Thr
        115                 120                 125

Val Pro Gly Lys Gln Thr Ser Lys Gly Asn His Ile Arg Ile Arg Phe
    130                 135                 140

Val Ser Asp Glu Tyr Phe Pro Ser Glu Pro Gly Phe Cys Ile His Tyr
145                 150                 155                 160

Ser Ile Ile Met Pro Gln Val Thr Glu Thr Thr Ser Pro Ser Val Leu
                165                 170                 175

Pro Pro Ser Ser Leu Ser Leu Asp Leu Leu Asn Asn Ala Val Thr Ala
            180                 185                 190

Phe Ser Thr Leu Glu Glu Leu Ile Arg Tyr Leu Glu Pro Asp Arg Trp
        195                 200                 205

Gln Val Asp Leu Asp Ser Leu Tyr Lys Pro Thr Trp Gln Leu Leu Gly
    210                 215                 220

Lys Ala Phe Leu Tyr Gly Lys Lys Ser Lys Val Val Asn Leu Asn Leu
225                 230                 235                 240

Leu Lys Glu Glu Val Lys Leu Tyr Ser Cys Thr Pro Arg Asn Phe Ser
```

```
                245                 250                 255
Val Ser Ile Arg Glu Glu Leu Lys Arg Thr Asp Thr Ile Phe Trp Pro
            260                 265                 270
Gly Cys Leu Leu Val Lys Arg Cys Gly Gly Asn Cys Ala Cys Cys Leu
        275                 280                 285
His Asn Cys Asn Glu Cys Gln Cys Val Pro Arg Lys Val Thr Lys Lys
    290                 295                 300
Tyr His Glu Val Leu Gln Leu Arg Pro Lys Thr Gly Val Lys Gly Leu
305                 310                 315                 320
His Lys Ser Leu Thr Asp Val Ala Leu Glu His Glu Glu Cys Asp
                325                 330                 335
Cys Val Cys Arg Gly Asn Ala Gly Gly
            340                 345

<210> SEQ ID NO 36
<211> LENGTH: 600
<212> TYPE: DNA
<213> ORGANISM: Homo sapiens
<220> FEATURE:
<221> NAME/KEY: CDS
<222> LOCATION: (496)...(594)

<400> SEQUENCE: 36
gtgggaagag tcccggccgg cgattaaact gggcatgctc agtggcagag caggtttagg      60
cccggcctgg gaaactgggg agctgaggtg ctcgcgccgc cgtctgagc ccgagtgcgc      120 gcctctcagg ggccgcggcc ggggctggag aacgctgctg ctccgctcgc ctgccccgct     180
agattcggcg ctgcccgccc cctgcagcct gtgctgcagc tgccggccac cggaggggc      240 gaacaaacaa acgtcaacct gttgtttgtc ccgtcaccat ttatcagctc agcaccacaa     300
ggaagtgcgg cacccacacg cgctcggaaa gttcagcatg caggaagttt ggggagagct     360
cggcgattag cacagcgacc cgggccagcg cagggcgagc gcagacggcg agagcgcagg     420
gcggcgcggc gtcggtcccg ggagcagaac ccggcttttt cttggagcga cgctgtctct     480
agtcgctgat cccaa atg cac cgg ctc atc ttt gtc tac act cta atc tgc      531
             Met His Arg Leu Ile Phe Val Tyr Thr Leu Ile Cys
                  1               5                  10
gca aac ttt tgc agc tgt cgg gac act tct gca acc ccg cag agc gca      579
Ala Asn Phe Cys Ser Cys Arg Asp Thr Ser Ala Thr Pro Gln Ser Ala
         15                  20                  25
tcc atc aaa gct tga gtattc                                            600
Ser Ile Lys Ala *
         30

<210> SEQ ID NO 37
<211> LENGTH: 18
<212> TYPE: DNA
<213> ORGANISM: Artificial Sequence
<220> FEATURE:
<223> OTHER INFORMATION: oligonucleotide primer ZC22,685

<400> SEQUENCE: 37
gccgtcacca tttatcag                                                    18

<210> SEQ ID NO 38
<211> LENGTH: 18
<212> TYPE: DNA
<213> ORGANISM: Artificial Sequence
<220> FEATURE:
<223> OTHER INFORMATION: oligonucleotide primer ZC22,686
```

<400> SEQUENCE: 38
cgggtcgctg tgctaatc                                                    18

<210> SEQ ID NO 39
<211> LENGTH: 18
<212> TYPE: PRT
<213> ORGANISM: Artificial Sequence
<220> FEATURE:
<223> OTHER INFORMATION: peptide

<400> SEQUENCE: 39

Cys Gly His Lys Glu Val Pro Pro Arg Ile Lys Ser Arg Thr Asn Gln
 1               5                  10                  15

Ile Lys

<210> SEQ ID NO 40
<211> LENGTH: 25
<212> TYPE: PRT
<213> ORGANISM: Artificial Sequence
<220> FEATURE:
<223> OTHER INFORMATION: peptide

<400> SEQUENCE: 40

Glu Ser Trp Gln Glu Asp Leu Glu Asn Met Tyr Leu Asp Thr Pro Arg
 1               5                  10                  15

Tyr Arg Gly Arg Ser Tyr His Asp Cys
            20                  25

<210> SEQ ID NO 41
<211> LENGTH: 24
<212> TYPE: PRT
<213> ORGANISM: Artificial Sequence
<220> FEATURE:
<223> OTHER INFORMATION: peptide

<400> SEQUENCE: 41

Cys Phe Glu Pro Gly His Ile Lys Arg Arg Gly Arg Ala Lys Thr Met
 1               5                  10                  15

Ala Leu Val Asp Ile Gln Leu Asp
            20

<210> SEQ ID NO 42
<211> LENGTH: 6
<212> TYPE: PRT
<213> ORGANISM: Artificial Sequence
<220> FEATURE:
<223> OTHER INFORMATION: peptide

<400> SEQUENCE: 42

Glu Tyr Met Pro Thr Asp
 1               5

<210> SEQ ID NO 43
<211> LENGTH: 42
<212> TYPE: DNA
<213> ORGANISM: Artificial Sequence
<220> FEATURE:
<223> OTHER INFORMATION: oligonucleotide primer ZC26136

<400> SEQUENCE: 43
taatataggc cggccgccat catgcaccgg ctcatctttg tc                          42

<210> SEQ ID NO 44
<211> LENGTH: 36

```
-continued

<212> TYPE: DNA
<213> ORGANISM: Artificial Sequence
<220> FEATURE:
<223> OTHER INFORMATION: oligonucleotide primer ZC26137

<400> SEQUENCE: 44
attatatggc gcgccttatc gaggtggtct tgagct                             36

<210> SEQ ID NO 45
<211> LENGTH: 24
<212> TYPE: DNA
<213> ORGANISM: Artificial Sequence
<220> FEATURE:
<223> OTHER INFORMATION: oligonucleotide primer ZC22341

<400> SEQUENCE: 45
cttggagcga cgctgtctct agtc                                          24

<210> SEQ ID NO 46
<211> LENGTH: 23
<212> TYPE: DNA
<213> ORGANISM: Artificial Sequence
<220> FEATURE:
<223> OTHER INFORMATION: oligonucleotide primer ZC22342

<400> SEQUENCE: 46
ccacttgtgt tcattgcatt gca                                           23

<210> SEQ ID NO 47
<211> LENGTH: 60
<212> TYPE: DNA
<213> ORGANISM: Artificial Sequence
<220> FEATURE:
<223> OTHER INFORMATION: oligonucleotide primer ZC27116

<400> SEQUENCE: 47
attataggat ccgagtatat gcctatggag gttgacctgg ataggctcaa tgatgatgcc   60

<210> SEQ ID NO 48
<211> LENGTH: 36
<212> TYPE: DNA
<213> ORGANISM: Artificial Sequence
<220> FEATURE:
<223> OTHER INFORMATION: oligonucleotide primer ZC26137

<400> SEQUENCE: 48
attatatggc gcgccttatc gaggtggtct tgagct                             36

<210> SEQ ID NO 49
<211> LENGTH: 25
<212> TYPE: DNA
<213> ORGANISM: Artificial Sequence
<220> FEATURE:
<223> OTHER INFORMATION: oligonucleotide primer ZC26317

<400> SEQUENCE: 49
atcacctcac agacttgtac cagag                                         25

<210> SEQ ID NO 50
<211> LENGTH: 25
<212> TYPE: DNA
<213> ORGANISM: Artificial Sequence
<220> FEATURE:
<223> OTHER INFORMATION: oligonucleotide primer ZC26318

<400> SEQUENCE: 50
```

-continued

```
cctacaaatg tcattttctg cttcc                                      25

<210> SEQ ID NO 51
<211> LENGTH: 25
<212> TYPE: DNA
<213> ORGANISM: Artificial Sequence
<220> FEATURE:
<223> OTHER INFORMATION: oligonucleotide primer ZC14063

<400> SEQUENCE: 51
caccagacat aatagctgac agact                                      25

<210> SEQ ID NO 52
<211> LENGTH: 1472
<212> TYPE: DNA
<213> ORGANISM: Mus musculus
<220> FEATURE:
<221> NAME/KEY: CDS
<222> LOCATION: (93)...(1205)

<400> SEQUENCE: 52
agggactgtg cagtagaaat ccgccgactc aacccttttgg gctttattta tttacttttg    60
gagcaacgcg atccctaggt cgctgagccc aa atg caa cgg ctc gtt tta gtc     113
                                    Met Gln Arg Leu Val Leu Val
                                     1               5 tcc att ctc ctg tgc gcg aac ttt agc tgc tat ccg gac act ttt gcg     161
Ser Ile Leu Leu Cys Ala Asn Phe Ser Cys Tyr Pro Asp Thr Phe Ala
         10                  15                  20 act ccg cag aga gca tcc atc aaa gct ttg cgc aat gcc aac ctc agg     209
Thr Pro Gln Arg Ala Ser Ile Lys Ala Leu Arg Asn Ala Asn Leu Arg
 25                  30                  35 aga gat gag agc aat cac ctc aca gac ttg tac cag aga gag gag aac     257
Arg Asp Glu Ser Asn His Leu Thr Asp Leu Tyr Gln Arg Glu Glu Asn
 40                  45                  50                  55 att cag gtg aca agc aat ggc cat gtg cag agt cct cgc ttc ccg aac     305
Ile Gln Val Thr Ser Asn Gly His Val Gln Ser Pro Arg Phe Pro Asn
             60                  65                  70 agc tac cca agg aac ctg ctt ctg aca tgg tgg ctc cgt tcc cag gag     353
Ser Tyr Pro Arg Asn Leu Leu Leu Thr Trp Trp Leu Arg Ser Gln Glu
         75                  80                  85 aaa aca cgg ata caa ctg tcc ttt gac cat caa ttc gga cta gag gaa     401
Lys Thr Arg Ile Gln Leu Ser Phe Asp His Gln Phe Gly Leu Glu Glu
 90                  95                 100 gca gaa aat gac att tgt agg tat gac ttt gtg gaa gtt gaa gaa gtc     449
Ala Glu Asn Asp Ile Cys Arg Tyr Asp Phe Val Glu Val Glu Glu Val
105                 110                 115 tca gag agc agc act gtt gtc aga gga aga tgg tgt ggc cac aag gag     497
Ser Glu Ser Ser Thr Val Val Arg Gly Arg Trp Cys Gly His Lys Glu
120                 125                 130                 135 atc cct cca agg ata acg tca aga aca aac cag att aaa atc aca ttt     545
Ile Pro Pro Arg Ile Thr Ser Arg Thr Asn Gln Ile Lys Ile Thr Phe
                140                 145                 150 aag tct gat gac tac ttt gtg gca aaa cct gga ttc aag att tat tat     593
Lys Ser Asp Asp Tyr Phe Val Ala Lys Pro Gly Phe Lys Ile Tyr Tyr
            155                 160                 165 tca ttt gtg gaa gat ttc caa ccg gaa gca gcc tca gag acc aac tgg     641
Ser Phe Val Glu Asp Phe Gln Pro Glu Ala Ala Ser Glu Thr Asn Trp
        170                 175                 180 gaa tca gtc aca agc tct ttc tct ggg gtg tcc tat cac tct cca tca     689
Glu Ser Val Thr Ser Ser Phe Ser Gly Val Ser Tyr His Ser Pro Ser
    185                 190                 195
```

```
ata acg gac ccc act ctc act gct gat gcc ctg gac aaa act gtc gca      737
Ile Thr Asp Pro Thr Leu Thr Ala Asp Ala Leu Asp Lys Thr Val Ala
200                 205                 210                 215 gaa ttc gat acc gtg gaa gat cta ctt aag cac ttc aat cca gtg tct      785
Glu Phe Asp Thr Val Glu Asp Leu Leu Lys His Phe Asn Pro Val Ser
                220                 225                 230 tgg caa gat gat ctg gag aat ttg tat ctg gac acc cct cat tat aga      833
Trp Gln Asp Asp Leu Glu Asn Leu Tyr Leu Asp Thr Pro His Tyr Arg
            235                 240                 245 ggc agg tca tac cat gat cgg aag tcc aaa gtg gac ctg gac agg ctc      881
Gly Arg Ser Tyr His Asp Arg Lys Ser Lys Val Asp Leu Asp Arg Leu
        250                 255                 260 aat gat gat gtc aag cgt tac agt tgc act ccc agg aat cac tct gtg      929
Asn Asp Asp Val Lys Arg Tyr Ser Cys Thr Pro Arg Asn His Ser Val
265                 270                 275 aac ctc agg gag gag ctg aag ctg acc aat gca gtc ttc ttc cca cga      977
Asn Leu Arg Glu Glu Leu Lys Leu Thr Asn Ala Val Phe Phe Pro Arg
280                 285                 290                 295 tgc ctc ctc gtg cag cgc tgt ggt ggc aac tgt ggt tgc gga act gtc     1025
Cys Leu Leu Val Gln Arg Cys Gly Gly Asn Cys Gly Cys Gly Thr Val
                300                 305                 310 aac tgg aag tcc tgc aca tgc agc tca ggg aag aca gtg aag aag tat     1073
Asn Trp Lys Ser Cys Thr Cys Ser Ser Gly Lys Thr Val Lys Lys Tyr
            315                 320                 325 cat gag gta ttg aag ttt gag cct gga cat ttc aag aga agg ggc aaa     1121
His Glu Val Leu Lys Phe Glu Pro Gly His Phe Lys Arg Arg Gly Lys
        330                 335                 340 gct aag aat atg gct ctt gtt gat atc cag ctg gat cat cat gag cga     1169
Ala Lys Asn Met Ala Leu Val Asp Ile Gln Leu Asp His His Glu Arg
345                 350                 355 tgt gac tgt atc tgc agc tca aga cca cct cga taa aacactatgc          1215
Cys Asp Cys Ile Cys Ser Ser Arg Pro Pro Arg *
360                 365                 370 acatctgtac tttgattatg aaaggacctt taggttacaa aaaccctaag aagcttctaa   1275
tctcagtgca atgaatgcat atggaaatgt tgctttgtta gtgccatggc aagaagaagc   1335
aaatatcatt aatttctata tacataaaca taggaattca cttatcaata gtatgtgaag   1395
atatgtatat atacttatat acatgactag ctctatgtat gtaaatagat taaatacttt   1455
attcagtata tttactg                                                  1472

<210> SEQ ID NO 53
<211> LENGTH: 370
<212> TYPE: PRT
<213> ORGANISM: Mus musculus

<400> SEQUENCE: 53

Met Gln Arg Leu Val Leu Val Ser Ile Leu Leu Cys Ala Asn Phe Ser
1               5                   10                  15

Cys Tyr Pro Asp Thr Phe Ala Thr Pro Gln Arg Ala Ser Ile Lys Ala
                20                  25                  30

Leu Arg Asn Ala Asn Leu Arg Arg Asp Glu Ser Asn His Leu Thr Asp
            35                  40                  45

Leu Tyr Gln Arg Glu Glu Asn Ile Gln Val Thr Ser Asn Gly His Val
        50                  55                  60

Gln Ser Pro Arg Phe Pro Asn Ser Tyr Pro Arg Asn Leu Leu Leu Thr
65                  70                  75                  80

Trp Trp Leu Arg Ser Gln Glu Lys Thr Arg Ile Gln Leu Ser Phe Asp
                85                  90                  95
```

-continued

His Gln Phe Gly Leu Glu Glu Ala Glu Asn Asp Ile Cys Arg Tyr Asp
            100                 105                 110

Phe Val Glu Val Glu Glu Val Ser Glu Ser Thr Val Val Arg Gly
            115                 120                 125

Arg Trp Cys Gly His Lys Glu Ile Pro Pro Arg Ile Thr Ser Arg Thr
            130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Phe Val Glu Asp Phe Gln Pro Glu
                165                 170                 175

Ala Ala Ser Glu Thr Asn Trp Glu Ser Val Thr Ser Ser Phe Ser Gly
            180                 185                 190

Val Ser Tyr His Ser Pro Ser Ile Thr Asp Pro Thr Leu Thr Ala Asp
            195                 200                 205

Ala Leu Asp Lys Thr Val Ala Glu Phe Asp Thr Val Glu Asp Leu Leu
            210                 215                 220

Lys His Phe Asn Pro Val Ser Trp Gln Asp Asp Leu Glu Asn Leu Tyr
225                 230                 235                 240

Leu Asp Thr Pro His Tyr Arg Gly Arg Ser Tyr His Asp Arg Lys Ser
                245                 250                 255

Lys Val Asp Leu Asp Arg Leu Asn Asp Asp Val Lys Arg Tyr Ser Cys
            260                 265                 270

Thr Pro Arg Asn His Ser Val Asn Leu Arg Glu Glu Leu Lys Leu Thr
            275                 280                 285

Asn Ala Val Phe Phe Pro Arg Cys Leu Leu Val Gln Arg Cys Gly Gly
            290                 295                 300

Asn Cys Gly Cys Gly Thr Val Asn Trp Lys Ser Cys Thr Cys Ser Ser
305                 310                 315                 320

Gly Lys Thr Val Lys Lys Tyr His Glu Val Leu Lys Phe Glu Pro Gly
                325                 330                 335

His Phe Lys Arg Arg Gly Lys Ala Lys Asn Met Ala Leu Val Asp Ile
            340                 345                 350

Gln Leu Asp His His Glu Arg Cys Asp Cys Ile Cys Ser Ser Arg Pro
            355                 360                 365

Pro Arg
    370

<210> SEQ ID NO 54
<211> LENGTH: 302
<212> TYPE: PRT
<213> ORGANISM: Artificial Sequence
<220> FEATURE:
<223> OTHER INFORMATION: fusion polypeptide

<400> SEQUENCE: 54

His Glu Arg Ile Ile Thr Val Ser Thr Asn Gly Ser Ile His Ser Pro
1               5                   10                  15

Arg Phe Pro His Thr Tyr Pro Arg Asn Thr Val Leu Val Trp Arg Leu
                20                  25                  30

Val Ala Val Glu Glu Asn Val Trp Ile Gln Leu Thr Phe Asp Glu Arg
            35                  40                  45

Phe Gly Leu Glu Asp Pro Glu Asp Ile Cys Lys Tyr Asp Phe Val
        50                  55                  60

Glu Val Glu Glu Pro Ser Asp Gly Thr Ile Leu Gly Arg Trp Cys Gly
65                  70                  75                  80

```
Ser Gly Thr Val Pro Gly Lys Gln Ile Ser Lys Gly Asn Gln Ile Arg
                85                  90                  95

Ile Arg Phe Val Ser Asp Glu Tyr Phe Pro Ser Glu Pro Gly Phe Cys
            100                 105                 110

Ile His Tyr Asn Ile Val Met Pro Gln Phe Thr Glu Ala Val Ser Pro
            115                 120                 125

Ser Val Leu Pro Pro Ser Ala Leu Pro Leu Asp Leu Leu Asn Asn Ala
        130                 135                 140

Ile Thr Ala Phe Ser Thr Leu Glu Asp Leu Ile Arg Tyr Leu Glu Pro
145                 150                 155                 160

Glu Arg Trp Gln Leu Asp Leu Glu Asp Leu Tyr Arg Pro Thr Trp Gln
                165                 170                 175

Leu Leu Gly Lys Ala Phe Val Phe Gly Arg Lys Ser Arg Val Asp Leu
            180                 185                 190

Asp Arg Leu Asn Asp Asp Ala Lys Arg Tyr Ser Cys Thr Pro Arg Asn
            195                 200                 205

Tyr Ser Val Asn Ile Arg Glu Glu Leu Lys Leu Ala Asn Val Val Phe
        210                 215                 220

Phe Pro Arg Cys Leu Leu Val Gln Arg Cys Gly Gly Asn Cys Gly Cys
225                 230                 235                 240

Gly Thr Val Asn Trp Arg Ser Cys Thr Cys Asn Ser Gly Lys Thr Val
                245                 250                 255

Lys Lys Tyr His Glu Val Leu Gln Phe Glu Pro Gly His Ile Lys Arg
            260                 265                 270

Arg Gly Arg Ala Lys Thr Met Ala Leu Val Asp Ile Gln Leu Asp His
            275                 280                 285

His Glu Arg Cys Asp Cys Ile Cys Ser Ser Arg Pro Pro Arg
        290                 295                 300

<210> SEQ ID NO 55
<211> LENGTH: 316
<212> TYPE: PRT
<213> ORGANISM: Artificial Sequence
<220> FEATURE:
<223> OTHER INFORMATION: fusion polypeptide

<400> SEQUENCE: 55

His Glu Arg Ile Ile Thr Val Ser Thr Asn Gly Ser Ile His Ser Pro
  1               5                  10                  15

Arg Phe Pro His Thr Tyr Pro Arg Asn Thr Val Leu Val Trp Arg Leu
                20                  25                  30

Val Ala Val Glu Glu Asn Val Trp Ile Gln Leu Thr Phe Asp Glu Arg
            35                  40                  45

Phe Gly Leu Glu Asp Pro Glu Asp Asp Ile Cys Lys Tyr Asp Phe Val
        50                  55                  60

Glu Val Glu Glu Pro Ser Asp Gly Thr Ile Leu Gly Arg Trp Cys Gly
65                  70                  75                  80

Ser Gly Thr Val Pro Gly Lys Gln Ile Ser Lys Gly Asn Gln Ile Arg
                85                  90                  95

Ile Arg Phe Val Ser Asp Glu Tyr Phe Pro Ser Glu Pro Gly Phe Cys
            100                 105                 110

Ile His Tyr Asn Ile Val Met Pro Gln Phe Thr Glu Ala Glu Thr Asn
            115                 120                 125

Trp Glu Ser Val Thr Ser Ser Ile Ser Gly Val Ser Tyr Asn Ser Pro
        130                 135                 140
```

```
Ser Val Thr Asp Pro Thr Leu Ile Ala Asp Ala Leu Asp Lys Lys Ile
145                 150                 155                 160

Ala Glu Phe Asp Thr Val Glu Asp Leu Leu Lys Tyr Phe Asn Pro Glu
                165                 170                 175

Ser Trp Gln Glu Asp Leu Glu Asn Met Tyr Leu Asp Thr Pro Arg Tyr
            180                 185                 190

Arg Gly Arg Ser Tyr His Asp Arg Lys Ser Lys Val Asp Leu Asp Arg
        195                 200                 205

Leu Asn Asp Asp Ala Lys Arg Tyr Ser Cys Thr Pro Arg Asn Tyr Ser
    210                 215                 220

Val Asn Ile Arg Glu Glu Leu Lys Leu Ala Asn Val Val Phe Phe Pro
225                 230                 235                 240

Arg Cys Leu Leu Val Gln Arg Cys Gly Gly Asn Cys Gly Cys Gly Thr
                245                 250                 255

Val Asn Trp Arg Ser Cys Thr Cys Asn Ser Gly Lys Thr Val Lys Lys
            260                 265                 270

Tyr His Glu Val Leu Gln Phe Glu Pro Gly His Ile Lys Arg Arg Gly
        275                 280                 285

Arg Ala Lys Thr Met Ala Leu Val Asp Ile Gln Leu Asp His His Glu
    290                 295                 300

Arg Cys Asp Cys Ile Cys Ser Ser Arg Pro Pro Arg
305                 310                 315

<210> SEQ ID NO 56
<211> LENGTH: 317
<212> TYPE: PRT
<213> ORGANISM: Artificial Sequence
<220> FEATURE:
<223> OTHER INFORMATION: fusion polypeptide

<400> SEQUENCE: 56

Arg Asp Glu Thr Ile Gln Val Lys Gly Asn Gly Tyr Val Gln Ser Pro
1               5                   10                  15

Arg Phe Pro Asn Ser Tyr Pro Arg Asn Leu Leu Leu Thr Trp Arg Leu
            20                  25                  30

His Ser Gln Glu Asn Thr Arg Ile Gln Leu Val Phe Asp Asn Gln Phe
        35                  40                  45

Gly Leu Glu Glu Ala Glu Asn Asp Ile Cys Arg Tyr Asp Phe Val Glu
    50                  55                  60

Val Glu Asp Ile Ser Glu Thr Ser Thr Ile Ile Arg Gly Arg Trp Cys
65                  70                  75                  80

Gly His Lys Glu Val Pro Pro Arg Ile Lys Ser Arg Thr Asn Gln Ile
                85                  90                  95

Lys Ile Thr Phe Lys Ser Asp Asp Tyr Phe Val Ala Lys Pro Gly Phe
            100                 105                 110

Lys Ile Tyr Tyr Ser Leu Leu Glu Asp Phe Gln Pro Ala Ala Ala Ser
        115                 120                 125

Glu Thr Asn Trp Glu Ser Val Thr Ser Ser Ile Ser Gly Val Ser Tyr
    130                 135                 140

Asn Ser Pro Ser Val Thr Asp Pro Thr Leu Ile Ala Asp Ala Leu Asp
145                 150                 155                 160

Lys Lys Ile Ala Glu Phe Asp Thr Val Glu Asp Leu Leu Lys Tyr Phe
                165                 170                 175

Asn Pro Glu Ser Trp Gln Glu Asp Leu Glu Asn Met Tyr Leu Asp Thr
            180                 185                 190
```

Pro Arg Tyr Arg Gly Arg Ser Tyr His Asp Arg Lys Ser Lys Val Val
            195                 200                 205

Asp Leu Asn Leu Leu Thr Glu Glu Val Arg Leu Tyr Ser Cys Thr Pro
        210                 215                 220

Arg Asn Phe Ser Val Ser Ile Arg Glu Glu Leu Lys Arg Thr Asp Thr
225                 230                 235                 240

Ile Phe Trp Pro Gly Cys Leu Leu Val Lys Arg Cys Gly Gly Asn Cys
                245                 250                 255

Ala Cys Cys Leu His Asn Cys Asn Glu Cys Gln Cys Val Pro Ser Lys
                260                 265                 270

Val Thr Lys Lys Tyr His Glu Val Leu Gln Leu Arg Pro Lys Thr Gly
            275                 280                 285

Val Arg Gly Leu His Lys Ser Leu Thr Asp Val Ala Leu Glu His His
        290                 295                 300

Glu Glu Cys Asp Cys Val Cys Arg Gly Ser Thr Gly Gly
305                 310                 315

<210> SEQ ID NO 57
<211> LENGTH: 303
<212> TYPE: PRT
<213> ORGANISM: Artificial Sequence
<220> FEATURE:
<223> OTHER INFORMATION: fusion polypeptide

<400> SEQUENCE: 57

Arg Asp Glu Thr Ile Gln Val Lys Gly Asn Gly Tyr Val Gln Ser Pro
1               5                   10                  15

Arg Phe Pro Asn Ser Tyr Pro Arg Asn Leu Leu Leu Thr Trp Arg Leu
            20                  25                  30

His Ser Gln Glu Asn Thr Arg Ile Gln Leu Val Phe Asp Asn Gln Phe
        35                  40                  45

Gly Leu Glu Glu Ala Glu Asn Asp Ile Cys Arg Tyr Asp Phe Val Glu
    50                  55                  60

Val Glu Asp Ile Ser Glu Thr Ser Thr Ile Ile Arg Gly Arg Trp Cys
65                  70                  75                  80

Gly His Lys Glu Val Pro Pro Arg Ile Lys Ser Arg Thr Asn Gln Ile
                85                  90                  95

Lys Ile Thr Phe Lys Ser Asp Asp Tyr Phe Val Ala Lys Pro Gly Phe
            100                 105                 110

Lys Ile Tyr Tyr Ser Leu Leu Glu Asp Phe Gln Pro Ala Ala Ala Ser
        115                 120                 125

Val Ser Pro Ser Val Leu Pro Pro Ser Ala Leu Pro Leu Asp Leu Leu
    130                 135                 140

Asn Asn Ala Ile Thr Ala Phe Ser Thr Leu Glu Asp Leu Ile Arg Tyr
145                 150                 155                 160

Leu Glu Pro Glu Arg Trp Gln Leu Asp Leu Glu Asp Leu Tyr Arg Pro
                165                 170                 175

Thr Trp Gln Leu Leu Gly Lys Ala Phe Val Phe Gly Arg Lys Ser Arg
            180                 185                 190

Val Val Asp Leu Asn Leu Leu Thr Glu Glu Val Arg Leu Tyr Ser Cys
        195                 200                 205

Thr Pro Arg Asn Phe Ser Val Ser Ile Arg Glu Glu Leu Lys Arg Thr
    210                 215                 220

Asp Thr Ile Phe Trp Pro Gly Cys Leu Leu Val Lys Arg Cys Gly Gly
225                 230                 235                 240

```
Asn Cys Ala Cys Cys Leu His Asn Cys Asn Glu Cys Gln Cys Val Pro
            245                 250                 255

Ser Lys Val Thr Lys Lys Tyr His Glu Val Leu Gln Leu Arg Pro Lys
            260                 265                 270

Thr Gly Val Arg Gly Leu His Lys Ser Leu Thr Asp Val Ala Leu Glu
        275                 280                 285

His His Glu Glu Cys Asp Cys Val Cys Arg Gly Ser Thr Gly Gly
        290                 295                 300
```